US009321755B2

(12) United States Patent
Tao et al.

(10) Patent No.: US 9,321,755 B2
(45) Date of Patent: Apr. 26, 2016

(54) PROCESS FOR THE SYNTHESIS OF AN INDOLEAMINE 2,3-DIOXYGENASE INHIBITOR

(71) Applicants: Incyte Corporation, Wilmington, DE (US); Incyte Holdings Corporation, Wilmington, DE (US)

(72) Inventors: Ming Tao, Maple Glen, PA (US); William Frietze, Kennett Square, PA (US); David J. Meloni, Bear, DE (US); Lingkai Weng, Malvern, PA (US); Jiacheng Zhou, Newark, DE (US); Yongchun Pan, Newark, DE (US)

(73) Assignees: Incyte Corporation, Wilmington, DE (US); Incyte Holdings Corporation, Wilmington, DE (US)

( * ) Notice: Subject to any disclaimer, the term of this patent is extended or adjusted under 35 U.S.C. 154(b) by 0 days.

(21) Appl. No.: 14/535,781

(22) Filed: Nov. 7, 2014

(65) Prior Publication Data

US 2015/0133674 A1   May 14, 2015

Related U.S. Application Data

(60) Provisional application No. 61/901,689, filed on Nov. 8, 2013.

(51) Int. Cl.
| *C07D 413/04* | (2006.01) |
| *C07C 307/06* | (2006.01) |
| *C07D 271/04* | (2006.01) |
| *C07D 271/08* | (2006.01) |

(52) U.S. Cl.
CPC ............ *C07D 413/04* (2013.01); *C07C 307/06* (2013.01); *C07D 271/04* (2013.01); *C07D 271/08* (2013.01)

(58) Field of Classification Search
None
See application file for complete search history.

(56) References Cited

U.S. PATENT DOCUMENTS

| 3,236,855 | A  | 2/1966  | Jones et al. |
| 3,553,228 | A  | 1/1971  | Freedman et al. |
| 3,948,928 | A  | 4/1976  | Nishimura et al. |
| 4,116,974 | A  | 9/1978  | Farge et al. |
| 4,323,681 | A  | 4/1982  | Wolf et al. |
| 4,699,916 | A  | 10/1987 | Sirrenberg et al. |
| 5,364,864 | A  | 11/1994 | Bigg et al. |
| 5,712,294 | A  | 1/1998  | Robert et al. |
| 6,482,416 | B2 | 11/2002 | Munn et al. |
| 6,482,822 | B1 | 11/2002 | Bigg et al. |
| 6,780,858 | B2 | 8/2004  | Li et al. |
| 7,109,354 | B2 | 9/2006  | Subasinghe et al. |
| 7,144,902 | B1 | 12/2006 | Baucke et al. |
| 8,008,281 | B2 | 8/2011  | Prendergast et al. |
| 8,034,953 | B2 | 10/2011 | Combs et al. |
| 8,088,803 | B2 | 1/2012  | Combs et al. |
| 8,372,870 | B2 | 2/2013  | Combs et al. |
| 8,377,976 | B2 | 2/2013  | Combs et al. |
| 8,450,351 | B2 | 5/2013  | Combs et al. |
| 8,507,541 | B2 | 8/2013  | Combs et al. |
| 8,796,319 | B2 | 8/2014  | Combs et al. |
| 8,822,511 | B2 | 9/2014  | Combs et al. |
| 8,951,536 | B2 | 2/2015  | Combs et al. |
| 8,993,605 | B2 | 3/2015  | Combs et al. |
| 2002/0155104 | A1 | 10/2002 | Munn et al. |
| 2004/0234623 | A1 | 11/2004 | Munn et al. |
| 2006/0194802 | A1 | 8/2006  | Abdellaoui et al. |
| 2007/0037752 | A1 | 2/2007  | Ansorge et al. |
| 2007/0037785 | A1 | 2/2007  | Ansorge et al. |
| 2007/0038298 | A1 | 2/2007  | Sulner et al. |
| 2007/0185165 | A1 | 8/2007  | Combs et al. |
| 2007/0203140 | A1 | 8/2007  | Combs et al. |
| 2007/0265257 | A1 | 11/2007 | Tanaka et al. |
| 2008/0119491 | A1 | 5/2008  | Combs |
| 2008/0125470 | A1 | 5/2008  | Combs et al. |
| 2008/0146624 | A1 | 6/2008  | Combs et al. |
| 2008/0182882 | A1 | 7/2008  | Combs et al. |
| 2008/0214546 | A1 | 9/2008  | Combs et al. |
| 2008/0214549 | A1 | 9/2008  | Shaw et al. |
| 2009/0163545 | A1 | 6/2009  | Goldfarb |
| 2009/0247586 | A1 | 10/2009 | Dunkel et al. |
| 2011/0165188 | A1 | 7/2011  | Combs et al. |
| 2011/0172279 | A1 | 7/2011  | Combs et al. |
| 2012/0058079 | A1 | 3/2012  | Combs et al. |
| 2013/0123246 | A1 | 5/2013  | Combs et al. |
| 2013/0177590 | A1 | 7/2013  | Combs et al. |
| 2014/0315962 | A1 | 10/2014 | Combs et al. |
| 2014/0377292 | A1 | 12/2014 | Combs et al. |

FOREIGN PATENT DOCUMENTS

| BE | 659467   | 8/1965  |
| CA | 2500113  | 4/2004  |
| DE | 2040628  | 2/1972  |
| EP | 0352832  | 1/1990  |
| EP | 0516520  | 12/1992 |
| EP | 0536424  | 4/1993  |
| EP | 1038874  | 9/2000  |
| EP | 1188747  | 3/2002  |
| JP | 40020710 | 9/1965  |

(Continued)

OTHER PUBLICATIONS

Database Registry Chemical Abstracts Service, Columbus, Ohio, Accession No. RN 503310-69-8, Entered STN: Apr. 17, 2003.*

(Continued)

*Primary Examiner* — Samantha Shterengarts
(74) *Attorney, Agent, or Firm* — Fish & Richardson P.C.

(57) ABSTRACT

The present application is directed to processes and intermediates for making 4-({2-[(aminosulfonyl)amino]ethyl}amino)-N-(3-bromo-4-fluorophenyl)-N'-hydroxy-1,2,5-oxadiazole-3-carboximidamide, which is an inhibitor of indoleamine 2,3-dioxygenase, useful in the treatment of cancer and other disorders.

66 Claims, No Drawings

(56) References Cited

FOREIGN PATENT DOCUMENTS

| | | |
|---|---|---|
| JP | 50-050369 | 5/1975 |
| JP | 58208275 | 12/1983 |
| JP | 60193968 | 10/1985 |
| JP | 62059283 | 3/1987 |
| JP | 02006453 | 1/1990 |
| JP | 4297449 | 10/1992 |
| JP | 06-065269 | 3/1994 |
| JP | 11171702 | 6/1999 |
| JP | 11-513679 | 11/1999 |
| JP | 2000-505815 | 5/2000 |
| JP | 2001158785 | 6/2001 |
| JP | 2001158786 | 6/2001 |
| JP | 2001-233861 | 8/2001 |
| JP | 2002-542165 | 12/2002 |
| RU | 2230742 | 6/2004 |
| SU | 886740 | 12/1981 |
| WO | WO 97/14686 | 4/1997 |
| WO | WO 97/30047 | 8/1997 |
| WO | WO 97/42183 | 11/1997 |
| WO | WO 98/24784 | 6/1998 |
| WO | WO 99/29310 | 6/1999 |
| WO | WO 99/62903 | 12/1999 |
| WO | WO 00/52001 | 9/2000 |
| WO | WO 00/61609 | 10/2000 |
| WO | WO 01/51456 | 7/2001 |
| WO | WO 02/00196 | 1/2002 |
| WO | WO 02/079200 | 10/2002 |
| WO | WO 02/102799 | 12/2002 |
| WO | WO 03/045901 | 6/2003 |
| WO | WO 03/070236 | 8/2003 |
| WO | WO 03/087347 | 10/2003 |
| WO | WO 03/099805 | 12/2003 |
| WO | WO 2004/029031 | 4/2004 |
| WO | WO 2004/093871 | 11/2004 |
| WO | WO 2004/094409 | 11/2004 |
| WO | WO 2005/019190 | 3/2005 |
| WO | WO 2005/037257 | 4/2005 |
| WO | WO 2005/037779 | 4/2005 |
| WO | WO 2006/028284 | 3/2006 |
| WO | WO 2006/067532 | 6/2006 |
| WO | WO 2006/122150 | 11/2006 |
| WO | WO 2006/133417 | 12/2006 |
| WO | WO 2007/068377 | 6/2007 |
| WO | WO 2007/075598 | 7/2007 |
| WO | WO 2008/036642 | 3/2008 |
| WO | WO 2008/036643 | 3/2008 |
| WO | WO 2008/036652 | 3/2008 |
| WO | WO 2008/036653 | 3/2008 |
| WO | WO 2008/058178 | 5/2008 |
| WO | WO 2008/073825 | 6/2008 |
| WO | WO 2010/005958 | 1/2010 |

OTHER PUBLICATIONS

A.R. Katritzky et al., "Synthesis of mono and symmetrical di-N-hydroxy- and N-aminoguanidines", Journal of Organic Chemistry, 71(18):6753-8 (2006).

Ait-Mohand, Samia. and Dolbier, Jr. William R., "New and Convenient Method for Incorporation of pentafluorosulfanyl ($SF_5$) Substituents Into Aliphatic Organic Compounds", Organic Letters, 4(17), 3013-3015, 2002.

Andrianov et al. "Degenerate Rearrangement of 3-amino-1,2,5-oxadiazole-4-carboxamidoxime", Khimiya Geterotsiklicheskikh Soedinenii, (1988), (12), 1701 (and abstract Database Hcaplus, on STN, 1989:515108, No. 111:115108).

Andrianov et al., "4-aminofurazan-3-hydroximic halides", Institute of Organic Synthesis, 5:581-585 (1992) translation of "Acid halides of 4-aminofurazan-3-carbohydroximic acid", Khimiya Geterotsiklicheskikh Soedinenii, (1992), (5), 687-91 and abstract Database Hcaplus, on STN, 1993:212973, No. 118:212973.

Andrianov et al., "Acid halides of 4-aminofurazan-3-carbohydroxamic acids", Chemistry of Heterocyclic Compounds, Latvian Institute of Organic Chemistry, vol. 30, 3:370-371 (1994) (English translation of Khimiya Geterotsiklicheskikh Soedinenii, (3), 420-21) and abstract Database Hcaplus STN File CA, 1995:376582; 123:198702.

Andrianov et al., "Rearrangements of 1-oxa-2-azoles. 2. Structure and isomerization of pentamethyleneamidoximes of 4-aminofurazan-3-carboxylic acid", Khimiya Geterotsiklicheskikh Soedinenii, (1991), (1), 122-3 (and abstract Database Hcaplus, STN, 1991:449555, No. 115:49555).

Andrianov et al., "Rearrangements of 5-trifluoromethyl-1,2,4-oxadiazoles by action of ammonia and amines", Institute of Organic Synthesis, Academy of Sciences of the Latvian SSR, p. 707 translation of "Ammonia- and amine-induced rearrangements of 5-(trifluoromethyl)-1,2,4-oxadiazoles", Khimiya Geterotsiklicheskikh Soedinenii, (1988), (6), 856-7 and abstract Database Hcaplus, on STN, 1989:212695, No. 110:212695).

Andrianov et al., "Ring formation reactions of 4-aminofurazan-3-carboxyamidoximes", Chemistry of Heterocyclic Compounds, 30(4):470-474 (1993) (English translation of Andrianov et al., "4-aminofurazan-3-carboxamidoxime cyclization", Khimiya Geterotsiklicheskikh Soedinenii (4):534-8 (1994) (and abstract Database Caplus No. 1995:393128; 122:290788); XP002526509 (1994).

Andrianov et al., "Synthesis and properties of derivatives of 4-aminofuroxan-3-carboxylic acid", Chemistry of Heterocyclic Compounds, 33(8), 973-976 (1997), translation of Khimiya Geterotsiklicheskikh Soedinenii, (1997) No. 8, pp. 1115-1119 and abstract Database Hcaplus, on STN, 1998:221958, No. 128:308445.

Andrianov et al., "Synthesis of furazans by rearrangement of 3-acyl-1-oxa-2-azole oximes", UDC 547.793.07(047) 2611(90):1199-1213 (1991), Institute of Organic Synthesis, Academy of Science of the Latvian SSR, (Translation of Khimiya Geterotsiklicheskikh Soedinenii, (1990) No. 11, pp. 1443-1459).

Andrianov et al., "Synthesis, structure, and rearrangement of 4-aminofurazan-3-carboxamide oximes", UDC 547.793.2, 29(5):877-880 (1994), (translation of Zhurnal Organicheskoi Khimii, (1993), 29(5), 1062-6) and abstract Database Hcaplus, on STN, 1994:270259, No. 120:270259; XP002526508 (1993).

Andrianov, et al., "Synthesis and properties of 4-amino-3-cyanofurazan", Chemistry of Heterocyclic Compounds, vol. 30, No. 5, pp. 608-611 (1994), translation of Khimiya Geterotsiklicheskikh Soedinenii, (5), 693-6 (1994) with abstract Database Hcaplus, on STN 1995:374071, No. 123:198701.

Andrianov et al., "4-Aminofurazan-3-carbohydroximic acid halides", Khimiya Geterotsiklicheskikh Soedinenii, (1994), (3), 420-5, and abstract.

Areschka et al., "Studies on the benzofuran series. LXI. 3-Benzofuranylacetamidoximes with antihypertenstive potential", European Journal of Medicinal Chemistry, (1977), 12(1), 87-91 (with English abstract).

Astigiano, et al., Neoplasia, 7(4):390-396 (2005).

Bagdasarov, et al., "Extraction—photometric determination of copper and cobalt with oxime derivatives of benzimidazole", Zavodskaya Laboratoriya (1976), 42(2), 143-144 (Non-English Reference), (in U.S. Appl. No. 11/856,982 in Jan. 29, 2010 Office Action—copy provided with reference).

Beaudegnies et al., "Synthesis of furazan conjugated new heterocycles", Heterocycles, (2003), 60(11), 2417-2424 and abstract Database Hcaplus, on STN, 2003:865834, No. 140:59538.

Belik et al., "Descriptor v'cp-aided study of the rearrangement of 1-oxa-2-azoles", Zhurnal Organicheskoi Khimii, 30(5), 757-9 (1994) with abstract STN File CA, 122:238877; 1995:326366.

Belik, et al., "Theoretical investigation of rearrangements of 1-oxa-2-azole-3-carboxamidoximes", Russian Journal of Organic Chemistry, 34(4), 543-548 (1998) (Translation of Zhurnal Organicheskoi Khimii 34(4), 577-582) (with abstract STN File CA, 130:209340; 999:79495).

Berge, et al., "Pharmaceutical Salts", J. of Pharmaceutical Science, vol. 66 No. 1, pp. 1-19 (1977).

Bonda, et al., "Indoleamine 2,3-dioxygenase and 3-hydroxykynurenine modifications are found in the neuropathology of Alzheimer's disease", Redox Rep., 15(4):161-8 (2010).

Brandacher, et al., Clin. Cancer Res., 12(4):1144-1151 (2006) (abstract).

(56) References Cited

OTHER PUBLICATIONS

Brown, et al., "Implications of Interferon-induced Tryptophan Catabolism in Cancer, Auto-immune Diseases and Aids", *Adv. Exp. Med. Biol.*, 294: 425-35 (1991).

Burger et al., "Janus kinase inhibitor INCB20 has antiproliferative and apoptotic effects on human myeloma cells in vitro and in vivo," Mol. Cancer Ther 2009;8(1) Jan. 2009, 26-35.

Chauhan et al., "Antifilarial profile of substituted pyrazoles: a new class of antifilarial agents," *Indian Journal of Chemistry*, Section B: Organic Chemistry Including Medicinal Chemistry (1993), 32B(8), 858-61 (with abstract Database Hcaplus STN File CA, 120:244819; 1994:244819).

Clercq, Journal of Clinical Virology, vol. 30, 2004, pp. 115-133.

'ClinicalTrials.gov' [online] "A Phase 2 Study of the IDO Inhibitor INCB024360 Versus Tamoxifen for Subjects with Biochemical-recurrent-only EOC, PPC or PTC Following Complete Remission with First-line Chemotherapy," [2013], [retrieved on Jul. 25, 2013] URL:<http://clinicaltrials.gov/ct2/show/NCT01685255?term=incyte&rank=4> 4 pages.

'ClinicalTrials.gov' [online] "A Phase 1/2 Randomized, Blinded, Placebo Controlled Study of Ipilimumab in Combination with INCB024360 or Placebo in Subjects with Unresectable or Metastatic Melanoma," [2012] [retrieved on Jul. 25, 2013] URL: http://clinicaltrials.gov/ct2/show/NCT01604889?term=incyte&rank=8 > 3 pages.

Corbett et al. In vivo methods for screening and preclinical testing. Cancer Drug Discovery and Development: Anticancer Drug Development Guide: Preclinical Screening, Clinical Trials, and Approval, 2nd Ed. Teicher, B.A. and Andrews, P.A., Gumana Press Inc., Totowa, NJ, 2004* Too Voluminous to Provide.

Current Protocols in Immunology, vol. 4, Coligan, J.E., et al; Immunotherapy of Cancer, Human Press, 2006, Disis, M.L.* Too Voluminous to Provide.

Database CAPLUS, on STN, 1963: 73272, No. 83, 12528c-e, see RN 90585-88-9 CAPLUS, XP-002467962 dated May 2, 2008, (abstract of Sycheva, et al. "Compaunds with Potential Antitubercular Activity. VI. Amidoximes, amide Hydrazones, and S-Oxides of Thioamides of some Heterocyclic acids", (1962) 32, 3669-74) (1page).

Database CAPLUS, on STN, 1966: 35828, No. 64, 6633a-d, see RN 4698-75-3 CAPLUS, XP-002467245 dated May 2, 2008 (abstract of Sycheva, et al., "Compaunds with Potential Antitubercular Activity. X. Derivatives of Benzoxazole-2-carboxylic acid", (1965) 46-51 (1 page).

Database CAPLUS, on STN, 1975:606233, No. 83: 32463a, 32466a, see RN 55942-51-3 CAPLUS, XP-002467961 dated May 2, 2008 (abstract of Nishimura, Haruki et al., JP Patent No. 50050369, issued May 6, 1975 "Amidoxime Derivatives",) (1 page).

Database CAPLUS, on STN, 1992:6493, No. 116, 6493, XP-002467964, RN 137890-17-6 dated Jun. 2, 2008, (abstract of Andrianov, et al., "Rearrangements of 1-oxa-2-azoles. 4. synthesis and rearrangement of Amidoximes of soxazole-and 4,5-dihydrosoxazole-3-carboxylic acid", (1991) (6), 827-32) (1 page).

Daubener, et al., "IFN-γ Activated Indoleamine 2,3-Dioxygenase Activity in Human Cells Is an Antiparasitic and an Antibacterial Effector Mechanism", Adv. Exp. Med. Biol., 467: 517-24 (1999).

Deeb et al., "Heterocyclic synthesis from 3-amino-4-cyanopyrazole," Collection of Czechoslovak Chemical Communications (1990), 55(3), 728-33 (with abstract Database Hcaplus STN File CA, 113:97502; 1990:497502).

Dranoff et al., "Vaccination with irradiated tumor cells engineered to secrete murine granulocyte-macrophage colony-stimulating factor stimulates potent, specific, and long-lasting anti-tumor immunity," *Proc. Natl. Acad. Sci, USA*. 90:3539-3543 (1993).

El-Mobayed et al., "Synthesis of heterocyclic compounds containing nitrogen and sulfur from 3-amino-4-cyanopyrazole," *Journal of the Chemical Society of Pakistan* (1989), 11(4), 287-90 (with abstract Database Hcaplus STN File CA, 113:231330; 1990:631330).

Expert Scientific Group on Phase One Clinical Trials Final Report, Nov. 30, 2006, pp. C1, C35-C38.

Feder-Mengus, et al., "High expression of indoleamine 2,3-dioxygenase gene in prostate cancer", *European J. Cancer*, 44 (2008) pp. 2266-2275.

Friberg, M., Jennings, R., et al. Indoleamine 2,3-dioxygenase contributes to tumor cell evasion of T cell-mediated rejection. Int. J. Cancer: 101:151-155, 2002.

Fujii et al., "Oxidation of N6-benzyladenine with m-chloroperoxybenzoic acid: formation of the N(1)-oxide," Heterocycles (1994), 37(1), 219-22 (with abstract Database Hcaplus STN File CA, 121:35143; 1994:435143).

Fujii et al., "Purines. III. Rearrangement of 1-alkoxy-9-alkyladenines to 6-alkoxyamino-9-alkylpurines through isolatable N'-alkoxy-1-alkyl-5-formamidoimidazole-4- carboxamidines ," Tetrahedron (1971), 27(12), 2415-23 (with abstract Database Hcaplus STN File CA, Abstract 75:76739; 1971:476739).

Fujii et al., "Purines. V. Dimroth rearrangement of 1-alkoxyadenines. Synthesis of N-alkoxyadenines," Chemical & Pharmaceutical Bulletin (1971), 19(8), 1731-4 (with abstract Database Hcaplus STN File CA, Abstract 75:110279; 1971:510279).

Fujii et al., "Purines. XLVIII. Syntheses and proton nuclear magnetic resonance study of 2-deuterioadenines substituted or unsubstituted at the 9-position and of their N-oxygenated derivatives," Chemical & Pharmaceutical Bulletin (1991), 39(2), 301-8 (with abstract Database Hcaplus STN File CA, 114:247645; 1991:247645).

Fujii et al., "Purines. XV. Conversion of N,9-dimethyladenine into the 1,9-dimethyl isomer. Reverse operation of the dimroth rearrangement," Chemical & Pharmaceutical Bulletin (1974), 22(10), 2211-16 (with abstract Database Hcaplus STN File CA, Abstract 82:43349; 1975:43349).

Fujii, et al., "Antitumor activities of some fifty compounds related to adenine derivatives," Yakugaku Zasshi (1977), 97(6), 689-91(with abstract Database Hcaplus STN File CA, 87:111278; 1977:511278).

Gasparri, et al., "Critical role of indoleamine 2,3-dioxygenase in tumor resistance to repeated treatments with targeted IFNγ", *Mol. Cancer Ther.*, 7(12) pp. 3859-3866 (2008).

Giron, D.J., "Applications of Thermal Analysis and Coupled Techniques in Pharmaceutical Industry", *J Therm. Anal. Cal.* (2002), 68, pp. 335-357.

Giron, D.J., "Investigations of Polymorphism and Pseudo-Polymorphism in Pharmaceuticals by Combined Thermoanalytical Techniques", *J. Therm. Anal. Cal.* (2001), 64, pp. 37-60.

Graham, B.S., "Clinical trials of HIV vaccines." HIV Molecular Immunology Database 2000. Edited by: Korber BT, Brander C, Haynes BF, Koup R, Kuiken C, Moore JP, Walker BD, and Watkins D. Published by: Theoretical Biology and Biophysics Group, Los Alamos National Laboratory, Los Alamos, NM. pp. 1-20-38.

Greene, et al., Protective Groups in Organic Synthesis, 2d. Ed., Wiley & Sons, 1991* Too Voluminous to Provide.

Griesser, "The Importance of Solvates" in Polymorphism in the Pharmaceutical Industry, 211-233 (Rolf Hilfiker, ed., 2006).

Grohmann, et al., "Tolerance, DCs and tryptophan: much ado about IDO", Trends Immunol., 24:242-8 (2003).

Gura, "Cancer Models: Systems for Identifying New Drugs are Often Faulty," Science, vol. 278, No. 5340, pp. 1041-1042 (1997).

Higuchi et al., "Pro-drugs as Novel Delivery Systems," vol. 14 of the A.C.S. Symposium Series Bioreversible Carriers in Drug Design, ed. Edward B. Roche, American Pharmaceutical Association and Pergamon Press, 1987* Too Voluminous to Provide.

Honig et al., "From bench to clinic and back: perspective on the 1st IQPC Translational Research Conference", *Journal of Translational Medicine*, 2:44 (2004) pp. 1-8.

Hoshi et al., "Indoleamine 2,3-dioxygenase is highly expressed in human adult T-cell leukemia/lymphoma and chemotherapy changes tryptophan catabolism in serum and reduced activity", *Leukemia Research*, 33 pp. 29-45 (2009).

Hou, et al., Cancer Res 67(2):792-801 (2007).

Hwu P, et al., "Indoleamine 2,3-dioxygenase production by human dendritic cells results in the inhibition of T cell proliferation", *J. Immunol.* 164(7):3596-9, (2000).

Ichikawa, T. et al., "A new synthesis of adenine and 4-aminoimidazole-5-carboxamide", J. Heterocycl. Chem., vol. 2 No. 3, pp. 253-255 (1965) (with STN File CA, abstract 68:78253).

(56) References Cited

OTHER PUBLICATIONS

Inaba et al., "Role of the immunosuppressive enzyme indoleamine 2,3-dioxygenase in the progression of ovarian cancer", Gyn. Oncol. 115, 185-92 (2009).
Ino, et al., *British Journal of Cancer*, 95:1555-1561 (2006).
Itaya et al., "Purines. XVIII. Kinetic studies of the Dimroth rearrangement of 1-alkoxy-9-methyladenines and 1-benzyloxyadenosine. Effect of 1-benzyloxy and 9-β-D-ribofuranosyl groups on the rates of the ring opening and the reclosure," *Chemical & Pharmaceutical Bulletin* (1975), 23(11), 2643-53 (with abstract Database Hcaplus STN File CA, Abstract 84:44592; 1976:44592) [prev. under Fuji but it's Itaya].
Itaya et al., "Purines. LXXII. Oxidation of N6-alkyladenines with m-chloroperoxybenzoic acid leading to N6-alkyladenine 1-oxides," *Chemical &Pharmaceutical Bulletin* (1996), 44(5), 967-971, (with abstract Database Hcaplus STN File CA, 125:86583; 1996:325165; CAS RN 155720-89-1).
Itaya et al., "Purines. LXXV. Dimroth rearrangement, hydrolytic deamination, and pyrimidine-ring breakdown of 7-alkylated 1-alkoxyadenines: N(1)-C(2) versus N(1)-C(6) bond fission," *Chemical & Pharmaceutical Bulletin* (1997), 45(5), 832-841(with abstract Database Hcaplus STN File CA, 127:65632, 1997:349657).
Ji, et al., "Provision of Granulocyte-Macrophage Colony-Stimulating Factor Converts an Autoimmune Response to a Self-Antigen into an Antitumor Response", *J. Immunol*, 2005, 175:1456-63.
Jordan, V. C. Nature Reviews: Drug Discovery, 2, 2003, p. 205.
Kamb, "What wrong with our cancer models?" Nature Reviews Drug Discovery 4, pp. 161-165 (2005).
Karanikas et al., "Indoleamine 2,3-Dioxygenase (IDO) Expression in Lung Cancer", *Cancer Biology & Therapy*, vol. 6, Issue 8 pp. 1258-1262, (2007).
Guillory, "Generation of Polymorphs, Hydrates, Solvates, and Amorphous Solids", in Polymorphism in Pharmaceutical Solids, 183-226 (Harry G. Britain, ed., 1999).
Koblish, et al., "Hydroxyamidine Inhibitors of Indoleamine-2,3-dioxygenase Potently Suppress Systemic Tryptophan Catabolism and the Growth of IDO-Expressing Tumors", *Molecular Cancer Therapeutics*, 9(2):489-498 (Published Online Feb. 2, 2010 at 10.1158/11535-7163.MCT-09-0628).
Koblish, et al., "Potent, Orally Active Hydroxylamidine Inhibitors of Indoleamine-2,3-dioxygenase Suppress Growth of IDO1-expressing Tumors through Systemic Inhibition of Tryptophan Catabolism", 24th Annual Meeting of the International Society for the Biological Therapy of Cancer (ISBTC) in National Harbor MD/Washington DC (Oct. 30, 2009) (poster—1 page) and abstract *J. Immunother*. vol. 32, No. 9 (2009) p. 1005.
Kocevar et al., "Neighboring group participation in formation of condensed azines. Formation of pyrazolo[3,4-b]pyrazines, isoxazolo[4,5-b]pyrazines and isothiazolo[5,4-b]pyridine. Heterocycles. CCX," Monatshefte fuer Chemie (1982), 113(6-7), 731-44 (with abstract Database Hcaplus STN File CA, 97:182276; 1982:582276).
Kocevar et al., "New synthetic approach for pyrazolo[3,4-b] pyrazines and isoxazolo[4,5-b] pyrazines," *Heterocycles* (1982), 19(2), 339-42 (with abstract Database Hcaplus STN File CA, 96:162655; 1982:162655).
Kocevar et al., "Simple Procedure for the Synthesis of Pyridinecarbohydroximoyl Chlorides and Bromides", Synth. Commun., 18(12), 1427-1432 (1988).
Kocevar et al., "Some new synthetic approaches for the preparation of pteridine 3-oxides and pteridines," *Heterocycles* (1981), 15(1), 293-6 (with abstract Database Hcaplus STN File CA, 94:121470; 1981:121470).
Kohl, et al., "IDO and clinical conditions associated with depressive symptoms", Curr. Drug Metab., 8:283-7 (2007).
Kola and Landis, "Can the pharmaceutical industry reduce attrition rates?" Nature Reviews Drug Discovery 3, pp. 711-715 (2004).
Leaf, Clifton, "Why are we losing the war on cancer (and how to win it)," Health Administrator vol. XVII, No. 1:172-183 (2005).

Liu et al., "Estimation and prediction on heats of formation for nitro furazan series compounds with new molecular subgraph", *Huaxue Wuli Xuebao*, (2002), 15(5), 351-356 and abstract Database Hcaplus, on STN, 2002:880171, No. 138:204550.
Liu, et al., "INCB024360, a Potent and Selective Inhibitor of Indoleamine 2,3-dioxygenase (IDO1) as a Novel Cancer Immunotherapeutic Agent", Mol Cancer Ther, 8(12 Suppl):Poster #C106 (2009).
Liu, et al., "Indoleamine 2,3-Dioxygenase, an Emerging Target for Anti-Cancer Therapy", Current Cancer Drug Targets, 9:938-952 (2009).
Liu et al., "Selective inhibition of IDO1 effectively regulates mediators of antitumor immunity," *Blood*, 2010, 115:3520-3530.
Lob, et al., "Inhibitors of indoleamine-2,3-dioxygenase for cancer therapy: can we see the wood for the trees?", Nature Reviews Cancer, 9:445-52 (2009).
Logan, et al., "HeLa cells cocultured with peripheral blood lymphocytes acquire an immuno-inhibitory phenotype through up-regulation of indoleamine 2,3-dioxygenase activity", Immunology, 105: 478-87 (2002).
Longo, G., "Dioximes. LXXVIII", *Gazzetta Chimica Italiana*, (1931), 61, 575-83 (and abstract Database Hcaplus, on STN, 1932:6117, No. 26:6117).
Luo et al. Cell, 2009, 136, pp. 823-837.
Mailankot, et al., "Cell Cycle Arrest by Kynurenine in Lens Epithelial Cells", IOVS, 49:5466-5475 at 5474 (2008).
Medawar, "Some immunological and endocrinological problems raised by the evolution of viviparity in vertebrates", Symp. Soc. Exp. Biol. 7: 320-38 (1953).
Mellman et al., "Cancer immunotherapy comes of age," *Nature*, 2011, 480:480-489.
Meyer, Kevin G., "Improved synthesis of 3-aminofurazan-4-carboxylic acid", Organic Preparations and Procedures INt. 36(4):361-362 (2004).
Milletti et al., "New and Original pKa Prediction Method Using Grid Molecular Interaction Fields", *Journal of Chemical Information and Modeling*, 2007, 47(6), 2172-2181 and abstract Database Hcaplus, on STN, 2007:1104249, No. 148:33199.
Mishnev et al., "Crystal and molecular structure of isomers of the oxime of 3-aminofurazanoyl piperidine", *Institute of Organic Synthesis, Latvian Academy of Sciences*, pp. 349-352 translation of Zhurnal Strukturnoi Khimii, 32(3):45-48 (1991).
Morissette, et al., "High-Throughput Crystallization: Polymorphs, Salts, Co-Crystals and Solvates", Adv. Drug Delivery Rev., 56:275-300 (2004).
Muller et al, "Inhibition of indoleamine 2,3-dioxygenase, an immunoregulatory target of the cancer suppression gene Bin1, potentiates cancer chemotherapy", Nature Med., 11:312-9 (2005).
Munn et al., "Expression of indoleamine 2,3-dioxygenase by plasmacytoid dendritic cells in tumor-draining lymph nodes", *J. Clin. Invest.*, 114(2): 280-90 (2004).
Munn et al., "Potential Regulatory Function of Human Dendritic Cells Expressing Indoleamine 2,3-Dioxygenase", *Science* 297: 1867-70 (2002).
Munn et al., "Prevention of Allogeneic Fetal Rejection by Tryptophan Catabolism", *Science* 281: 1191-3 (1998).
Munn, et al., *Journal of Clinical Investigation*, 117(5):1147-1154 (2007).
Neidle, Stephen, "Cancer Drug Design and Discovery," (Elsevier/Academic Press, 2008) pp. 427-431.
Nekrasov et al., "Effect of particular structural features of aminooximes on formation of final products in reactions with 5-aryl-2,3-dihydrofuran-2,3-diones", *Russian Journal of Organic Chemistry*, (2000), 36(2), 263-268, (*Translation of Zhurnal Organicheskoi Khimii*,vol. 36, No. 2 (2000) pp. 285-290) and abstract Database Hcaplus, on STN, 2000:643842, No. 133:321845.
Newton et al., "Pharmacodynamic assessment of INCB024360, an inhibitor of indoleamine 2,3-dioxygenase 1 (IDO1) in advanced cancer patients," *ASCO Annual Meeting*, 2012, 16 pages.
Nicolau et al., "A new method for the synthesis of nonsymmetrical sulfamides using Burgess-type reagents," Angewandte Chemie, 41(20):3866-3870 (2002).

(56) References Cited

OTHER PUBLICATIONS

Nonaka et al., "Indoleamine 2,3-dioxygenase promotes peritoneal dissemination of ovarian cancer through inhibition of natural killercell function and angiogenesis promotion," *Int. J Oncology*, 2011, 38:113-120.

Okamoto, et al., Clin Cancer Res 11(16):6030-6039, at 6037-6038 (2005).

Pellegrin, et al., "Enhanced enzymatic degradation of tryptophan by indoleamine 2,3-dioxygenase contributes to the tryptophan-deficient state seen after major trauma", Shock, 23:209-215 (2005).

Peterson et al., Evaluation of Functionalized Tryptophan Derivatives and related Compounds as Competitive Inhibitors of Indoleamine 2,3-Dioxygenase *Med. Chem. Res.* 3, 531-544, (1994).

Physicians' Desk Reference (PDR, e.g., 1996 edition, Medical Economics Company, Montvale, NJ) Zh. Org. Chim. (1993), 29, 1062-1066.

Pivina et al., "Comparative characteristic of energy content calculating methods for the furazan series as an example of energetic materials", *Propellants, Explosives, Pyrotechnics*, (1995), 20(1) 5-10 and abstract Database Hcaplus, on STN, 1995:464236, No. 122:217824.

Poluektova et al., "Generation of cytotoxic T cells against virus-infected human brain macrophages in a murine model of HIV-1 encephalitis", *J. Immunol.*, 168(8):3941-9 (2002).

Potula et al., "Inhibition of indoleamine 2,3-dioxygenase (IDO) enhances elimination of virus-infected macrophages in an animal model of HIV-1 encephalitis", Blood, 106:2382-90 (2005).

Quan, et al., Expert Opin. Biol. Ther., 8:1705 at 1714 (2008).

Rakitin et al., "Reaction of furoxannitrolic acids with nitrogen tetroxide", *Khimiya Geterotsiklicheskikh Soedinenii*, (1993), (9), 1283-7 (with abstract Database Hcaplus, on STN, 1994:244883, No. 120:244883).

Rakitin et al., "Synthesis of Furaxanenitrolic acids", N. D. Zelinskii Institute of Organic Chemistry, Russian Academy of Sciences, 117913 Moscow pp. 952-954 (1994), Translated from *Khimiya Geterotsiklicheskikh Soedinenii*,(1993), (8), 117-19 (with abstract Database Hcaplus, on STN, 1994:164073, No. 120:164073).

Ravin, Louis J., "Preformulation", *Remington's Pharmaceutical Sciences*, 17th ed., Mack Publishing Company, Easton, PA., Chapter 76, pp. 1409-1423 (1985).

Riesenberg et al., "Expression of Indoleamine 2,3-Dioxygenase inTumor Endothelial Cells Correlateswith Long-term Survival of Patients with Renal Cell Carcinoma", Clin. Cancer Res., vol. 13 Issue 23 pp. 2993-3002 (2007).

Riffaud, et al., "Sur les propriétés analgésiques at antiinflammatoires des benzofuryl-2 amidoximes", European Journal of Medicinal Chemistry, Editions Scientifique Elsevier, Paris, Fr., vol. 1796, pp. 577-580, (1982) (please see ISRPCTUS2007078759 regarding the relevance of this reference).

Roberts Jr. et al., "Trends in the Risks and Benefits to Patient with Cancer Participating in Phase 1 Clinical Trials," JAMA 292(17):2130-2140 (2004).

Robev et al., "Pharmacological study of newly synthesized 2-phenyl-4-anilinopyrimidine-5-amidoxime," Doklady Bolgarskoi Akademii Nauk (1982), 35(10), 1451-4 (with abstract Database Hcaplus STN File CA, 98:191493; 1983:191493).

Robinson et al., "The Role of IFN-γ and TNF-α-Responsive Regulatory Elements in the Synergistic Induction of Indoleamine Dioxygenase," J Interferon Cytokin Res., 2005, 25(1):20-30.

Roche, Edward B., Bioreversible Carriers in Drug Design, ed., American Pharmaceutical Association and Pergamon Press, 1987* Too Voluminous to Provide.

Rodriguez-Spong et al., "General principles of pharmaceutical solid polymorphism: a supramolecular perspective", *Advanced Drug Delivery Review*, (2004), 56, pp. 241-274.

Romanova et al., "Synthesis and reactivity of azidomes: III 1-Azido (4-amino-1, 2, 5-oxadiazol-3-yl) aldoxime in the Cycloaddtion Reaction," *Russian J of Org. Chem.*, 39(4), 574-578 (translation of *Zhurnal Organicheskoi Khimii*, vol. 39 No. 4, pp. 610-615 (2002)).

Rozhov et al., "Synthesis of 1,2,4-oxadiazole-, pyrrole- and 1,2,3-triazole-substituted (1,2,3-triazol-1-yl)furazans", *Mendeleev Communications*, 2008, 18(3), 161-163 and abstract Database Hcaplus, on STN, 2008:880463, No. 150:352019.

Sako, "Product class 19: pyridopyrimidines," *Science of Synthesis* (2004), 16, 1155-1267 (and abstract Database Hcaplus STN File CA, 142:197902; 2004:205975).

Sambrook, J, Russel, D. Molecular Cloning: A laboratory Manual (3rd edition). Cold Spring Harbor Laboratory Press. Cold Spring Harbor, NY, USA. 2001* Too Voluminous to Provide.

Schafer et al., "Failure is an option: learning from unsuccessful proof of concept trials", *Drug Discovery Today*, vol. 13, Nos. 21/22, pp. 913-916 (2008).

Scherle, P., "Characterization of Novel and Potent Inhibitors of the Immunoregulatory Enzyme Indoleamine 2,3-Dioxygenase (IDO) for Use as Cancer Therapy" presented on Mar. 5, 2009 at the Translational Research Cancer Center Consortium annual meeting in Philadelphia, PA.

Search Run Jul. 13, 2010/Scifinder, 10 pages.

Search Run Jul. 28, 2009 / HCAPLUS, 95 pgs.

Search Run Jul. 28, 2009/Registry File Compounds, 107 pgs.

Search Run STN International "11641284" dated Jan. 16, 2009 (93 pages).

Shaposhnikov et al., "New Heterocycles with a 3-Aminofurazanyl Substituent", *Russian Journal of Organic Chemistry*, (2002), 38(9), 1351-1355, (*Translation of Zhurnal Organicheskoi Khimii*, (2002), 38(9), 1405-8, and abstract Database Hcaplus, on STN, 2002:953422, No. 138:368816.

Sheremetev et al., "Hydroxylammonium salts of Furazan family", *International Annual Conference of ICT* (2003), 34th, 101/1-101/10 and abstract Database Hcaplus, on STN, 2003:641413, No. 139:383553.

Sheremetev et al., "Synthesis of secondary and tertiary aminofurazans", Russian Chemical Bulletin 53(3), 596-614 (2004), translation from Izvestiya Akademii Nauk, Seriya Khimicheskaya, 53(3), pp. 569-586 (Mar. 2004) (and abstract Database Caplus No. 2004:589877; 142:219211); XP002526510 (2004).

Sherif et al., "Syntheses with heterocyclic β-enaminonitriles. An expeditious synthetic approach to polyfunctionally substituted 5-phenyl-sulfonylthiophenes and their fused derivatives," *Monatshefte fuer Chemie* (1997), 128(6/7), 687-696 (with abstract Database Hcaplus STN File CA, 127:331458; 1997:619483).

Shih et al., Medicinal Research Reviews, Vol, 24, 2004, pp. 449-474.

Sinditskii et al., "Study on combustion of new energetic furazans", *29th International Annual Conference of ICT* (Jun. 30-Jul. 3, 1998) (*Energetic Materials*), 170.1-170.11 and abstract Database Hcaplus, on STN, 1998:498929, No. 129:163569.

Soliman et al., "Indoleamine 2,3-Dioxygenase: Is it an Immune Suppressor", Cancer J., 16, 354-59 (2010).

Soliman et al., "A phase I study of 1-methyl-D-tryptophan in patients with advanced malignancies," *J Clin Oncol.*, 2012, suppl; abstr 2501.

Sono, et al., "Indoleamine 2,3-Dioxygenase", J. Biol. Chem. 255(4), 1339-1345 (1980).

Souillac, et al., Characterization of Delivery Systems, Differential Scanning Calorimetry, pp. 217-218 in Encyclopedia of Controlled Drug Delivery, (1999), John Wiley & Sons, pp. 212-227.

Spasova et al., "Certain derivatives of pyrazole as potential antimetabolites of 4(5)-amino-imidazole-5(4)-carboxamide," Progress in Chemotherapy, (Antibacterial, Antiviral, Antineoplast.), Proceedings of the 8th International Congress of Chemotherapy Athens 1973, vol. 3, 841-4 (with abstract Database Hcaplus STN File CA, 84:54765; 1976:54765).

Spasova et al., "Inhibition of the growth of L. casei by some pyrazole analogues of 5(4)-aminoimidazole-4(5)-carboxamide," Doklady Bolgarskoi Akademii Nauk (1975), 28(11), 1517-20 (with abstract Database Hcaplus STN File CA, Abstract 84:99208; 1976:99208).

Speeckaert et al., "Indoleamine 2,3-dioxygenase, a new prognostic marker in sentinel lymph nodes of melanoma patients", European Journal of Cancer, (2012), 48, 2004-2011.

STN File CA, Abstract 145:457146 (abstract of Wang et al, "Experimental study on synthesis of 3-amino-4-chloroximinofurazan" Hanneng Cailiao (2005), 13 (Suppl.), 1-3) (1 page) (also filed under Wang Aug. 5, 2010).

(56) References Cited

OTHER PUBLICATIONS

Storey, et al., "Automation of Solid Form Screening Procedures in the Pharmaceutical Industry-How to Avoid the Bottlenecks", Crystallography Reviews, 10(1):45-46 (2004).
Takikawa et al., "Mechanism of Interferon-γ Action," J. Biol. Chem. 263(4):2041-8 (1988).
Tan, et al., "Manipulation of indoleamine 2,3 dioxygenase; a novel therapeutic target for treatment of diseases", Expert Opin. Ther. Targets, 13:987-1012 (2009).
Tang, et al., Zhongguo Shi Yan Xue Ye Xue Za Zhi. 14(3):539-42 (2006) (Abstract).
Taneja et al., "MMTV mouse models and the diagnostic values of MMTV-like sequences in human breast cancer," Expert Rev Mol Diagn., 2009, 9(5):423-440.
Taylor, et al., "Relationship between Interferon-γ, indoleamine 2,3-dioxygenase, and tryptophan catabolism", FASEB J., 5:2516-22 (1991).
Terness, et al., "Inhibition of Allogenieic T cell Proliferation by Indoleamine 3,3-Dioxygenase-expressing Dendritic Cells: Mediation of Suppression by Tryptophan Metabolites", J.Exp. med., 196,(4),447-457, (2002).
Trinh and Hwu, "Ipilimumab in the treatment of melanoma," Expert. Opin, Biol. Ther., 2012, 12(6):773-782.
Tselinskii et al., "Synthesis and reactivity of carbohydroximoyl azides: II. 4-substituted 1,2,5-oxadiazole-3-carbohydroximoylazides and 1-hydroxy-5-(4-R-1,2,5-oxadiazol-3-yl)tetrazoles", Russian Journal of Organic Chemistry, (2001), 37(11), 1638-1642, translation of Zhurnal Organicheskoi Khimii (2001), 37(11), 1708-1712 (with abstract Database Hcaplus, on STN, 2002:200728, No. 137:20337).
Uyttenhove, et al., "Evidence for a tumoral immune resistance mechanism based on tryptophan degradation by indoleamine 2,3-dioxygenase", Nat. Med., 9(10):1269-1274, (2003).
Vippagunta, et al., "Crystalline Forms", Adv. Drug Delivery Rev., 48:3-26 (2001).
Wang et al., "Synthesis of 3-amino-4-aminoximidofurazan and its crystal structure", Hecheng Huaxue, (2006), 14(3), 234-239 (with abstract Database Hcaplus, on STN, 2006:616681, No. 146:206250.
Wang et al., "500 Gram-grade synthesis of 3-amino-4-aminoximinofurazan," Hanneng Cailiao (2006), 14(1), 27-28 (3 pages); (with Database Hcaplus STN File CA, 145:191465; 2006:477562) (1 page).
Wang et al., "Crystal structure of 3-amino-4-acylaminoximinofurazan", Chinese Journal of Energetic Materials, translation of Hanneng Cailiao, 14(6), 441-445 (2006) with abstract Database Hcaplus, on STN, 2007:380035, No. 148:382415.
Wang et al., "Furazan-functionalized tetrazolate-based salts: a new family of insensitive energetic materials", Chemistry—A European Journal, 2009, 15(11), 2625-2634 and abstract Database Hcaplus, on STN, 2009:347940, No. 150:518273.
Wang et al.,, "Synthesis and crystal structure of 3,6-bis(3'-aminofurazan-4-yl)-1,4-dioxa-2,5-diazacyclohexane-2,5-diene", Huaxue Yanjiu Yu Yingyong (2006), 18(12), 1398-1402 (with abstract Database Hcaplus, on STN, 2007:633470, No. 148:561814).
WebMD entry for Parkinson's Disease Prevention, obtained from http://www.webmd.com/parkinsons-disease/guide/parkinsonsdisease-prevention on Jul. 19, 2012 (2 pages).
Wichers et al., "The role of indoleamine 2,3-dioxygenase (IDO) in the pathophysiology of interferon-α-induced depression", J. Psychiatry Neurosci., 29(1): 11-17 (2004).
Wieland et al, "Zur Konstitution der polymeren Knallsauren. Pericyanilsaure, Epicyanilsaure and Metacyanilsaure", Eingelaufen am 25 pp. 54-78 (1929).
Wieland et al., "Zur Konstitution der polymeren Knallsauren. X", Aus dem Chem. Laboratorium der Bayr. Akademie der Wissenschaften zu Munchen, Eingelaufen am 23, pp. 43-53 (1929).
Wikipedia, "indoleamine 2,3-dioxygenase"; downloaded on Jan. 16, 2009 http://en.wikipedia.org/wiki/Indoleamine_2,3-dioxygenase (3 pages).
Wiley-VCH Verlag GmbH & Co. KGaA, Weinheim, "Organic Synthesis: General Remarks", pp. 1-16 (2005).
Wirleitner, et al., "Interferon-γ-Induced Conversion of Tryptophan. Immunologic and Neuropsychiatric Aspects", Curr. Med. Chem., 10: 1581-91 (2003).
Wong et al., "Programmed death-1 blockage enhances expansion and functional capacity of human melanoma antigen-specific CTLs," International Immunology, 2007, 19:1223-1234.
Witkiewicz et al., "Expression of Indoleamine 2,3-Dioxygenase in Metastatic Pancreatic Ductal Adenocarcinoma Recruits Regulatory T Cells to Avoid Immune Detection", J. Am. Coll. Surg., vol. 206, No. 5, pp. 849-856 (May 2008).
Witkiewicz et al., "IDO2 Genotyping and Expression in Pancreatic Cancer", J. Am. Coll. Surg., vol. 208, No. 5 pp. 781-789 (May 2008).
Yarovenko et al., "A convenient synthesis of 3-substituted 5-guanidino-1,2,4-oxadiazoles", Russian Chem. Bulletin, vol. 43, No. 1 pp. 114-117 (1994) translation of Izvestiya Akademii Nauk, Seriya Khimicheskaya, (1994), (1), 118-21 and abstract Database Hcaplus, on STN, 1995:542485, No. 123:55777.
Yarovenko et al., "New method for the preparation of 5-amino-1,2,4-oxadiazoles", Bulletin of the Academy of Sciences of the USSR, p. 1924, translation of Izvestiya Akademii Nauk SSSR, Seriya Khimicheskaya, (1991), (9), 2166-7 (3 pages); (with abstract Database Hcaplus, on STN, 1992:21001, No. 116:21001) (1 page).
Yarovenko et al., "New synthesis of nitriles enriched with 15N isotope", Russian Chem. Bulletin, vol. 43, No. 3 pp. 402-404 (1994) translation of Izvestiya Akademii Nauk, Seriya Khimicheskaya, (1994), (3), 444-6 and abstract Database Hcaplus, on STN, 1995:542864, No. 123:111224.
Yarovenko et al., Tetrahedron, 1990, 46 (11), pp. 3941-3952.
Youngdale, Gilbert A. et al., "Synthesis and antifertility activity of 5-(phenoxymethyl)-2-oxazolidinethiones", Journal of Medicinal Chemistry, 9(1), 155-7, 1966 XP002467245 (1965).
Yue et al., "Discovery of Potent Competitive Inhibitors of Indoleamine 2,3-Dioxygenase with in Vivo Pharmacodynamic Activity and Efficacy in a Mouse Melanoma Model," J. Med. Chem. vol. 52, No. 23, pp. 7364-7367 (2009).
Zhou, et al., "Synthesis and properties of 3,4-Bis (4'-aminofurazano-3')furoxan", Huozhayao Xuebao, 30(1), 54-56 (2007) and abstract.
Zidarova et al., "Certain derivatives of 3-aminopyrazole-4-carboxylic acid as potential antimetabolites of 4(5)-aminoimidazole-5(4)-carboxamide in microorganisms," Doklady Bolgarskoi Akademii Nauk (1973), 26(3), 419-22 (with abstract Database Hcaplus STN File CA, Abstract 79:74187; 1973:474187).
Notification on the Result of Substantive Examination, National Office of Intellectual Property, No. 60636/SHTT-SC2, Vietnamese Application No. 1-2007-02634, dated Oct. 7, 2009 (3 pages).
Office Action (non-final) mailed Aug. 3, 2009, U.S. Appl. No. 11/430,441 (15 Pages).
Office Action (final) for U.S. Appl. No. 11/641,284 mailed Oct. 21, 2009 (8 pages).
Office Action (final) mailed Jun. 7, 2010, U.S. Appl. No. 11/430,441 (20 pages).
International Preliminary Report on Patentability for PCT/US2006/17983 dated Nov. 13, 2007 (6 pages).
International Preliminary Report on Patentability for PCT/US2006/048290 dated Jun. 24, 2008 (9 pages).
International Preliminary Report on Patentability for PCT/US2007/078758 dated Mar. 24, 2009 (8 pages).
International Preliminary Report on Patentability for PCT/US2007/003364 dated Aug. 12, 2008 (9 pages).
International Preliminary Report on Patentability for PCT/US2007/078745 dated Mar. 24, 2009 (13 pages).
International Preliminary Report on Patentability for PCT/US2007/078759 dated Mar. 24, 2009 (15 pages).
International Preliminary Report on Patentability for PCT/US2009/049794 issued Jan. 11, 2011 (12 pages).
International Search Report and Written Opinion PCT/US2006/17983 dated Aug. 28, 2006, completed on Aug. 2, 2006) (12 Pages).
International Search Report and Written Opinion for PCT/US2006/048290 dated Sep. 17, 2007 (15 pages).

(56) References Cited

OTHER PUBLICATIONS

International Search Report and Written Opinion for PCT/US2007/003364 mailed Sep. 20, 2007 and completed on Sep. 12, 2007 (16 pages).
International Search Report and Written Opinion for PCT/US2007/078745 completed Feb. 8, 2008 and mailed Jun. 16, 2008 (21 pages).
International Search Report and Written Opinion for PCT/US2007/078759 completed Feb. 6, 2008 and mailed Jun. 16, 2008 (23 pages).
International Search Report and Written Opinion for PCT/US2007/078758 completed Apr. 28, 2008 and mailed May 9, 2008 (12 pages).
International Search Report and Written Opinion PCT/US2009/049794 dated Apr. 26, 2010 (May 6, 2010) (27 Pages).
Eurasia—Search Report for Application No. 200702455 dated Apr. 28, 2008 (1 page).
Extended European Search Report for European Application No. 06759438.2 dated Jun. 5, 2009 (10 pages).
Search Report dated Nov. 12, 2008 and Written Opinion dated Feb. 6, 2009—Singapore Application No. 200717302-4 (18 pages).
Singapore—Final Examination Report, Singapore Patent Application No. 2007/17302-4 dated Sep. 23, 2009 (11 Pages).
Examination Report—EP Patent Application No. 06759438.2 dated Jul. 29, 2010 (4 pages).
Office Action (nonfinal) for U.S. Appl. No. 12/498,782 mailed Jan. 14, 2011 (14 pages).
Office Action (nonfinal) for U.S. Appl. No. 11/641,284 mailed Jan. 29, 2009 (13 pages).
Office Action (nonfinal) for U.S. Appl. No. 11/641,284 mailed May 7, 2010 (9 pages).
Office Action (final) for U.S. Appl. No. 11/641,284 mailed Dec. 15, 2010 (8 pages).
Office Action (nonfinal) for U.S. Appl. No. 11/856,967 mailed Jan. 19, 2010 (5 pages).
Office Action (final) for U.S. Appl. No. 11/856,967 mailed Sep. 24, 2010 (11 pages).
Office Action (nonfinal) for U.S. Appl. No. 11/856,982 mailed Jan. 29, 2010 (10 pages).
Office Action (final) for U.S. Appl. No. 11/856,982 mailed Sep. 17, 2010 (6 pages).
Office Action (nonfinal) for U.S. Appl. No. 11/430,441 mailed Dec. 9, 2010 (15 pages).
Office Action (nonfinal) for U.S. Appl. No. 13/294,711 mailed Jan. 30, 2013 (110 pages).
Office Action (nonfinal) for U.S. Appl. No. 13/294,711 mailed Jul. 25, 2012, (26 pages).
Chilean Patent Office, Application No. 1096-2006, Office Action, Apr. 22, 2007 (2 pages).
State Intellectual Property Office—PR China, Application No. 200680024326-1, Office Action, Jan. 19, 2011 (10 pages).
State Intellectual Property Office—PR China, Application No. 200680024326-1, Office Action, Oct. 23, 2009 (6 pages).
Eurasian Patent Office, Application No. 200702455, Office Action, Oct. 9, 2009 (English translation) (6 pages).
Georgian Patent Office, Application No. AP2006010418, Office Action, Jul. 14, 2009 (English translation) (2 pages).
Malaysian Patent Office, Application No. PI20062122, Office Action, Oct. 18, 2010 (2 pages).
Intellectual Property Office of New Zealand, Application No. 562919, Examination Report, Sep. 17, 2009 (4 pages).
Office Action (final) U.S. Appl. No. 12/498,782 mailed May 31, 2011 (35 pages).
Office Action dated Nov. 8, 2011 for Japanese Patent Appln. No. 2008-511287 with English translation (11 pgs.).
Office Action—JP Patent Appl. No. 2008-547407 mailed Aug. 21, 2012 (7 pages).
Search Report, Taiwan Application No. 117382 dated Mar. 7, 2012 (English Translation 1 page—Taiwan Search Report 4 pages).
Office Action (non-final) Mexico Application No. MX/1/2007/013977 as communicated to undersigned representative on Nov. 18, 2011 (2 pages).
Office Action—JP Patent Appl. No. 2009-529341 mailed Oct. 16, 2012 (3 pages).
Office Action—JP Patent Appl. No. 2009-529343 mailed Oct. 16, 2012 (4 pages).
Extended European Search Report in EP Application No. 12178315.3, dated Jan. 18, 2013, 8 pages.
Costa Rican Office Action in CR Application No. 9485, Feb. 11, 2013, 14 pages (with English translation).
Office Action in Chinese Application No. 201210562826.8, mailed Mar. 18, 2014, 12 pages.
Extended European Search Report in EP Application No. 14175271.1, dated Dec. 12, 2014, 12 pages.
International Search Report and Written Opinion in International Application No. PCT/US2014/064531, mailed Feb. 11, 2015, 14 pages.

\* cited by examiner

PROCESS FOR THE SYNTHESIS OF AN INDOLEAMINE 2,3-DIOXYGENASE INHIBITOR

This application claims the benefit of priority of U.S. Prov. Appl. No. 61/901,689, filed Nov. 8, 2013, which is incorporated herein by reference in its entirety.

FIELD OF THE INVENTION

The present application relates to processes and intermediates for making 4-({2-[(aminosulfonyl)amino]ethyl}amino)-N-(3-bromo-4-fluorophenyl)-N'-hydroxy-1,2,5-oxadiazole-3-carboximidamide, which is an inhibitor of indoleamine 2,3-dioxygenase useful in the treatment of cancer and other disorders.

BACKGROUND OF THE INVENTION

Tryptophan (Trp) is an essential amino acid required for the biosynthesis of proteins, niacin and the neurotransmitter 5-hydroxytryptamine (serotonin). The enzyme indoleamine 2,3-dioxygenase (also known as INDO or IDO) catalyzes the first and rate limiting step in the degradation of L-tryptophan to N-formyl-kynurenine. In human cells, a depletion of Trp resulting from IDO activity is a prominent gamma interferon (IFN-γ)-inducible antimicrobial effector mechanism. IFN-γ stimulation induces activation of IDO, which leads to a depletion of Trp, thereby arresting the growth of Trp-dependent intracellular pathogens such as *Toxoplasma gondii* and *Chlamydia trachomatis*. IDO activity also has an antiproliferative effect on many tumor cells, and IDO induction has been observed in vivo during rejection of allogeneic tumors, indicating a possible role for this enzyme in the tumor rejection process (Daubener, et al., 1999, *Adv. Exp. Med. Biol.*, 467: 517-24; Taylor, et al., 1991, *FASEB J.*, 5: 2516-22).

It has been observed that HeLa cells co-cultured with peripheral blood lymphocytes (PBLs) acquire an immuno-inhibitory phenotype through up-regulation of IDO activity. A reduction in PBL proliferation upon treatment with interleukin-2 (IL2) was believed to result from IDO released by the tumor cells in response to IFNG secretion by the PBLs. This effect was reversed by treatment with 1-methyl-tryptophan (1MT), a specific IDO inhibitor. It was proposed that IDO activity in tumor cells may serve to impair antitumor responses (Logan, et al., 2002, *Immunology*, 105: 478-87).

Recently, an immunoregulatory role of Trp depletion has received much attention. Several lines of evidence suggest that IDO is involved in induction of immune tolerance. Studies of mammalian pregnancy, tumor resistance, chronic infections and autoimmune diseases have shown that cells expressing IDO can suppress T-cell responses and promote tolerance. Accelerated Trp catabolism has been observed in diseases and disorders associated with cellular immune activation, such as infection, malignancy, autoimmune diseases and AIDS, as well as during pregnancy. For example, increased levels of IFNs and elevated levels of urinary Trp metabolites have been observed in autoimmune diseases; it has been postulated that systemic or local depletion of Trp occurring in autoimmune diseases may relate to the degeneration and wasting symptoms of these diseases. In support of this hypothesis, high levels of IDO were observed in cells isolated from the synovia of arthritic joints. IFNs are also elevated in human immunodeficiency virus (HIV) patients and increasing IFN levels are associated with a worsening prognosis. Thus, it was proposed that IDO is induced chronically by HIV infection, and is further increased by opportunistic infections, and that the chronic loss of Trp initiates mechanisms responsible for cachexia, dementia and diarrhea and possibly immunosuppression of AIDS patients (Brown, et al., 1991, *Adv. Exp. Med. Biol.*, 294: 425-35). To this end, it has recently been shown that IDO inhibition can enhance the levels of virus-specific T cells and, concomitantly, reduce the number of virally-infected macrophages in a mouse model of HIV (Portula et al., 2005, *Blood*, 106: 2382-90).

IDO is believed to play a role in the immunosuppressive processes that prevent fetal rejection in utero. More than 40 years ago, it was observed that, during pregnancy, the genetically disparate mammalian conceptus survives in spite of what would be predicted by tissue transplantation immunology (Medawar, 1953, *Symp. Soc. Exp. Biol.* 7: 320-38). Anatomic separation of mother and fetus and antigenic immaturity of the fetus cannot fully explain fetal allograft survival. Recent attention has focused on immunologic tolerance of the mother. Because IDO is expressed by human syncytiotrophoblast cells and systemic tryptophan concentration falls during normal pregnancy, it was hypothesized that IDO expression at the maternal-fetal interface is necessary to prevent immunologic rejection of the fetal allografts. To test this hypothesis, pregnant mice (carrying syngeneic or allogeneic fetuses) were exposed to 1MT, and a rapid, T cell-induced rejection of all allogeneic concepti was observed. Thus, by catabolizing tryptophan, the mammalian conceptus appears to suppresses T-cell activity and defends itself against rejection, and blocking tryptophan catabolism during murine pregnancy allows maternal T cells to provoke fetal allograft rejection (Munn, et al., 1998, *Science*, 281: 1191-3).

Further evidence for a tumoral immune resistance mechanism based on tryptophan degradation by IDO comes from the observation that most human tumors constitutively express IDO, and that expression of IDO by immunogenic mouse tumor cells prevents their rejection by preimmunized mice. This effect is accompanied by a lack of accumulation of specific T cells at the tumor site and can be partly reverted by systemic treatment of mice with an inhibitor of IDO, in the absence of noticeable toxicity. Thus, it was suggested that the efficacy of therapeutic vaccination of cancer patients might be improved by concomitant administration of an IDO inhibitor (Uyttenhove et al., 2003, *Nature Med.*, 9: 1269-74). It has also been shown that the IDO inhibitor, 1-MT, can synergize with chemotherapeutic agents to reduce tumor growth in mice, suggesting that IDO inhibition may also enhance the anti-tumor activity of conventional cytotoxic therapies (Muller et al., 2005, *Nature Med.*, 11: 312-9).

One mechanism contributing to immunologic unresponsiveness toward tumors may be presentation of tumor antigens by tolerogenic host APCs. A subset of human IDO-expressing antigen-presenting cells (APCs) that coexpressed CD123 (IL3RA) and CCR6 and inhibited T-cell proliferation have also been described. Both mature and immature CD123-positive dendritic cells suppressed T-cell activity, and this IDO suppressive activity was blocked by 1MT (Munn, et al., 2002, *Science*, 297: 1867-70). It has also been demonstrated that mouse tumor-draining lymph nodes (TDLNs) contain a subset of plasmacytoid dendritic cells (pDCs) that constitutively express immunosuppressive levels of IDO. Despite comprising only 0.5% of lymph node cells, in vitro, these pDCs potently suppressed T cell responses to antigens presented by the pDCs themselves and also, in a dominant fashion, suppressed T cell responses to third-party antigens presented by nonsuppressive APCs. Within the population of pDCs, the majority of the functional IDO-mediated suppressor activity segregated with a novel subset of pDCs coexpressing the B-lineage marker CD19. Thus, it was hypothesized that IDO-mediated suppression by pDCs in TDLNs creates a local microenvironment that is potently suppressive of host antitumor T cell responses (Munn, et al., 2004, *J. Clin. Invest.*, 114(2): 280-90).

IDO degrades the indole moiety of tryptophan, serotonin and melatonin, and initiates the production of neuroactive and immunoregulatory metabolites, collectively known as kynurenines. By locally depleting tryptophan and increasing proapoptotic kynurenines, IDO expressed by dendritic cells (DCs) can greatly affect T-cell proliferation and survival. IDO induction in DCs could be a common mechanism of deletional tolerance driven by regulatory T cells. Because such tolerogenic responses can be expected to operate in a variety of physiopathological conditions, tryptophan metabolism and kynurenine production might represent a crucial interface between the immune and nervous systems (Grohmann, et al., 2003, *Trends Immunol.*, 24: 242-8). In states of persistent immune activation, availability of free serum Trp is diminished and, as a consequence of reduced serotonin production, serotonergic functions may also be affected (Wirleitner, et al., 2003, *Curr. Med. Chem.*, 10: 1581-91).

Interestingly, administration of interferon-α has been observed to induce neuropsychiatric side effects, such as depressive symptoms and changes in cognitive function. Direct influence on serotonergic neurotransmission may contribute to these side effects. In addition, because IDO activation leads to reduced levels of tryptophan, the precursor of serotonin (5-HT), IDO may play a role in these neuropsychiatric side effects by reducing central 5-HT synthesis. Furthermore, kynurenine metabolites such as 3-hydroxy-kynurenine (3-OH—KYN) and quinolinic acid (QUIN) have toxic effects on brain function. 3-OH—KYN is able to produce oxidative stress by increasing the production of reactive oxygen species (ROS), and QUIN may produce overstimulation of hippocampal N-methyl-D-aspartate (NMDA) receptors, which leads to apoptosis and hippocampal atrophy. Both ROS overproduction and hippocampal atrophy caused by NMDA overstimulation have been associated with depression (Wichers and Maes, 2004, *J. Psychiatry Neurosci.*, 29: 11-17). Thus, IDO activity may play a role in depression.

Small molecule inhibitors of IDO are being developed to treat or prevent IDO-related diseases such as those described above. For example, oxadiazole and other heterocyclic IDO inhibitors are reported in US 2006/0258719 and US 2007/0185165. PCT Publication WO 99/29310 reports methods for altering T cell-mediated immunity comprising altering local extracellular concentrations of tryptophan and tryptophan metabolites, using an inhibitor of IDO such as 1-methyl-DL-tryptophan, p-(3-benzofuranyl)-DL-alanine, p-[3-benzo(b)thienyl]-DL-alanine, and 6-nitro-L-tryptophan) (Munn, 1999). Reported in WO 03/087347, also published as European Patent 1501918, are methods of making antigen-presenting cells for enhancing or reducing T cell tolerance (Munn, 2003). Compounds having indoleamine-2,3-dioxygenase (IDO) inhibitory activity are further reported in WO 2004/094409; and U.S. Patent Application Publication No. 2004/0234623 is directed to methods of treating a subject with a cancer or an infection by the administration of an inhibitor of indoleamine-2,3-dioxygenase in combination with other therapeutic modalities.

In light of the experimental data indicating a role for IDO in immunosuppression, tumor resistance and/or rejection, chronic infections, HIV-infection, AIDS (including its manifestations such as cachexia, dementia and diarrhea), autoimmune diseases or disorders (such as rheumatoid arthritis), and immunologic tolerance and prevention of fetal rejection in utero, therapeutic agents aimed at suppression of tryptophan degradation by inhibiting IDO activity are desirable. Inhibitors of IDO can be used to activate T cells and therefore enhance T cell activation when the T cells are suppressed by pregnancy, malignancy or a virus such as HIV. Inhibition of IDO may also be an important treatment strategy for patients with neurological or neuropsychiatric diseases or disorders such as depression.

Due to the usefulness of IDO inhibitors, there is a need for development of new processes for making IDO inhibitors. This application is directed towards this need and others.

SUMMARY OF THE INVENTION

The compound 4-({2-[(aminosulfonyl)amino]ethyl}amino)-N-(3-bromo-4-fluorophenyl)-N'-hydroxy-1,2,5-oxadiazole-3-carboximidamide having Formula I:

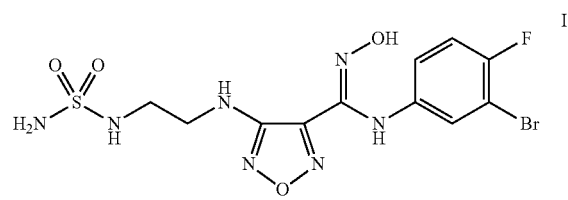 [SMILES: NS(=O)(=O)NCCNc1nonc1/C(=N/O)Nc1ccc(F)c(Br)c1]

is an inhibitor of the enzyme indoleamine 2,3-dioxygenase (also known as IDO). The compound of Formula I, as well as its preparation and use, has been described in U.S. Pat. No. 8,088,803, which is incorporated herein by reference in its entirety. The intermediates and processes provided herein help satisfy the ongoing need for the development of IDO inhibitors for the treatment of serious diseases.

The present application provides, inter alia, intermediates and processes for preparing a compound of Formula I:

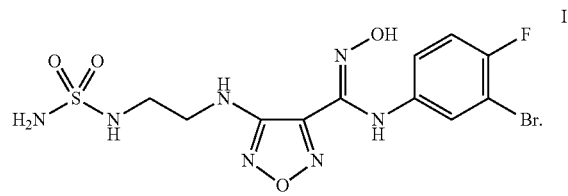 [SMILES: NS(=O)(=O)NCCNc1nonc1/C(=N/O)Nc1ccc(F)c(Br)c1]

Accordingly, the present application provides a process comprising reacting a compound of Formula F5:

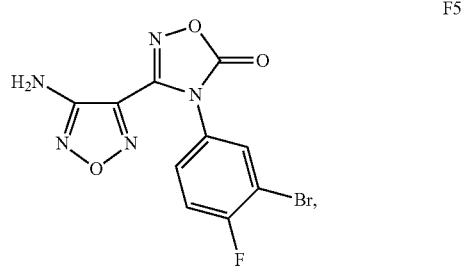 [SMILES: Nc1nonc1-c1noc(=O)n1-c1ccc(F)c(Br)c1]

with an aldehyde of Formula F6:

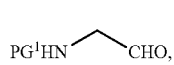

to afford a compound of Formula F7:

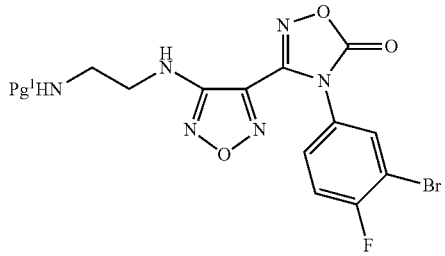

wherein Pg¹ is defined infra.

The present application further provides a process comprising reacting a compound of Formula F15:

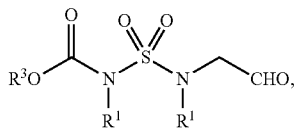

with a compound of Formula F5 to afford a compound of Formula F16:

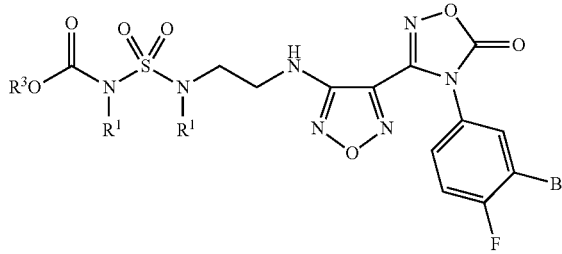

wherein $R^1$ and $R^3$ are defined infra.

The present application further provides a process comprising reacting a compound of Formula F17:

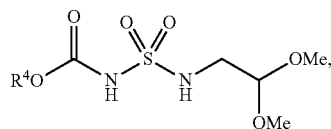

with a compound of Formula F5 to afford a compound of Formula F18:

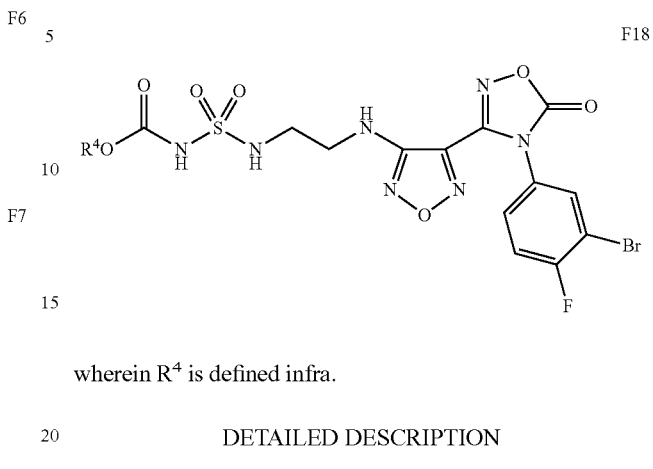

wherein $R^4$ is defined infra.

DETAILED DESCRIPTION

While certain of the processes steps are illustrated in the Schemes shown below, it is intended that the individual process steps may be claimed individually or in any combination (e.g., in Scheme I, steps E, F, G, H, and I may be claimed individually or in combination). It is not intended that the processes be limited to an overall process having each and every step in the Schemes below.

Accordingly, general scheme for the preparation of the compound of Formula I is described in Scheme 1.

Scheme 1

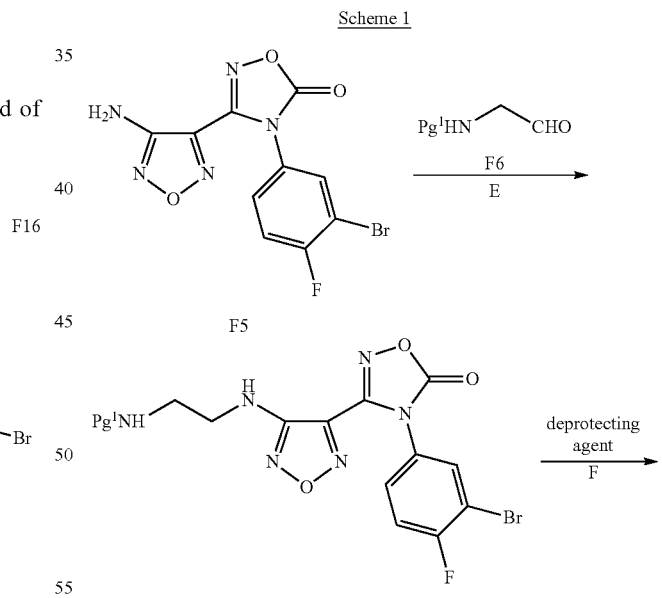

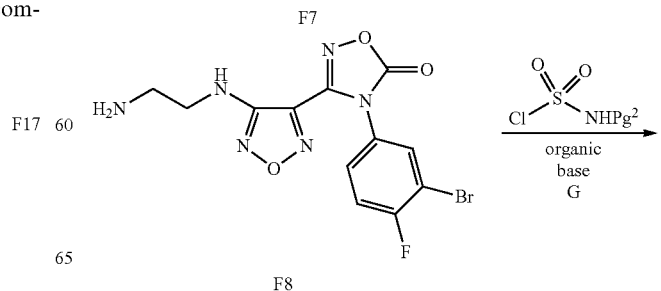

-continued

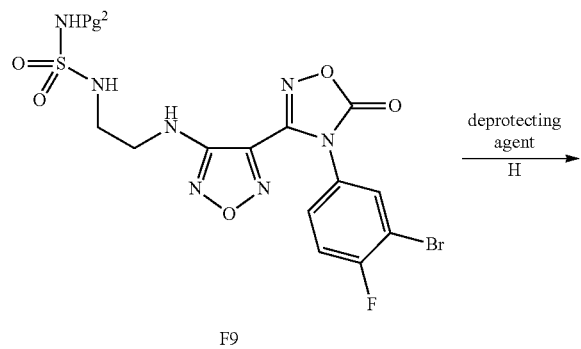

F9

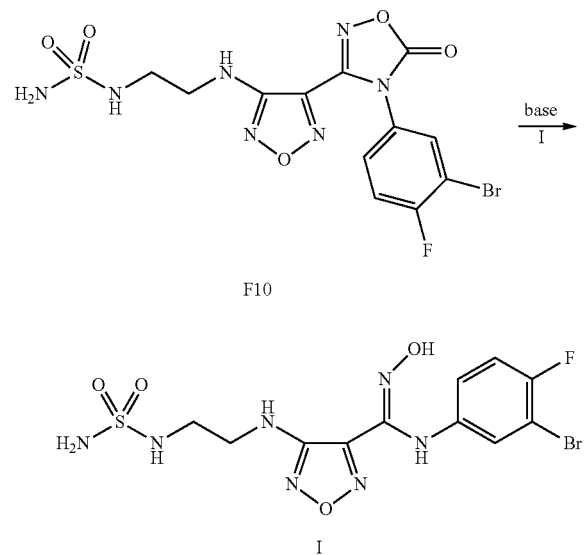

F10

I

Accordingly, the present application provides a process comprising reacting a compound of Formula F5:

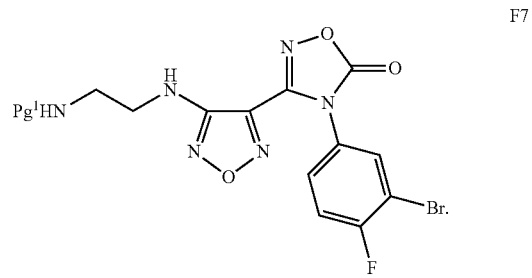

F5 with an aldehyde of Formula F6:

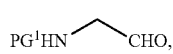

F6 wherein $Pg^1$ is an amino protecting group, to afford a compound of Formula F7:

F7

Amino protecting groups $Pg^1$ may be used to prevent unwanted reactions of an amino group while performing a desired transformation. Amino protecting groups allow easy covalent attachment to a nitrogen atom as well as selective cleavage from the nitrogen atom. Suitable "amino protecting groups", such as alkoxycarbonyl (such as ethoxycarbonyl, tert-butoxycarbonyl (Boc), benzyloxycarbonyl (Cbz), 9-fluorenylmethyloxycarbonyl (Fmoc), and the like), acyl (such as acetyl (Ac), benzoyl (Bz), and the like), sulfonyl (such as methanesulfonyl, trifluoromethanesulfonyl, and the like), arylalkyl (such as benzyl, 4-methoxybenzyl, diphenylmethyl, triphenylmethyl (trityl), and the like), alkenylalkyl (such as allyl, prenyl, and the like), diarylmethyleneyl (such as $(C_6H_5)_2C=N$, and the like), and silyl (such as tert-butyldimethylsilyl, triisopropylsilyl, and the like), are known to one skilled in the art. The chemistry of amino protecting groups can be found in Wuts and Greene, *Greene's Protective Groups in Organic Synthesis*, $4^{th}$ Ed., pp 696-926, John Wiley & Sons: New York, 2006, which is incorporated herein by reference in its entirety.

In some embodiments, $Pg^1$ is ethoxycarbonyl, tert-butoxycarbonyl, benzyloxycarbonyl, or 9-fluorenylmethyloxycarbonyl.

In some embodiments, $Pg^1$ is $C_{1-6}$ alkoxycarbonyl.

In some embodiments, $Pg^1$ is tert-butoxycarbonyl.

Appropriate solvents for Step E include, but are not limited to, methanol or tetrahydrofuran (THF), acetonitrile and the like. Halogenated hydrocarbon solvents (i.e., halogenated alkanes, such as dichloromethane, chloroform, dichloroethane or tetrachloroethane) can also be used.

In some embodiments, said reacting is performed in a solvent component comprising tetrahydrofuran. As used herein, a solvent component may refer to one solvent or a mixture of solvents. In some embodiments, the solvent component is an organic solvent. In some embodiments, said reacting is performed in a solvent component comprising a halogenated hydrocarbon solvent. In some embodiments, said halogenated hydrocarbon solvent is dichloromethane.

In some embodiments, said reacting is performed in a solvent component comprising acetonitrile.

In some embodiments, said reacting is performed in a solvent component comprising dichloromethane and acetonitrile.

In some embodiments, said reacting is performed in the presence of a reducing agent.

The reducing agent can be any compound capable of reducing an organic compound to a lower oxidation state. Reduction usually involves addition of hydrogen atoms or removal of oxygen atoms from a group. For example, aldehydes such as F6 can be reduced in the presence of an amine of Formula F5 (Step E, Scheme 1) by the addition of hydrogen, either in the form of hydrogen gas (H$_2$) or using a hydride reagent (such as NaB(OAc)$_3$H, NaBH$_4$, LiAlH$_4$, and the like); using triphenylphosphine; or using a combination of sodium iodide, chlorotrimethylsilane, and methanol. In some embodiments, this step can be performed under acidic conditions in the presence of an acid (such as trifluoroacetic acid). In some embodiments, this step can be performed at a temperature from about −15° C. to about 30° C., e.g., from about −15° C. to about 0° C., from about −5° C. to about 5° C., from about −5° C. to about 0° C., or from about 0° C. to about 45° C.

In some embodiments, said reducing agent is a borohydride reducing agent (e.g., NaB(OAc)$_3$H, NaBH$_4$, or other boron containing hydride reducing agent).

In some embodiments, said borohydride reducing agent is sodium triacetoxyborohydride.

In some embodiments, said reacting is performed in the presence of trifluoroacetic acid.

In some embodiments, the process further comprises deprotecting said compound of Formula F7 to afford a compound of Formula F8:

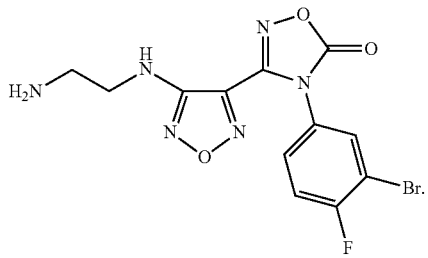

Amino deprotecting agents useful for this Step F are known to those skilled in the art, such as those in Wuts and Greene (supra). In particular, the amino protecting groups described above can be conveniently removed using many available amino deprotecting agents that are specific to the various groups mentioned above without affecting other desired portions of the compound. The tert-butoxycarbonyl group can be removed (e.g., hydrolyzed) from the nitrogen atom, for example, by treatment with an acid (such as hydrochloric acid, trifluoroacetic acid, toluenesulfonic acid, and the like); a combination of reagents (e.g., mixture of acetyl chloride and methanol) known to generate an acid; or a Lewis acid (e.g., BF$_3$·Et$_2$O). The benzyloxycarbonyl group can be removed (e.g., hydrogenolyzed) from the nitrogen atom, for example, by treatment with hydrogen and a catalyst (such as palladium on carbon).

In some embodiments, the amino deprotecting agent is trifluoroacetic acid. In some embodiments, the amino deprotecting agent contains trifluoroacetic acid and >0.5% by volume of water, e.g., >1.0% by volume of water, >1.5% by volume of water, >2.0% by volume of water, from about 2% to about 10% by volume of water, from about 10% to about 20% by volume of water, or from about 20% to about 50% by volume of water. In some embodiments, the amino deprotecting agent can be a mixture of trifluoroacetic acid and water in a volumetric ratio of about 98:2. In some embodiments, the amino deprotecting agent can be hydrochloric acid, optionally in a solvent (e.g., water, THF, dioxane, ethyl acetate, etc.). In some embodiments, the solvent component is ethyl acetate. In some embodiments, the amino deprotecting agent can be hydrochloric acid optionally in a solvent such as an alcohol (such as isopropanol, methanol or ethanol). Halogenated hydrocarbon solvents (e.g., dichloromethane, chloroform, dichloroethane or tetrachloroethane) can also be used. In some embodiments, the molar ratio of hydrochloric acid and the compound of Formula F7 is about 6.0, about 5.0, about 4.0, about 3.0 about 2.0, about 1.0, or about 1.1. In some embodiments, Step F can be performed at a temperature from about −10° C. to about 60° C., e.g., from about −10° C. to about 0° C., from about 0° C. to about 25° C., from about 25° C. to about 45° C., or from about 45° C. to about 60° C.

In some embodiments, said deprotecting comprises reacting the compound of Formula F7 with hydrochloric acid.

In some embodiments, said deprotecting comprises reacting the compound of Formula F7 with hydrochloric acid in a solvent component comprising isopropanol.

In some embodiments, said deprotecting comprises reacting the compound of Formula F7 with hydrochloric acid in a solvent component comprising a halogenated hydrocarbon solvent.

In some embodiments, said halogenated hydrocarbon solvent is dichloromethane.

In some embodiments, the invention further comprises reacting said compound of Formula F8, with Pg$^2$-NH—SO$_2$—X, in the presence of an organic base to afford a compound of Formula F9:

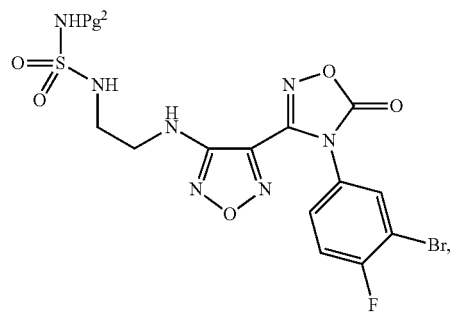

wherein:
Pg$^2$ is an amino protecting group; and
X is halo.

In some embodiments, Pg$^2$-NH—SO$_2$Cl can be prepared and immediately used in the reaction with the compound of Formula F8. The protecting group Pg$^2$ could be selected from any of the protecting groups known in the art for protecting amines or sulfonamides (such as those described above for Pg$^1$). In some embodiments, Pg$^2$ can be an alkoxycarbonyl group (such as tert-butoxycarbonyl).

Appropriate solvents include, but are not limited to, halogenated hydrocarbon solvents such as dichloromethane and the like. The organic base can be any base that serves to neutralize the HCl generated during the reaction of the compound of Formula F8 and the protected amino-sulfonyl chloride. The organic base can include acyclic tertiary amines such as tri(C$_{1-6}$)alkylamine (e.g., triethylamine, diisopropylethylamine (DIPEA) and the like), cyclic tertiary amines (e.g., N-methyl piperidine, 1,4-diazabicyclo[2.2.2]octane (DABCO) and the like). In some embodiments, the organic base can be triethylamine. In some embodiments, this step can be performed at a temperature from about −15° C. to about 60° C., e.g., from about −15° C. to about 0° C., from about 0° C. to about 25° C., from about 25° C. to about 45° C., or from about 45° C. to about 60° C.

In such embodiments, the Pg²-NH—SO₂Cl can be obtained by the reaction of an alcohol (such as, ethanol, tert-butyl alcohol and the like) with chlorosulfonyl isocyanate (ClS(O)₂NCO).

In some embodiments, Pg² is ethoxycarbonyl, tert-butoxycarbonyl, benzyloxycarbonyl, or 9-fluorenylmethyloxycarbonyl.

In some embodiments, Pg² is $C_{1-6}$ alkoxycarbonyl.

In some embodiments, Pg² is tert-butoxycarbonyl.

In some embodiments, said reacting is performed in a solvent component comprising a halogenated hydrocarbon solvent.

In some embodiments, said halogenated hydrocarbon solvent is dichloromethane.

In some embodiments, said organic base comprises a tri ($C_{1-6}$)alkylamine.

In some embodiments, said organic base is triethylamine.

In some embodiments, X is chloro.

In some embodiments, the invention further comprises deprotecting said compound of Formula F9 to afford a compound of Formula F10:

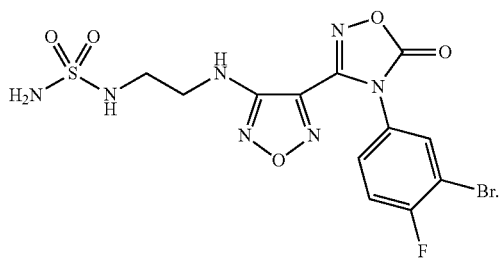

F10

In some embodiments, suitable deprotecting agents may include those described above for deprotecting the compound of Formula F7.

In some embodiments, said deprotecting comprises reacting a compound of Formula F9 with hydrochloric acid. In some embodiments, said deprotecting comprises reacting a compound of Formula F9 with hydrochloric acid in a solvent component comprising an alcohol. In some embodiments, said alcohol is ethanol. In some embodiments, said deprotecting comprises reacting a compound of Formula F9 with hydrochloric acid in a solvent component comprising ethyl acetate.

In some embodiments, the invention further comprises reacting said compound of Formula F10 with a base to afford a compound of Formula I:

A base can be used for the conversion (e.g., hydrolysis) of the oxadiazolone ring in F10 to reveal the amidoxime in the compound of Formula I, optionally in a solvent (Step I, Scheme 1). The protection of the amidoxime as the oxadiazolone can be useful to prevent adverse reactions of the hydroxyl group or that of the amidoxime as a whole. The base can be either an inorganic base such as alkali metal hydroxide (e.g., NaOH, LiOH, KOH, Mg(OH)₂, etc.); or an organic base such as an acyclic amine (e.g., triethylamine, diisopropylethylamine (DIPEA), etc.) or a cyclic amine (e.g., pyrrolidine, piperidine, etc). The base can be made available in the form of a resin (such as Amberlite® and the like). In some further embodiments, the base can be provided in the form of a solution in water (e.g., about 0.5 N solution, about 1 N solution, about 1.5 N solution, about 2.5 N solution, from about 3 N to about 5 N solution, from about 5 N to about 10 N solution). In some embodiments, the base is an alkali metal hydroxide (such as, sodium hydroxide). In some embodiments, the base can be 2 N NaOH solution in water. In some embodiments, the solvent can be ethanol or tetrahydrofuran (THF). In some embodiments, the solvent can be a mixture of ethanol and water. In some embodiments, the reacting of the compound of Formula F10 with a base to afford the compound of Formula I can be performed at a temperature from about –10° C. to about 60° C., e.g., from about –10° C. to about 20° C., from about 0° C. to about 30° C., from about 0° C. to about 10° C., or from about 0° C. to about 5° C.

In some embodiments, said base comprises an alkali metal hydroxide.

In some embodiments, said alkali metal hydroxide is sodium hydroxide.

In some embodiments, said reacting is performed in a solvent component comprising tetrahydrofuran, water and ethanol.

In some embodiments, the compound of Formula F5, can be obtained in a sequence of steps shown in Scheme 2. The preparation of the intermediate, 4-amino-N-hydroxy-1,2,5-oxadiazole-3-carboximidamide F2, has been described in *J. Heterocycl. Chem.* (1965), 2, 253, which is incorporated herein by reference in its entirety, and its conversion to the chloro oxime F3 has been described in *Synth. Commun.* (1988), 18, 1427, which is incorporated herein by reference in its entirety. In some embodiments, the chloro oxime of Formula F3 can be coupled to 3-bromo-4-fluoroaniline, optionally in a solvent (such as water), followed by addition of sodium bicarbonate, to provide an amidoxime of Formula F4. The amidooxime functionality of the compound of F4 can then be converted to an oxadiazolone or Formula F5 using N,N-carbonyldiimidazole (DCI) in a solvent (such as ethyl acetate, dioxane, THF and the like), at elevated temperatures such as about 50° C., about 60° C., about 70° C., about 80° C., about 90° C., or about 100° C.

Scheme 2

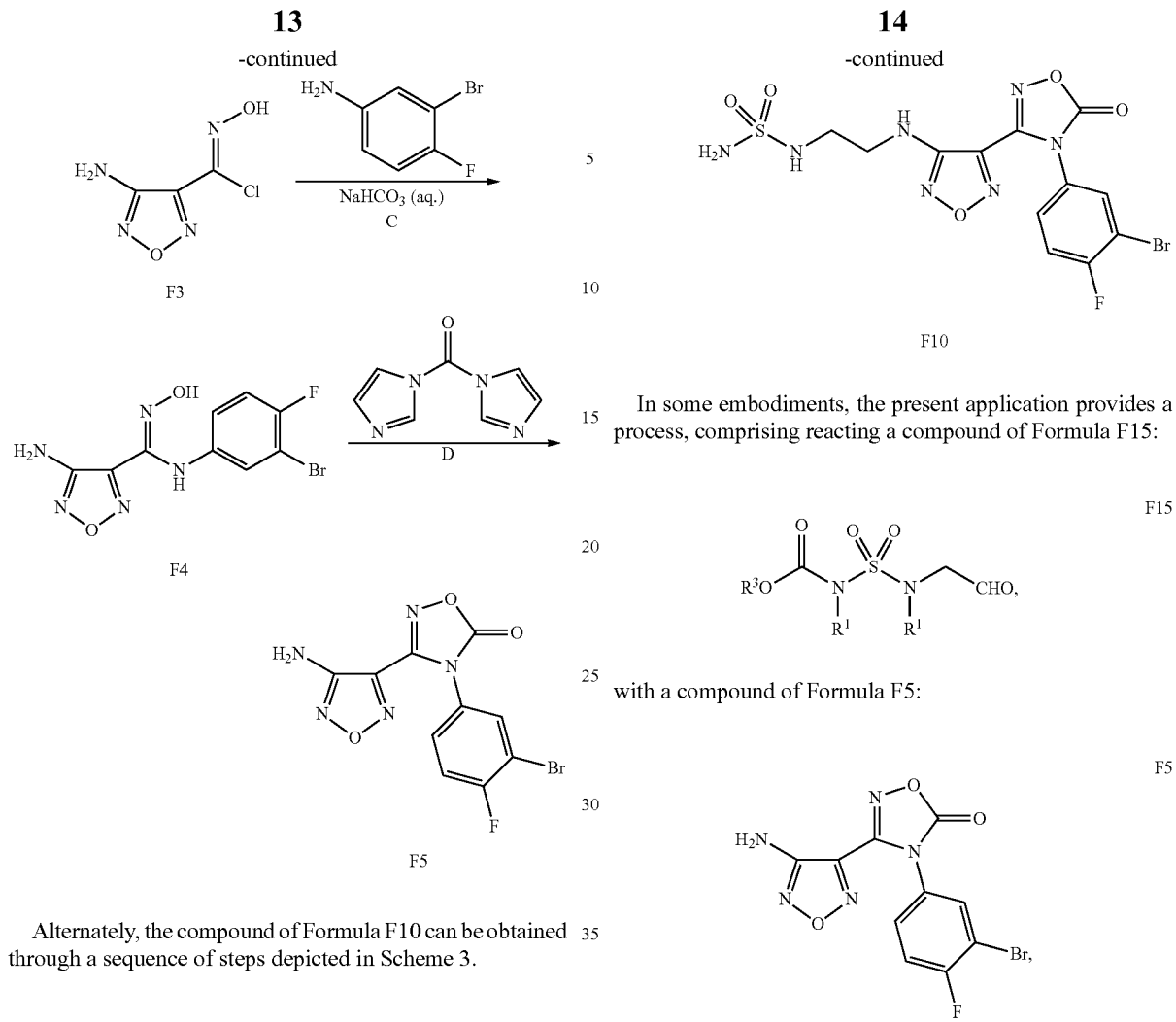

Alternately, the compound of Formula F10 can be obtained through a sequence of steps depicted in Scheme 3.

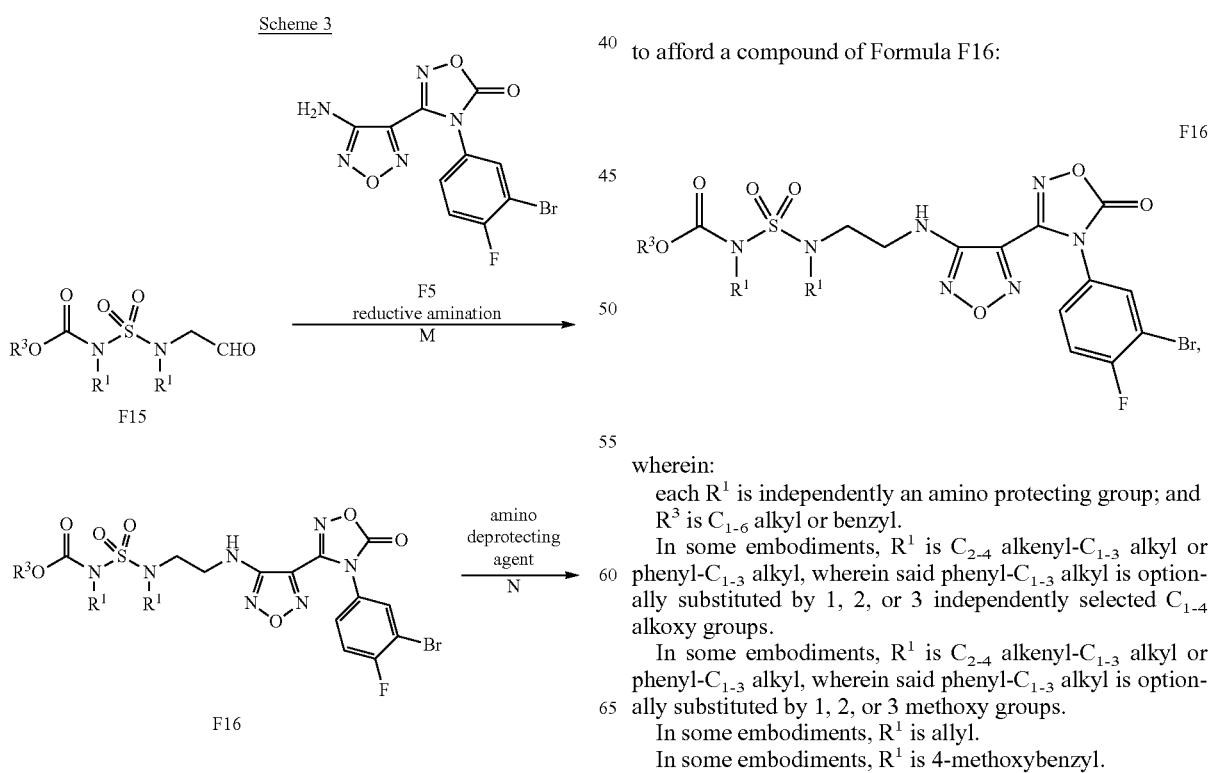

In some embodiments, the present application provides a process, comprising reacting a compound of Formula F15:

with a compound of Formula F5:

to afford a compound of Formula F16:

wherein:
each $R^1$ is independently an amino protecting group; and
$R^3$ is $C_{1-6}$ alkyl or benzyl.
In some embodiments, $R^1$ is $C_{2-4}$ alkenyl-$C_{1-3}$ alkyl or phenyl-$C_{1-3}$ alkyl, wherein said phenyl-$C_{1-3}$ alkyl is optionally substituted by 1, 2, or 3 independently selected $C_{1-4}$ alkoxy groups.
In some embodiments, $R^1$ is $C_{2-4}$ alkenyl-$C_{1-3}$ alkyl or phenyl-$C_{1-3}$ alkyl, wherein said phenyl-$C_{1-3}$ alkyl is optionally substituted by 1, 2, or 3 methoxy groups.
In some embodiments, $R^1$ is allyl.
In some embodiments, $R^1$ is 4-methoxybenzyl.

In some embodiments, $R^3$ is $C_{1-6}$ alkyl.
In some embodiments, $R^3$ is tert-butyl.
In some embodiments, $R^3$ is $C_{1-4}$ alkyl.
In some embodiments, $R^3$ is butyl.

Preferably, the reacting is performed in the presence of a reducing agent. The reducing agent can be any compound capable of reducing an organic compound to a lower oxidation state. In some embodiments, the reducing agent can be hydrogen gas in the presence of a catalyst or a hydride reagent (such as $NaB(OAc)_3H$, $NaBH_4$, $LiAlH_4$ and the like); using triphenylphosphine; or using a combination of sodium iodide, chlorotrimethylsilane, and methanol. In some embodiments, this step can be performed in the presence of an acid such as trifluoroacetic acid. Suitable solvents for this step include isopropyl alcohol, THF, dioxane, or the like. In some embodiments, this step can be performed at a temperature from about −15° C. to about 30° C., e.g., from about −15° C. to about 0° C., from about −5° C. to about 5° C., from about −5° C. to about 0° C., from about 0 to 5° C., or from about 0° C. to about 45° C.

In some embodiments, said reacting is performed in a solvent component comprising tetrahydrofuran.

In some embodiments, said reacting is performed in the presence of a reducing agent.

In some embodiments, said reducing agent is a borohydride reducing agent.

In some embodiments, said borohydride reducing agent is sodium triacetoxyborohydride.

In some embodiments, said reacting is performed in the presence of trifluoroacetic acid.

In some embodiments, the invention further comprises deprotecting said compound of Formula F16 to afford a compound of Formula F10:

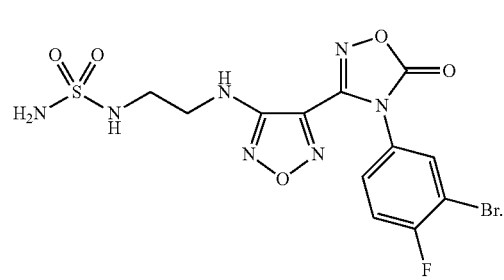

F10

Treatment of a compound F16 to replace RN with $NH_2$ can be accomplished by methods for the deprotection of particular amine protecting groups known to one skilled in the art, such as those in Wuts and Greene, *Greene's Protective Groups in Organic Synthesis*, 4th Ed., pp 696-926, John Wiley & Sons: New York, 2006. In some embodiments, when $R^1$ is allyl, the deprotecting agent can be a palladium catalyst (e.g., $Pd(Ph_3P)_4$, Pd/C, or Pd(dba)DPPB). In some embodiments, when the $R^1$ is 4-methoxybenzyl, the deprotecting agent can include an organic acid (such as trifluoroacetic acid or methanesulfonic acid, and the like); an inorganic acid (such as hydrochloric acid); hydrogen and palladium; or sodium in liquid ammonia. The deprotecting can be performed at a temperature from about 30° C. to about 90° C., e.g., from about 50° C. to about 100° C., or from about 60° C. to about 80° C.

In some embodiments, said deprotecting comprises reacting a compound of Formula F16 with trifluoroacetic acid.

In some embodiments, said deprotecting comprises reacting a compound of Formula F16 with is hydrochloric acid.

Compound F15 can be made by a three step process (Steps J, K and L) from chlorosulfonylisocyanate, as shown in Scheme 4.

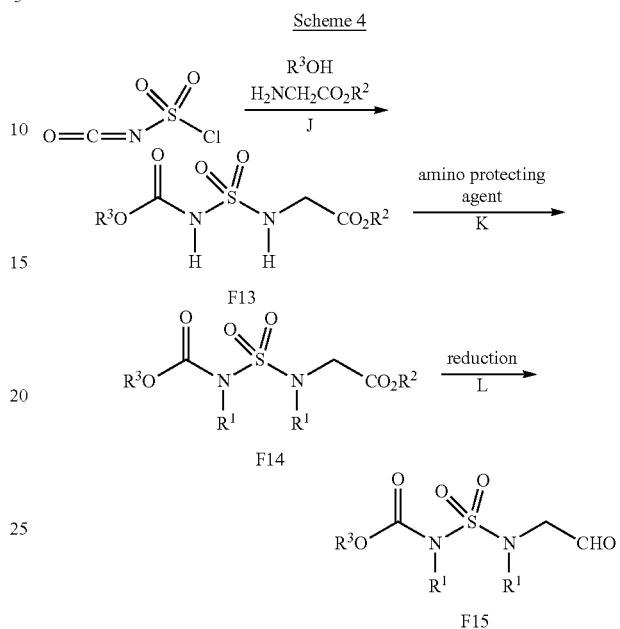

Scheme 4

Accordingly, the present application further provides a process wherein said compound of Formula F15 is obtained by a process comprising treating a compound of Formula F14:

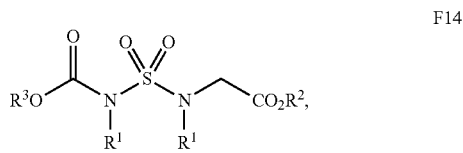

F14 with a reducing agent to afford said compound of Formula F15; wherein $R^2$ is $C_{1-4}$ alkyl; and $R^3$ is defined supra.

In some embodiments, $R^2$ is methyl.

In some embodiments, $R^2$ is ethyl.

In some embodiments, the reducing can be carried out with diisobutylaluminum hydride (DIBAL-H). Suitable solvents include halogenated hydrocarbon solvents such as dichloromethane, chloroform, dichloroethane, tetrachloroethane, and the like. In some embodiments, the reduction can be performed at about room temperature e.g., from about −80° C. to about 30° C., from about −78° C. to about 0° C., from about 0° C. to about 30° C., or from about 25° C. to about 30° C.

In some embodiments, said treating is performed in a halogenated hydrocarbon solvent.

In some embodiments, said halogenated hydrocarbon solvent is dichloromethane.

In some embodiments, said reducing agent is diisobutylaluminum hydride.

In some embodiments, said compound of Formula F14 is obtained by a process comprising protecting a compound of Formula F13:

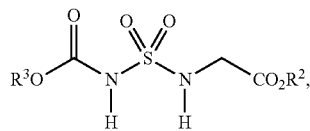

F13 with one or more independently selected amino protecting agents to afford a compound of Formula F14.

Protecting group $R^1$ on F14 can be selected from the various amino protecting groups known in the art (supra). In some embodiments, the amino protecting agent is allyl bromide or 4-methoxybenzyl chloride.

In some embodiments, said one or more amino protecting agents is selected from allyl bromide and 4-methoxybenzyl chloride.

In some embodiments, said protecting is performed in the presence of a base.

In some embodiments, said base is potassium carbonate.

In some embodiments, said protecting is performed in a solvent component comprising acetonitrile.

In some embodiments, the preparation of the compound of F13 can be obtained by treating chlorosulfonylisocyanate with an alcohol $R^3OH$ (where $R^3$ is defined above) and a glycine ester $H_2NCH_2CO_2R^2$, wherein $R^2$ is $C_{1-4}$ alkyl. In some embodiments, this Step J is carried out in the presence of an organic acid (such as acetic acid, benzoic acid, trifluoroacetic acid). Suitable solvents for this step include dichloromethane, chloroform, dichloroethane, tetrachloroethane, and the like.

In some embodiments, the present application provides a compound of Formula F13:

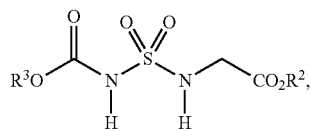

F13 wherein:
$R^2$ is $C_{1-4}$ alkyl; and
$R^3$ is $C_{1-6}$ alkyl or benzyl.
In some embodiments, $R^2$ is methyl.
In some embodiments, $R^2$ is ethyl.
In some embodiments, $R^3$ is $C_{1-6}$ alkyl.
In some embodiments, $R^3$ is tert-butyl.

In some embodiments, the compound of Formula F13 is ethyl-2-((N-(tert-butoxycarbonyl)sulfamoyl)amino)acetate:

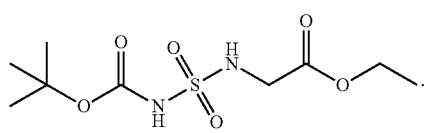 [SMILES: CCOC(=O)CNS(=O)(=O)NC(=O)OC(C)(C)C]

In some embodiments, the invention further provides a compound of Formula F14:

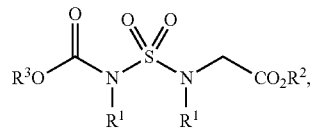

F14 wherein:
each $R^1$ is independently an amino protecting group;
$R^2$ is $C_{1-4}$ alkyl; and
$R^3$ is $C_{1-6}$ alkyl or benzyl.

In some embodiments, $R^1$ is $C_{2-4}$ alkenyl-$C_{1-3}$ alkyl or phenyl-$C_{1-3}$ alkyl, wherein said phenyl-$C_{1-3}$ alkyl is optionally substituted by 1, 2, or 3 independently selected $C_{1-4}$ alkoxy groups.

In some embodiments, $R^1$ is allyl.
In some embodiments, $R^1$ is 4-methoxybenzyl.
In some embodiments, $R^2$ is methyl.
In some embodiments, $R^2$ is ethyl.
In some embodiments, $R^3$ is $C_{1-6}$ alkyl.
In some embodiments, $R^3$ is tert-butyl.
In some embodiments, $R^3$ is $C_{1-4}$ alkyl.
In some embodiments, $R^3$ is butyl.
In some embodiments, $R^3$ is $C_{1-4}$ alkyl.
In some embodiments, $R^3$ is butyl.

In some embodiments, the compound of Formula F14 is ethyl-2-(allyl(N-allyl-N-(tert-butoxycarbonyl)sulfamoyl)amino)acetate:

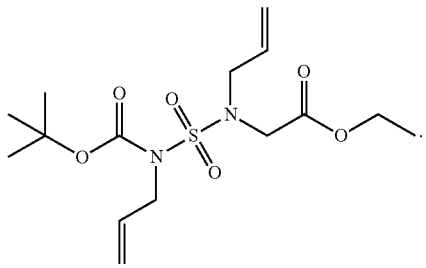 [SMILES: C=CCN(CC(=O)OCC)S(=O)(=O)N(CC=C)C(=O)OC(C)(C)C]

In some embodiments, the compound of Formula F14 is ethyl-2-(4-methoxybenzyl(N-4-methoxybenzyl-N-(tert-butoxycarbonyl) sulfamoyl)amino)acetate:

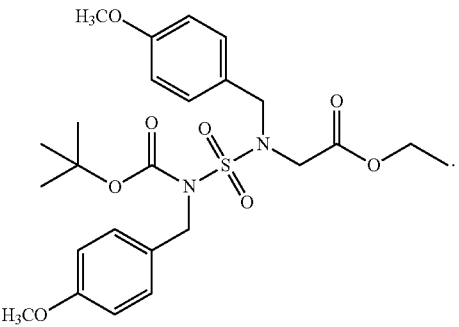 [SMILES: CCOC(=O)CN(Cc1ccc(OC)cc1)S(=O)(=O)N(Cc1ccc(OC)cc1)C(=O)OC(C)(C)C]

In some embodiments, the present application provides a compound of Formula F15:

F15 wherein:

R³ is $C_{1-6}$ alkyl or benzyl; and each R¹ is independently an amino protecting group.

In some embodiments, R¹ is $C_{2-4}$ alkenyl-$C_{1-3}$ alkyl or phenyl-$C_{1-3}$ alkyl, wherein said phenyl-$C_{1-3}$ alkyl is optionally substituted by 1, 2, or 3 independently selected $C_{1-4}$ alkoxy groups.

In some embodiments, R¹ is allyl.

In some embodiments, R¹ is 4-methoxybenzyl.

In some embodiments, R³ is $C_{1-6}$ alkyl.

In some embodiments, R³ is tert-butyl.

In some embodiments, the compound of Formula F15 is tert-butyl allyl {[allyl(2-oxoethyl)amino]sulfonyl}carbamate:

In some embodiments, the compound of Formula F15 is tert-butyl(4-methoxybenzyl) {[(4-methoxybenzyl)(2-oxoethyl)amino]sulfonyl}carbamate:

In some embodiments, the invention provides a compound of Formula F16:

F16 wherein R³ is $C_{1-6}$ alkyl or benzyl and each R¹ is independently an amino protecting group.

In some embodiments, R¹ is $C_{2-4}$ alkenyl-$C_{1-3}$ alkyl or phenyl-$C_{1-3}$ alkyl, wherein said phenyl-$C_{1-3}$ alkyl is optionally substituted by 1, 2, or 3 independently selected $C_{1-4}$ alkoxy groups.

In some embodiments, R¹ is allyl.

In some embodiments, R¹ is 4-methoxybenzyl.

In some embodiments, R³ is $C_{1-6}$ alkyl.

In some embodiments, R³ is tert-butyl.

In some embodiments, R³ is $C_{1-4}$ alkyl.

In some embodiments, R³ is butyl.

In some embodiments, the compound of Formula F16 is tert-butyl allyl(N-allyl-N-(2-(4-(4-(3-bromo-4-fluorophenyl)-5-oxo-4,5-dihydro-1,2,4-oxadiazol-3-yl)-1,2,5-oxadiazol-3-ylamino)ethyl)sulfamoyl)carbamate:

In some embodiments, the compound of Formula F16 is tert-butyl (4-methoxybenzyl)-(N-(4-methoxybenzyl)-N-(2-(4-(4-(3-bromo-4-fluorophenyl)-5-oxo-4,5-dihydro-1,2,4-oxadiazol-3-yl)-1,2,5-oxadiazol-3-ylamino)ethyl)sulfamoyl)carbamate:

Scheme 5 delineates an alternative route for the preparation of the compound of Formula F10.

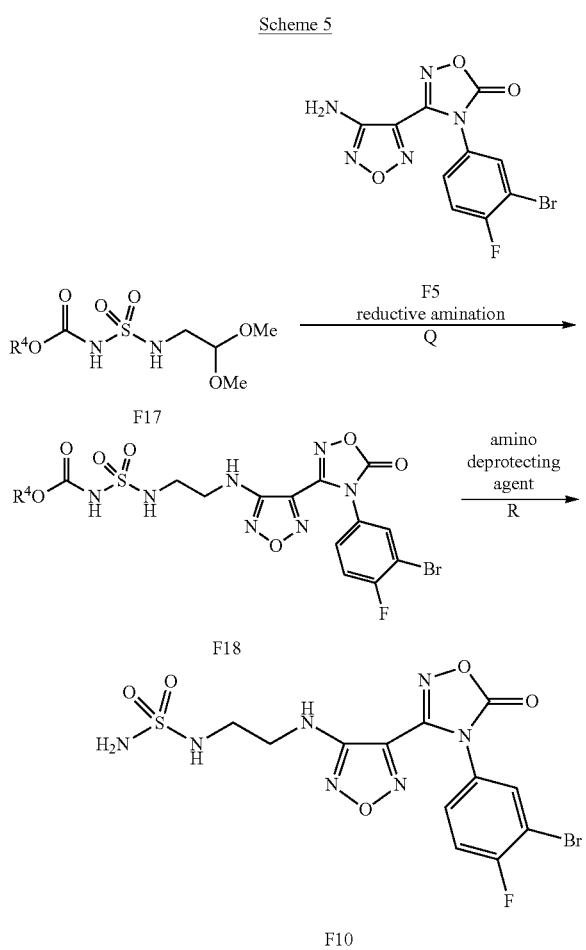

The present application also provides a process comprising reacting a compound of Formula F17:

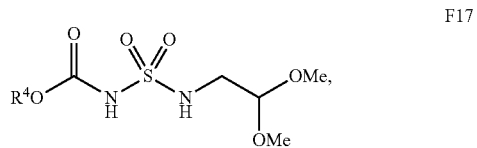

wherein $R^4$ is $C_{1-6}$ alkyl, $C_{1-6}$ haloalkyl, benzyl, or 9H-fluoren-9-ylmethyl with a compound of Formula F5:

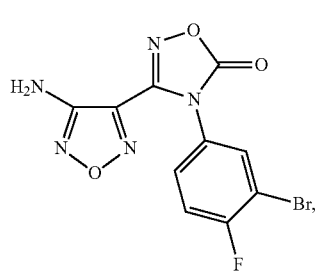

to afford a compound of Formula F18:

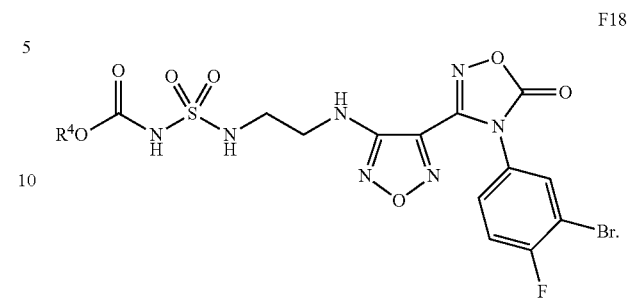

In some embodiments, $R^4$ is tert-butyl.

In some embodiments, $R^4$ is benzyl.

In some embodiments, $R^4$ is ethyl.

In some embodiments, $R^4$ is $C_{1-3}$ haloalkyl.

In some embodiments, $R^4$ is 2,2,2-trichloroethyl.

In some embodiments, $R^4$ is 9H-fluoren-9-ylmethyl.

In this Step Q, compounds F18 can be prepared, in some embodiments, by reacting F17 with the amine compound of Formula F5 in the presence of a reducing agent.

In some embodiments, said reacting is carried out in the presence of a reducing agent.

The reducing agent can be any compound capable of reducing an organic compound to a lower oxidization state, for example by use of an organosilane such as tri($C_{1-3}$ alkyl) silane (e.g., triethylsilane); elemental hydrogen or using a hydride reagent (such as NaB(OAc)$_3$H, NaBH$_4$, LiAlH$_4$ and the like); using triphenylphosphine; or using a combination of sodium iodide, chlorotrimethylsilane, and methanol. In some embodiments, this step can be performed in the presence of an acid such as trifluoroacetic acid. Suitable solvents include, but are not limited halogenated hydrocarbon solvents (e.g., dichloromethane, chloroform, dichloroethane or tetrachloroethane). In some embodiments, the halogenated hydrocarbon solvent is 1,2-dichloroethane.

In some embodiments, said reducing agent is an organosilane.

In some embodiments, said reducing agent is tri($C_{1-3}$ alkyl) silane.

In some embodiments, said reducing agent is triethylsilane.

In some embodiments, said reacting is carried out in the presence of an organic acid.

In some embodiments, said organic acid is trifluoroacetic acid.

In some embodiments, said organic acid is methanesulfonic acid.

In some embodiments, said reacting is performed in a solvent component comprising a halogenated hydrocarbon solvent.

In some embodiments, said halogenated hydrocarbon solvent is dichloromethane.

In some embodiments, said halogenated hydrocarbon solvent is 1,2-dichloroethane.

In some embodiments, the process further comprises deprotecting said compound of Formula F18 to afford a compound of Formula F10:

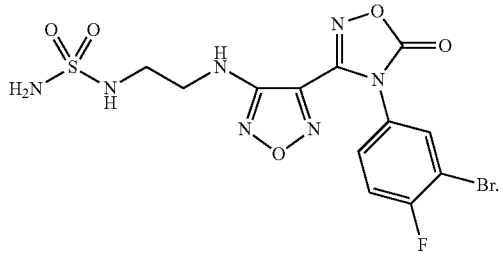

F10

In some embodiments, methods for the deprotection of particular amine protecting groups (such as carbamates) are known to one skilled in the art, such as those in Wuts and Greene, *Greene's Protective Groups in Organic Synthesis*, 4th Ed., pp 696-926, John Wiley & Sons: New York, 2006. For example, the tert-butoxycarbonyl group (e.g., when $R^4$ is tert-butyl) can be removed (e.g., hydrolyzed) from the nitrogen atom, for example, by treatment with an acid (such as hydrochloric acid, trifluoroacetic acid, toluenesulfonic acid, and the like); a combination of reagents (e.g., mixture of acetyl chloride and methanol) known to generate an acid; or a Lewis acid (e.g., $BF_3 \cdot Et_2O$). The benzyloxycarbonyl group (e.g., when $R^4$ is benzyl) can be removed (e.g., hydrogenolyzed) from the nitrogen atom, for example, by treatment with hydrogen and a catalyst (such as palladium on carbon). The methoxycarbonyl and ethoxycarbonyl groups (i.e., when $R^4$ is methyl or ethyl) can be removed by treatment with an inorganic base (such as KOH or $K_2CO_3$); a combination of reagents (e.g., mixture of acetyl chloride, sodium iodide and acetonitrile); or by treatment with an acid (e.g., HBr, AcOH). The 2,2,2-trichloroethoxycarbonyl group can be removed, for example by treatment with a catalyst (e.g., Zn/AcOH or Cd/AcOH). Suitable solvents for this step include, but are not limited to, methanol or tetrahydrofuran (THF), acetonitrile and the like. In some embodiments, the treating is performed at a temperature from about 30° C. to about 90° C., e.g., from about 50° C. to about 100° C., or from about 60° C. to about 80° C.

In some embodiments, said deprotecting comprises reacting the compound of Formula F18 with zinc in the presence of acetic acid.

In some embodiments, said deprotecting is performed in a solvent component comprising tetrahydrofuran.

In some embodiments, the process further comprises reacting said compound of Formula F10 with a base to afford a compound of Formula I:

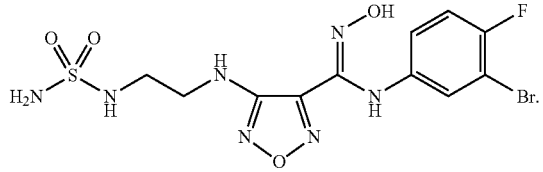

I

In some embodiments, said base comprises an alkali metal hydroxide.

In some embodiments, said alkali metal hydroxide is sodium hydroxide.

In some embodiments, said reacting is performed in a solvent component comprising tetrahydrofuran, water and ethanol.

In some embodiments, the process further comprises converting said compound of Formula F18 to a compound of Formula I:

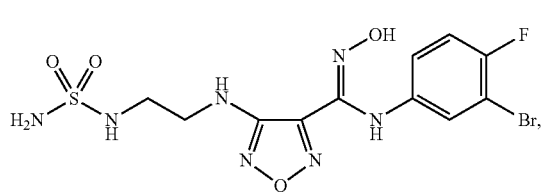

I wherein said converting comprises combining the compound of Formula F18 with a base to form a first mixture. In some embodiments, the base is N,N-bis(2-aminoethyl)ethane-1,2-diamine.

In some embodiments, the converting further comprises adding an acid to the first mixture. In some embodiments, said acid is an aqueous strong acid. In some embodiments, said aqueous strong acid is aqueous hydrochloric acid.

In some embodiments, said converting is performed in a solvent component comprising tetrahydrofuran and ethyl acetate.

The present application also provides a process comprising:

i) reacting a compound of Formula F19:

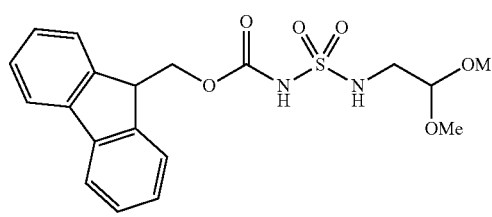

F19 with a compound of Formula F5:

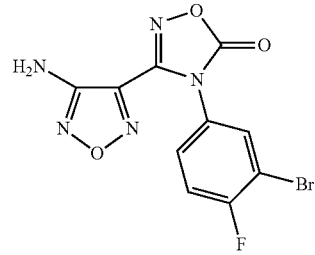

F5 in the presence of triethylsilane and methanesulfonic acid to afford a compound of Formula F20:

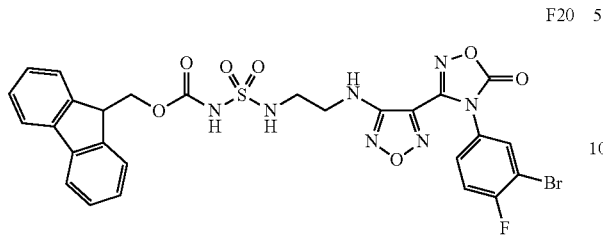

F20 and ii) converting said compound of Formula F20 to a compound of Formula I:

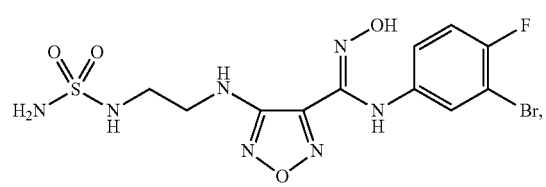

I wherein said converting comprises combining said compound of Formula F20 with N,N-bis(2-aminoethyl)ethane-1,2-diamine. In some embodiments, said converting further comprises adding aqueous hydrochloric acid after said combining.

Compound F17 can be made by a one step process (Step P) from chlorosulfonylisocyanate, as shown in Scheme 6.

Scheme 6

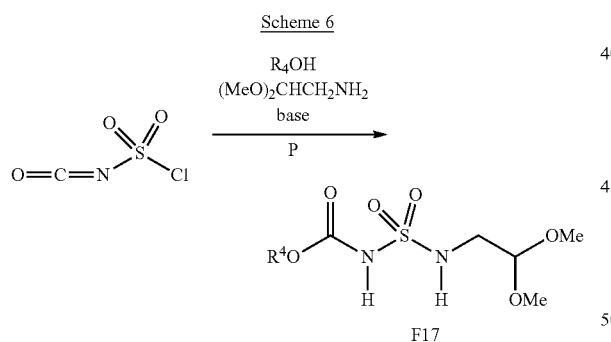

In some embodiments, the preparation of the compound of Formula F17 can be obtained by treating chloro sulfonylisocyanate with 2,2-dimethoxyethanamine and alcohol $R^4OH$ ($R^4$ is defined as above), optionally in a solvent (e.g., a halogenated hydrocarbon solvent such as dichloromethane, chloroform, dichloroethane, tetrachloroethane). In some embodiments, this step carried out in the presence of a base. The base can be either an organic base such as an acyclic amine (e.g., triethylamine, diisopropylethylamine (DIPEA), etc.) or a cyclic amine (e.g., pyrrolidine, piperidine, etc.); or an inorganic base such as alkali (e.g., NaOH, LiOH, KOH, $Mg(OH)_2$, etc.). In some embodiments, the reaction is carried out in a solvent, for example, a halogenated hydrocarbon solvent such as dichloromethane, chloroform, dichloroethane, or tetrachloroethane.

In some embodiments, the present application further provides a compound of Formula F17:

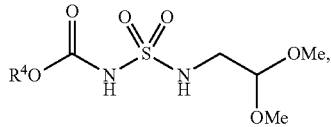

F17 wherein $R^4$ is $C_{1-6}$ alkyl, $C_{1-6}$ haloalkyl, or benzyl.

In some embodiments, $R^4$ is tert-butyl.

In some embodiments, $R^4$ is benzyl.

In some embodiments, $R^4$ is ethyl.

In some embodiments, $R^4$ is $C_{1-3}$ haloalkyl.

In some embodiments, $R^4$ is 2,2,2-trichloroethyl.

In some embodiments, $R^4$ is 9H-fluoren-9-ylmethyl.

In some embodiments, the compound of Formula F17 is tert-butyl N-(2,2-dimethoxyethyl)sulfamoylcarbamate.

In some embodiments, the compound of Formula F17 is benzyl N-(2,2-dimethoxyethyl)sulfamoylcarbamate.

In some embodiments, the compound of Formula F17 is ethyl N-(2,2-dimethoxyethyl)sulfamoylcarbamate.

In some embodiments, the compound of Formula F17 is 2,2,2-trichloroethyl N-(2,2-dimethoxyethyl)sulfamoylcarbamate.

In some embodiments, the compound of Formula F17 is (9H-fluoren-9-yl)methyl N-(2,2-dimethoxyethyl)sulfamoylcarbamate.

In some embodiments, the present application further provides a compound of Formula F18:

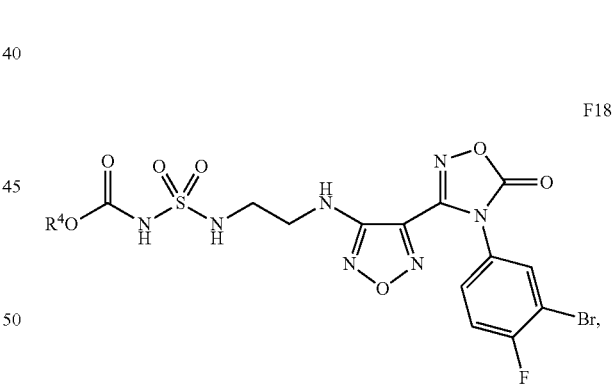

F18 wherein $R^4$ is $C_{1-6}$ alkyl, $C_{1-6}$ haloalkyl, or benzyl.

In some embodiments, $R^4$ is tert-butyl.

In some embodiments, $R^4$ is benzyl.

In some embodiments, $R^4$ is ethyl.

In some embodiments, $R^4$ is $C_{1-3}$ haloalkyl.

In some embodiments, $R^4$ is 2,2,2-trichloroethyl.

In some embodiments, $R^4$ is 9H-fluoren-9-ylmethyl.

In some embodiments, the compound of Formula F18 is benzyl ({[2-({[4-(3-bromo-4-fluorophenyl)-5-oxo-4,5-dihydro-1,2,4-oxadiazol-3-yl]-1,2,5-oxadiazol-3-yl}amino)ethyl]amino}sulfonyl)carbamate:

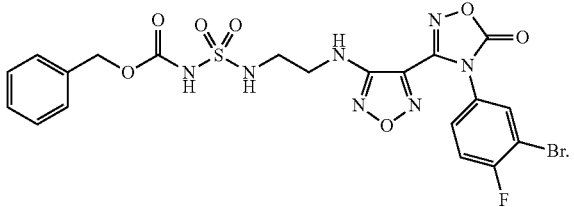 [SMILES: O=C(NS(=O)(=O)NCCNc1nonc1-c1noc(=O)n1-c1ccc(F)c(Br)c1)OCc1ccccc1]

In some embodiments, the compound of Formula F18 is ethyl ({[2-({[4-(3-bromo-4-fluorophenyl)-5-oxo-4,5-dihydro-1,2,4-oxadiazol-3-yl]-1,2,5-oxadiazol-3-yl}amino)ethyl]amino}sulfonyl)carbamate:

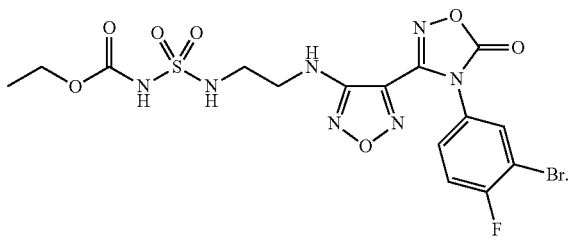 [SMILES: CCOC(=O)NS(=O)(=O)NCCNc1nonc1-c1noc(=O)n1-c1ccc(F)c(Br)c1]

In some embodiments, the compound of Formula F18 is 2,2,2-trichloroethyl ({[2-({[4-(3-bromo-4-fluorophenyl)-5-oxo-4,5-dihydro-1,2,4-oxadiazol-3-yl]-1,2,5-oxadiazol-3-yl}amino)ethyl]amino}sulfonyl)carbamate:

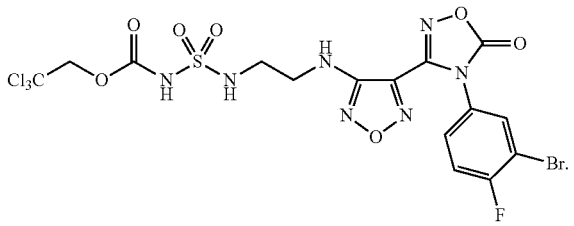

In some embodiments, the compound of Formula F18 is (9H-fluoren-9-yl)methyl N-(2-((4-(4-(3-bromo-4-fluorophenyl)-5-oxo-4,5-dihydro-1,2,4-oxadiazol-3-yl)-1,2,5-oxadiazol-3-yl)amino)ethyl)sulfamoylcarbamate:

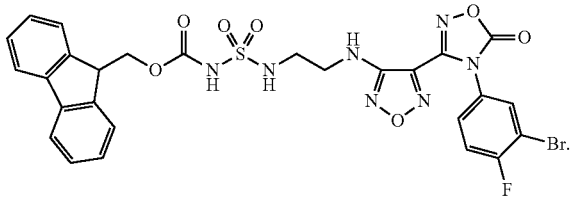 [SMILES: O=C(NS(=O)(=O)NCCNc1nonc1-c1noc(=O)n1-c1ccc(F)c(Br)c1)OCC1c2ccccc2-c2ccccc21]

As used herein, the term "alkyl," when used alone or together with additional moiety terms, refers to a straight-chained or branched, saturated hydrocarbon group having from 1 to 6 carbon atoms, 1 to 4 carbon atoms, or 1 to 3 carbon atoms. Example alkyl groups include methyl, ethyl, n-propyl, isopropyl, n-butyl, isobutyl, sec-butyl, tert-butyl, and the like.

As used herein, "alkenyl" refers to an alkyl group having one or more double carbon-carbon bonds. In some embodiments, said alkyl group has from 2 to 6 carbon atoms, 2 to 4 carbon atoms, or 2 to 3 carbon atoms. Example alkenyl groups include ethenyl (vinyl), propenyl, and the like.

As used herein, "alkenylalkyl" refers to a group of formula-alkyl-alkenyl. In some embodiments, the alkenylalkyl group is allyl.

As used herein, the term "haloalkyl," when used alone or together with an additional moiety, refers to an alkyl group substituted by one or more halogen atoms independently selected from F, Cl, Br, and I. Example haloalkyl groups include $CF_3$, $CHF_2$, $CH_2CF_3$, and the like.

As used herein, the term "alkoxy" refers to an —O-alkyl group. In some embodiments, the alkyl group has 1 to 6 carbon atoms, 1 to 4 carbon atoms, or 1 to 3 carbon atoms. Example alkoxy groups include methoxy, ethoxy, propoxy (e.g., n-propoxy and isopropoxy), t-butoxy, and the like.

As used herein, "trialkylamine" refers to a nitrogen atom substituted by three independently selected alkyl groups. In some embodiments, each alkyl group has from 2 to 6 carbon atoms, 2 to 4 carbon atoms, or 2 to 3 carbon atoms. Example trialkylamine groups include trimethylamine, triethylamine, and the like.

As used herein, the term "alkoxycarbonyl" refers to a group of formula —C(O)—O—alkyl. In some embodiments, the alkyl group has from 2 to 6 carbon atoms, 2 to 4 carbon atoms, or 2 to 3 carbon atoms. Example alkoxycarbonyl groups include ethoxycarbonyl, tert-butoxycarbonyl (Boc), and the like.

Halogenated hydrocarbon solvents refer to halogenated alkanes, such as dichloromethane, chloroform, dichloroethane or tetrachloroethane, wherein the alkane can be branched or straight-chained having 1 to 12 carbon atoms, 1 to 6 carbon atoms, or 1 to 4 carbon atoms with one or more halo atoms. In some embodiments, the halogenated hydrocarbon solvent is a chlorinated alkane of 1 to 12 carbon atoms, 1 to 6 carbon atoms, or 1 to 4 carbon atoms.

At various places in the present specification, substituents of compounds of the invention may be disclosed in groups or in ranges. It is specifically intended that the invention include each and every individual subcombination of the members of such groups and ranges.

It is intended that the compounds of the invention are stable. As used herein "stable" refers to a compound that is sufficiently robust to survive isolation to a useful degree of purity from a reaction mixture, and preferably capable of formulation into an efficacious therapeutic agent.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The compounds of the invention are further intended to include all possible geometric isomers. Cis and trans geometric isomers of the compounds are described and may be isolated as a mixture of isomers or as separated isomeric forms.

Compounds of the invention also include tautomeric forms. Tautomeric forms result from the swapping of a single bond with an adjacent double bond together with the concomitant migration of a proton.

Compounds of the invention can also include all isotopes of atoms occurring in the intermediates or final compounds. Isotopes include those atoms having the same atomic number but different mass numbers. For example, isotopes of hydrogen include tritium and deuterium.

In some embodiments, the compounds of the invention, and salts thereof, are substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

The present application also includes salts of the compounds described herein. As used herein, "salts" refers to derivatives of the disclosed compounds wherein the parent compound is modified by converting an existing acid or base moiety to its salt form. Examples of salts include, but are not limited to, mineral acid (such as HCl, HBr, $H_2SO_4$) or organic acid (such as acetic acid, benzoic acid, trifluoroacetic acid) salts of basic residues such as amines; alkali (such as Li, Na, K, Mg, Ca) or organic (such as trialkylammonium) salts of acidic residues such as carboxylic acids; and the like. The salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile (ACN) are preferred.

The present application also includes pharmaceutically acceptable salts of the compounds described herein. The "pharmaceutically acceptable salts" include a subset of the "salts" described above which are, conventional non-toxic salts of the parent compound formed, for example, from non-toxic inorganic or organic acids. Lists of suitable salts are found in *Remington's Pharmaceutical Sciences*, 17$^{th}$ ed., Mack Publishing Company, Easton, Pa., 1985, p. 1418 and *Journal of Pharmaceutical Science*, 66, 2 (1977), each of which is incorporated herein by reference in its entirety. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry; or by chromatography such as high performance liquid chromatography (HPLC) or thin layer chromatography. The compounds obtained by the reactions can be purified by any suitable method known in the art. For example, chromatography (medium pressure) on a suitable adsorbent (e.g., silica gel, alumina and the like), HPLC, or preparative thin layer chromatography; distillation; sublimation, trituration, or recrystallization. The purity of the compounds, in general, are determined by physical methods such as measuring the melting point (in case of a solid), obtaining a NMR spectrum, or performing a HPLC separation. If the melting point decreases, if unwanted signals in the NMR spectrum are decreased, or if extraneous peaks in an HPLC trace are removed, the compound can be said to have been purified. In some embodiments, the compounds are substantially purified.

Preparation of compounds can involve the protection and deprotection of various chemical groups. The need for protection and deprotection, and the selection of appropriate protecting groups can be readily determined by one skilled in the art. The chemistry of protecting groups can be found, for example, in Wuts and Greene, *Greene's Protective Groups in Organic Synthesis*, 4$^{th}$ Ed., John Wiley & Sons: New York, 2006, which is incorporated herein by reference in its entirety.

The reactions of the processes described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the reaction step, suitable solvent(s) for that particular reaction step can be selected. Appropriate solvents include water, alkanes (such as pentanes, hexanes, heptanes, cyclohexane, etc., or a mixture thereof), aromatic solvents (such as benzene, toluene, xylene, etc.), alcohols (such as methanol, ethanol, isopropanol, etc.), ethers (such as dialkylethers, methyl tert-butyl ether (MTBE), tetrahydrofuran (THF), dioxane, etc.), esters (such as ethyl acetate, butyl acetate, etc.), halogenated hydrocarbon solvents (such as dichloromethane (DCM), chloroform, dichloroethane, tetrachloroethane), dimethylformamide (DMF), dimethylsulfoxide (DMSO), acetone, acetonitrile (ACN), hexamethylphosphoramide (HMPA) and N-methyl pyrrolidone (NMP). Such solvents can be used in either their wet or anhydrous forms.

Resolution of racemic mixtures of compounds can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent composition can be determined by one skilled in the art.

Methods of Use

The compound of Formula I can inhibit activity of the enzyme indoleamine-2,3-dioxygenase (IDO). For example, the compound of Formula I can be used to inhibit activity of IDO in cell or in an individual in need of modulation of the enzyme by administering an inhibiting amount of the compound of Formula I.

The compounds of Formula I can be used in methods of inhibiting the degradation of tryptophan in a system containing cells expressing IDO such as a tissue, living organism, or cell culture. In some embodiments, the present application provides methods of altering (e.g., increasing) extracellular tryptophan levels in a mammal by administering an effective amount of the compound of Formula I. Methods of measuring tryptophan levels and tryptophan degradation are routine in the art.

The compounds of Formula I can be used in methods of inhibiting immunosuppression such as IDO-mediated immunosuppression in a patient by administering to the patient an effective amount of the compound of Formula I. IDO-mediated immunosuppression has been associated with, for example, cancers, tumor growth, metastasis, viral infection, viral replication, etc.

The compounds of Formula I can also be used in methods of treating diseases associated with activity or expression, including abnormal activity and/or overexpression, of IDO in an individual (e.g., patient) by administering to the individual in need of such treatment a therapeutically effective amount or dose of the compound of Formula I or a pharmaceutical composition thereof. Example diseases can include any disease, disorder or condition that is directly or indirectly linked to expression or activity of the IDO enzyme, such as over expression or abnormal activity. An IDO-associated disease can also include any disease, disorder or condition that can be prevented, ameliorated, or cured by modulating enzyme activity. Examples of IDO-associated diseases include cancer, viral infection such as HIV infection, HCV infection, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosusor. Example cancers treatable by the methods herein include cancer of the colon, pancreas, breast, prostate, lung, brain, ovary, cervix, testes, renal, head and neck, lymphoma, leukemia, melanoma, and the like. The compound of Formula I can also be useful in the treatment of obesity and ischemia.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with the compound of Formula I includes the administration of the compound of Formula I to an individual or patient, such as a human, having IDO, as well as, for example, introducing the compound of Formula I into a sample containing a cellular or purified preparation containing the IDO enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) preventing the disease; for example, preventing a disease, condition or disorder in an individual who may be predisposed to the disease, condition or disorder but does not yet experience or display the pathology or symptomatology of the disease; 2) inhibiting the disease; for example, inhibiting a disease, condition or disorder in an individual who is experiencing or displaying the pathology or symptomatology of the disease, condition or disorder (i.e., arresting further development of the pathology and/or symptomatology), or 3) ameliorating the disease; for example, ameliorating a disease, condition or disorder in an individual who is experiencing or displaying the pathology or symptomatology of the disease, condition or disorder (i.e., reversing the pathology and/or symptomatology).

Combination Therapy

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination the compound of Formula I for treatment of IDO-associated diseases, disorders or conditions. The agents can be combined with the compound of Formula I in a single dosage form, or the agents can be administered simultaneously or sequentially as separate dosage forms.

Suitable antiviral agents contemplated for use in combination the compound of Formula I can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddl); zalcitabine (ddC); stavudine (d4T); lamivudine (3TC); abacavir (1592U89); adefovir dipivoxil [bis (POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2, 4(1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141 W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

In the treatment of melanoma, suitable agents for use in combination with the compound of Formula I include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds according to the invention may also be combined with immunotherapy drugs, including cytokines such as interferon alpha, interleukin 2, and tumor necrosis factor (TNF) in the treatment of melanoma.

The compound of Formula I may also be used in combination with vaccine therapy in the treatment of melanoma. Antimelanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including the compound of Formula I, using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 102° to 104° F. Melphalan is the drug most often used in this chemotherapy procedure. This can be given with another agent called tumor necrosis factor (TNF) (see section on cytokines).

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (TAXOL™), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB and PD-1, or antibodies to cytokines (IL-10, TGF-β, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

When employed as pharmaceuticals, the compound of Formula I can be administered in the form of pharmaceutical compositions which is a combination of the compound of Formula I and a pharmaceutically acceptable carrier. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal, or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Pharmaceutical compositions containing the compound of Formula I can be prepared in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum *acacia*, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid pre-formulation composition containing a homogeneous mixture of the compound of Formula I. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of the present application.

The tablets or pills containing the compound of Formula I can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present application can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the the compound of Formula I can vary according to, for example, the particular use for which the treatment is made, the manner of administration of the compound, the health and condition of the patient, and the judgment of the prescribing physician. The proportion or concentration of the compound of Formula I in a pharmaceutical composition can vary depending upon a number of factors including dosage, chemical characteristics (e.g., hydrophobicity), and the route of administration. For example, the compound of Formula I can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compound of Formula I can also be formulated in combination with one or more additional active ingredients which can include any pharmaceutical agent such as antiviral agents, vaccines, antibodies, immune enhancers, immune suppressants, anti-inflammatory agents and the like.

The present application also includes pharmaceutical kits useful, for example, in the treatment or prevention of IDO-associated diseases or disorders, obesity, diabetes and other diseases referred to herein which include one or more containers containing a pharmaceutical composition comprising a therapeutically effective amount of the compound of Formula I. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

Example 1

Synthesis of 4-({2-[(Aminosulfonyl)amino]ethyl}amino)-N-(3-bromo-4-fluorophenyl)-N'-hydroxy-1,2,5-oxadiazole-3-carboximidamide

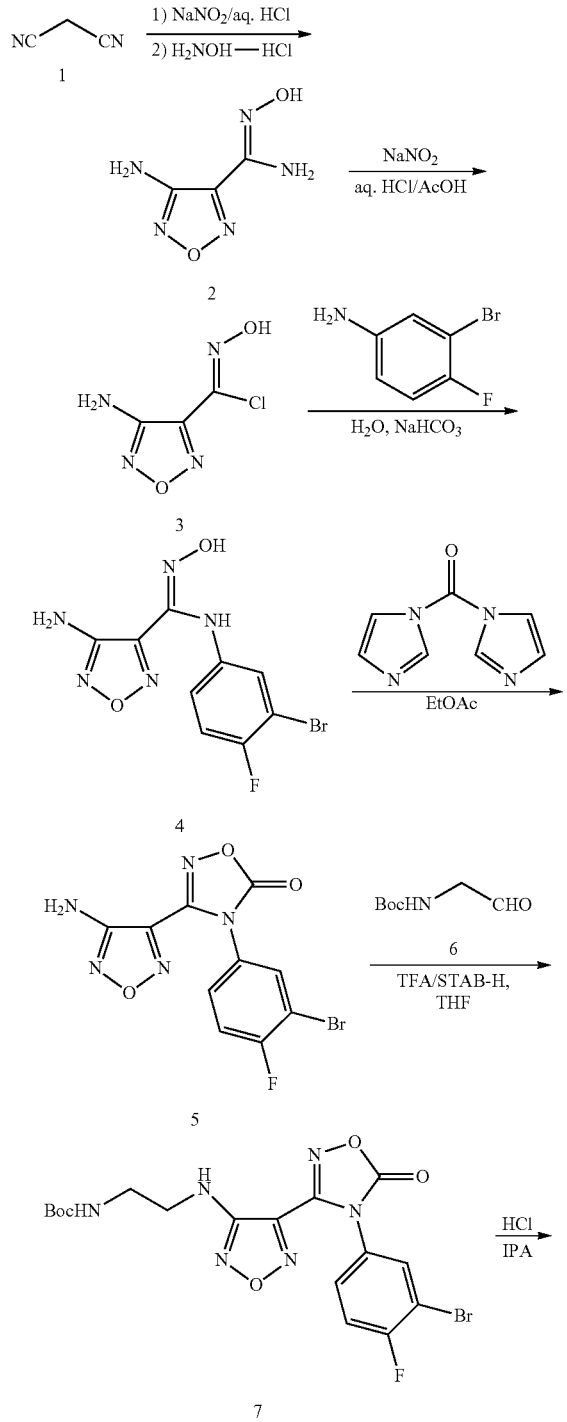
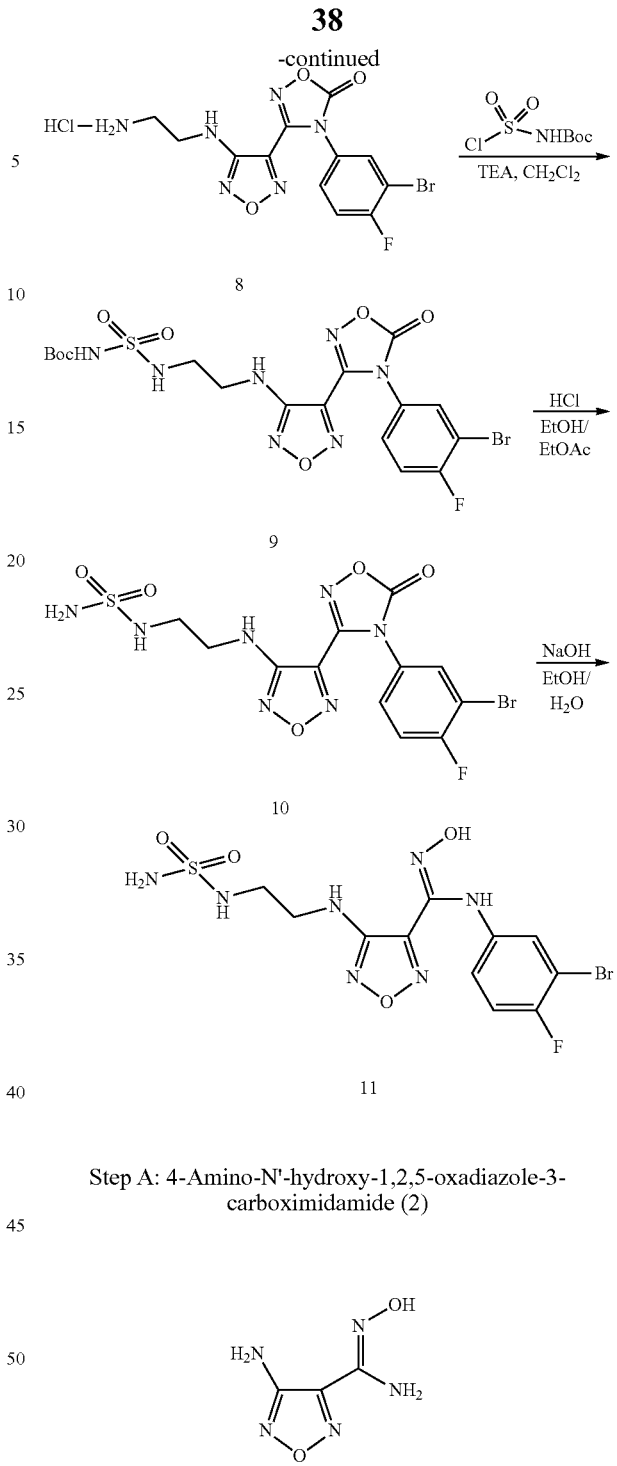

Step A: 4-Amino-N'-hydroxy-1,2,5-oxadiazole-3-carboximidamide (2)

Malononitrile [Aldrich, product #M1407] (320.5 g, 5 mol) was added to water (7 L), preheated to 45° C. and stirred at 45° C. for 5 min. The resulting solution was cooled in an ice bath and sodium nitrite (380 g, 5.5 mol, 1.1 equiv.) was added. When the temperature reached 10° C., 6 N hydrochloric acid (55 mL) was added. A mild exothermic reaction ensued with the temperature reaching 16° C. After 15 min the cold bath was removed and the reaction mixture was stirred for 1.5 h at 16-18° C. The reaction mixture was cooled to 13° C. and 50% aqueous hydroxylamine hydrochloride (990 g, 15 mol, 3.0 equiv.) was added all at once. The temperature rose to 26° C. When the exothermic reaction subsided the cold bath was removed and stirring was continued for 1 h at 26-27° C., then it was slowly brought to reflux. Reflux was maintained for 2 h and then the reaction mixture was allowed to gradually cool overnight. The reaction mixture was stirred in an ice bath and 6 N hydrochloric acid 800 mL) was added in portions over 40 min to adjust to pH 7.0. Stirring was continued in the ice bath at 5° C. The precipitate was collected by filtration, washed well with water and dried in a vacuum oven (50° C.) to give the desired product (644 g, 90%) as an off-white solid. $^{13}$C NMR (75 MHz, CD$_3$OD): δ 156.0, 145.9, 141.3; C$_3$H$_5$N$_5$O$_2$ (MW 143.10), LCMS (EI) m/e 144.0 (M$^+$+H).

Step B:
4-Amino-N-hydroxy-1,2,5-oxadiazole-3-carboximidoyl chloride (3)

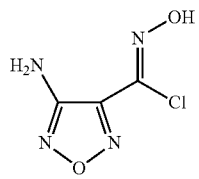

4-Amino-N'-hydroxy-1,2,5-oxadiazole-3-carboximidamide (422 g, 2.95 mol) was added to a mixture of water (5.9 L), acetic acid (3 L) and 6 N hydrochloric acid (1.475 L, 3.0 equiv.) and the suspension was stirred at 42-45° C. until a clear solution was achieved. Sodium chloride (518 g, 3.0 equiv.) was added and this solution was stirred in an ice/water/methanol bath. A solution of sodium nitrite (199.5 g, 0.98 equiv.) in water (700 mL) was added over 3.5 h while maintaining the temperature below 0° C. After complete addition, stirring was continued in the ice bath for 1.5 h and then the reaction mixture was allowed to warm to 15° C. The precipitate was collected by filtration, washed well with water, taken in ethyl acetate (3.4 L), treated with anhydrous sodium sulfate (500 g) and stirred at room temperature for 1 h. This suspension was filtered through sodium sulfate (200 g) and the filtrate was concentrated on a rotary evaporator. The residue was dissolved in methyl tert-butyl ether (5.5 L), treated with the activated charcoal (40 g), stirred at room temperature for 40 min and filtered through Celite. The solvent was removed in a rotary evaporator and the resulting product was dried in a vacuum oven (45° C.) to give the desired product (256 g, 53.4%) as an off-white solid. $^{13}$C NMR (100 MHz, CD$_3$OD) δ 155.8, 143.4, 129.7; C$_3$H$_3$ClN$_4$O$_2$ (MW 162.53), LCMS (EI) m/e 163/165 (M$^+$+H).

Step C: 4-Amino-N-(3-bromo-4-fluorophenyl)-N'-hydroxy-1,2,5-oxadiazole-3-carboximidamide (4)

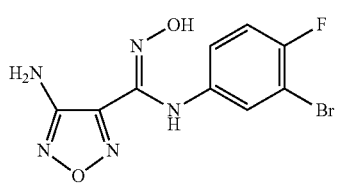 [SMILES: Nc1nonc1/C(=N/O)Nc1ccc(F)c(Br)c1]

4-Amino-N-hydroxy-1,2,5-oxadiazole-3-carboximidoyl chloride (33.8 g, 208 mmol) was mixed with water (300 mL). At 60° C., 3-bromo-4-fluoroaniline (Sigma-Aldrich) (43.6 g, 229 mmol, 1.1 equiv.) was added to the suspension with stirring for 10 min. A solution of sodium bicarbonate (26.3 g, 313 mmol, 1.5 equiv.) in water (300 mL) was added over 15 min with stirring at 60° C. After stirring 20 min, LCMS indicated reaction completion. The reaction mixture was then cooled to room temperature and extracted with ethyl acetate (2×300 mL). The combined ethyl acetate solution was dried over anhydrous sodium sulfate and concentrated to give the desired product (65 g, 99%) as an off-white solid, which was used in the subsequent reaction without further purification. C$_9$H$_7$BrFN$_5$O$_2$ (MW 316.09), LCMS (EI) m/e 316/318 (M$^+$+H).

Step D: 3-(4-Amino-1,2,5-oxadiazol-3-yl)-4-(3-bromo-4-fluorophenyl)-1,2,4-oxadiazol-5(4H)-one (5)

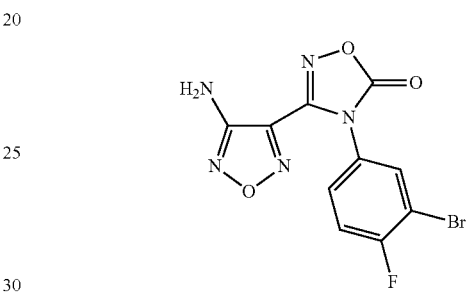

A mixture of 4-amino-N-(3-bromo-4-fluorophenyl)-N'-hydroxy-1,2,5-oxadiazole-3-carboximidamide (65.7 g, 208 mmol), N,N-carbonyldiimidazole (Sigma-Aldrich) (50.6 g, 312 mmol, 1.5 equiv.), and ethyl acetate (750 mL) was heated to 60° C. and stirred for 20 min. LCMS indicated reaction completed. The reaction was cooled to room temperature, washed with 1 N hydrochloric acid (2×750 mL), dried over sodium sulfate, and concentrated. The crude product was triturated with a mixture of dichloromethane, ethyl acetate, and diethyl ether to give the desired product (60.2 g, 85%) as an off-white solid. $^1$H NMR (300 MHz, DMSO-d$_6$) δ 8.05 (m, 1H), 7.69 (m, 1H), 7.57 (t, 1H, J=8.7 Hz), 6.58 (s, 2H); C$_{10}$H$_5$BrFN$_5$O$_3$ (MW 342.08), LCMS (EI) m/e 342/344 (M$^+$+H).

Step E: tert-Butyl [2-({4-[2-(3-bromo-4-fluorophenyl)-5-oxo-2,5-dihydro-1,2,4-oxadiazol-3-yl]-1,2,5-oxadiazol-3-yl}amino)ethyl]carbamate (7)

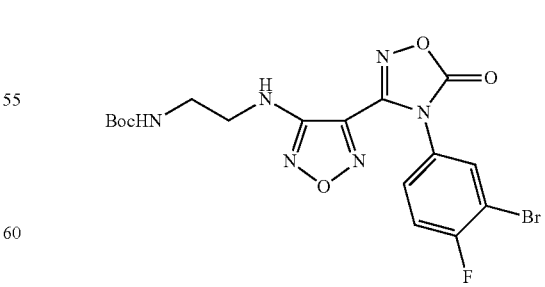

To a solution of trifluoroacetic acid (20.0 mL) and tetrahydrofuran (10.0 mL) was added sodium triacetoxyborohydride (10.59 g, 49.97 mmol, 10.0 equiv.) in portions with stirring under nitrogen. This mixture was stirred for 10 min at room temperature and then cooled to −5° C. A solution of 3-(4-amino-1,2,5-oxadiazol-3-yl)-4-(3-bromo-4-fluorophenyl)-1,2,4-oxadiazol-5(4H)-one (1.71 g, 5.0 mmol) and tert-butyl(2-oxoethyl)carbamate (Sigma-Aldrich) (1.99 g, 12.5 mmol, 2.5 equiv.) in THF (15.0 mL) was added drop-wise over 30 min with stirring while maintaining the temperature below 0° C. The reaction was stirred at −5 to 0° C. and additional portions of tert-butyl(2-oxoethyl)carbamate (0.20 g, 1.2 mmol, 0.24 equiv.) in THF (1.0 mL) were added drop-wise at 20 min, 40 min at 4 h intervals. HPLC indicated reaction completed after 5.25 h. The reaction mixture was poured into the ice-cold sodium bicarbonate (500 mL) and this solution was stirred at room temperature overnight. The precipitate was collected by filtration and washed with brine. The resulting residue was mixed with heptane (40 mL) and diethyl ether (40 mL) and stirred at room temperature for 5 h. The precipitate was collected by filtration, washed with diethyl ether and dried in a vacuum oven to give the desired product (1953 mg, 80.5%) as an off-white solid. $^1$H NMR (300 MHz, DMSO-d$_6$) δ 8.08 (m, 1H), 7.71 (m, 1H), 7.59 (t, 1H, J=8.7 Hz), 6.94 (m, 1H), 6.52 (m, 1H), 3.32 (m, 2H), 3.15 (m, 2H), 1.36 (s, 9H); C$_{17}$H$_{18}$BrFN$_6$O$_5$ (MW 485.26); LCMS (EI) m/e 507/509 (M$^+$+Na).

Step F: 3-{4-[(2-Aminoethyl)amino]-1,2,5-oxadiazol-3-yl}-4-(3-bromo-4-fluorophenyl)-1,2,4-oxadiazol-5(4H)-one hydrochloride (8)

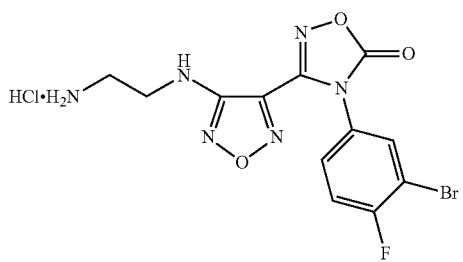

Method A (prepared from tert-Butyl [2-({4-[2-(3-bromo-4-fluorophenyl)-5-oxo-2,5-dihydro-1,2,4-oxadiazol-3-yl]-1,2,5-oxadiazol-3-yl}amino)ethyl]carbamate; Step E)

To a 500-mL flask was charged tert-butyl[2-({4-[2-(3-bromo-4-fluorophenyl)-5-oxo-2,5-dihydro-1,2,4-oxadiazol-3-yl]-1,2,5-oxadiazol-3-yl}amino)ethyl]carbamate (20 g, 41.2 mmol) and isopropanol (255 mL). The slurry was stirred at room temperature. Hydrogen chloride gas (7.55 g, 207 mmol, 5.0 equiv.) was added to the slurry with a subsurface glass tube over 16 min. Ethyl acetate (111 mL) was then added to the batch and the reaction was heated to 43° C. and stirred for 7.5 h. The batch was cooled to 19° C. and ethyl acetate (44 mL) was added. The slurry was filtered and the resulting residue was washed with ethyl acetate (2×55 mL). The isolated solid was dried under reduced pressure at 45° C. for 15 h to afford the desired product (16.61 g, 95.5% yield) as an off-white to white solid. $^1$H NMR (300 MHz, DMSO-d$_6$) δ 8.11 (bs, 3H), 7.78 (m, 1H), 7.73 (m, 1H), 7.59 (t, 1H, J=8.7 Hz), 6.74 (t, 1H, J=6.1 Hz), 3.50 (m, 2H), 3.02 (m, 2H); C$_{12}$H$_{11}$BrClFN$_6$O$_3$, (MW 421.61; C$_{12}$H$_{10}$BrFN$_6$O$_3$ for free base, MW 385.15), LCMS (EI) m/e 385/387 (M$^+$+H).

Method B (prepared directly from 3-(4-Amino-1,2,5-oxadiazol-3-yl)-4-(3-bromo-4-fluorophenyl)-1,2,4-oxadiazol-5(4H)-one; Step D)

Sodium triacetoxyborohydride (2.33 g, 11.0 mmol, 11.0 equiv.) was mixed with trifluoroacetic acid (12.0 mL, 155.8 mmol, 155.8 equiv.). The resulting solution was mixed at room temperature for 30 min. A solution of 3-(4-amino-1,2,5-oxadiazol-3-yl)-4-(3-bromo-4-fluorophenyl)-1,2,4-oxadiazol-5(4H)-one (5, 0.342 g, 1.0 mmol) and tert-butyl(2-oxoethyl)carbamate (Sigma-Aldrich) (1.04 g, 6.51 mmol, 6.5 equiv.) in dichloromethane (10.0 mL) and acetonitrile (6.0 mL) was stirred under N$_2$. This solution was cooled to −5° C. and the solution of sodium triacetoxyborohydride and trifluoroacetic acid was added drop-wise over 5 min. The reaction was stirred at room temperature for 4 h. HPLC and LC-MS (M$^+$-Boc+H: 385/387, bromide pattern) indicated a ratio of the desired product and the starting material was 4 to 1. The mixture was concentrated and diluted with dichloromethane (10 mL). The solution was cooled to 0° C. and 4 N sodium hydroxide was slowly added while maintaining the temperature at 0-5° C. to adjust the pH to 8-9. The aqueous layer was extracted with dichloromethane (3×10 mL). The combined dichloromethane solution was washed with sodium bicarbonate and brine, dried over sodium sulfate and concentrated. The crude residue was then dissolved in dichloromethane (6.0 mL) and the resulting solution was cooled to 0° C. 4 N hydrochloric acid in dioxane (3.0 mL) was added drop-wise at 0-5° C. The mixture was stirred at room temperature for 20 min. The precipitate was collected by filtration, washed with diethyl ether, and dried in vacuum to afford the desired product (289 mg, 54%) as an off-white solid. $^1$H NMR (300 MHz, DMSO-d$_6$) δ 8.11 (bs, 3H), 7.78 (m, 1H), 7.73 (m, 1H), 7.59 (t, 1H, J=8.7 Hz), 6.74 (t, 1H, J=6.1 Hz), 3.50 (m, 2H), 3.02 (m, 2H); C$_{12}$H$_{11}$BrClFN$_6$O$_3$, (MW 421.61; C$_{12}$H$_{10}$BrFN$_6$O$_3$ for free base, MW 385.15), LCMS (EI) m/e 385/387 (M$^+$+H).

Step G: tert-Butyl ({[2-({4-[4-(3-bromo-4-fluorophenyl)-5-oxo-4,5-dihydro-1,2,4-oxadiazol-3-yl]-1,2,5-oxadiazol-3-yl}amino)ethyl]amino}sulfonyl)carbamate (9)

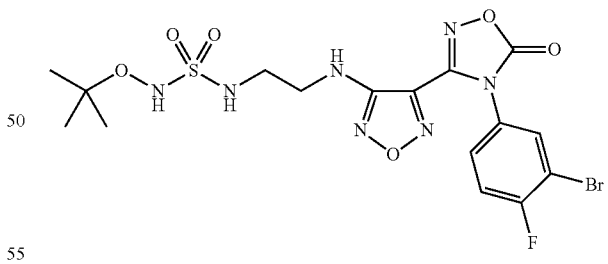

A 20-L glass reactor was charged with 3-{4-[(2-aminoethyl)amino]-1,2,5-oxadiazol-3-yl}-4-(3-bromo-4-fluorophenyl)-1,2,4-oxadiazol-5(4H)-one hydrochloride (1200 g, 2.846 mol) and dichloromethane (6.5 L) at room temperature. Triethylamine (950 g, 9.39 mol, 3.3 equiv.) was added to the batch over 7 minutes. The batch was then cooled to −14.6° C.

A 5-L round bottom flask was charged with tert-butanol (253 g, 3.41 mol, 1.2 equiv.) and dichloromethane (2.6 L). The solution was cooled to 0.9° C. To this solution was added chlorosulfonyl isocyanate (463 g, 3.27 mol, 1.15 equiv.) over 43 minutes while maintaining the batch temperature below 10° C. The resulting tert-butyl (chlorosulfonyl)carbamate solution was held at 3-5° C. for 1 h.

The solution of tert-butyl (chlorosulfonyl)carbamate was added to the reactor over 73 min while maintaining the batch temperature below 0° C. The batch was then warmed to 10° C. over 1 h and was then stirred at 10-14° C. for 1 h. Water (4.8 L) was added to the batch and the quenched reaction mixture was stirred at room temperature for 14.5 h. The batch was allowed to settle and phases separated. The dichloromethane solution was isolated kept in the reactor and was charged with acetic acid (513 g) over 25 min to precipitate the product. The resulting slurry was stirred at 20° C. for 2.5 h. The product was isolated by filtration and washed with dichloromethane (1.8 L). The product was dried under reduced pressure (−30 inHg) at 45° C. for 16 h to afford the desired product (1342 g, 83.5% yield) as a white solid.

$^1$H NMR (400 MHz, DMSO-$d_6$): δ 10.90 (s, 1 H), 8.08 (dd, J=6.2, 2.5 Hz, 1 H), 7.72 (m, 1 H), 7.59 (t, J=8.6 Hz, 1 H), 6.58 (t, J=5.7 Hz, 1 H), 3.38 (dd, J=12.7, 6.2 Hz, 2 H), 3.10 (dd, J=12.1, 5.9 Hz, 2 H), 1.41 (s, 9 H). $C_{17}H_{19}BrFN_7O_7S$ (MW 564.34), LCMS (EI) m/e 585.9/587.9 (M$^+$+Na).

Step H: N-[2-({4-[4-(3-Bromo-4-fluorophenyl)-5-oxo-4,5-dihydro-1,2,4-oxadiazol-3-yl]-1,2,5-oxadiazol-3-yl}amino)ethyl]sulfamide (10)

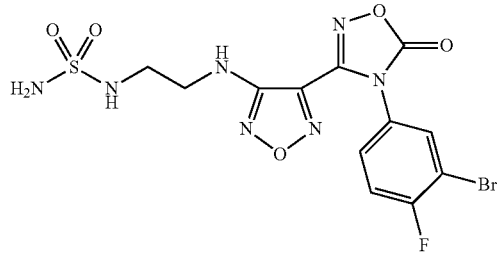 [SMILES: NS(=O)(=O)NCCNc1nonc1-c1noc(=O)n1-c1ccc(F)c(Br)c1]

To a 20-L flask containing tert-butyl ({[2-({4-[4-(3-bromo-4-fluorophenyl)-5-oxo-4,5-dihydro-1,2,4-oxadiazol-3-yl]-1,2,5-oxadiazol-3-yl}amino)ethyl]amino}sulfonyl)carbamate (1200 g, 2.126 mol) was added ethanol (12 L) at 20° C. The resulting mixture was stirred at room temperature and charged with hydrogen chloride gas (472 g, 12.9 mol, 6.07 equiv.). The batch was heated to 50° C. and the temperature was maintained for 3 h until reaction completion. Solvent was removed by vacuum distillation at 33-39° C. and 6 Kg of distillate was collected. Ethyl acetate (6.8 L, 6.1 Kg) was added to the batch and distilled to collect 5.1 Kg of distillate. Ethyl acetate (7.2 L, 6.48 Kg) was added to the batch and distilled to collect 5.1 Kg of distillate. Ethyl acetate (2.4 L, 2.14 Kg) was added to the batch to adjust the solvents ratio. $^1$H NMR indicated the mole ratio of ethyl acetate to ethanol was 1.0:0.1. The solution was heated to 65° C. n-Heptane (4.1 kg) was added to the solution at 60-65° C. over 43 min. The resulting slurry was stirred at 65° C. for 1 h. The slurry was cooled to 20° C. over 2.5 h and stirred at that temperature for 15 h. The product was collected by filtration and washed with n-heptane (2.42 L). The product was dried under reduced pressure at 45° C. for 65 h to afford the desired product (906 g, 91.8% yield) as an off-white solid. $^1$H NMR (400 MHz, DMSO-$d_6$) δ 8.08 (dd, J=6.2) 7.72 (m, 1 H), 7.59 (t, J=8.7 Hz, 1 H), 6.67 (t, J=5.9 Hz, 1H), 6.55 (s, 2H) 6.52 (t, J=6.0 Hz, 1 H), 3.38 (dd, J=12.7, 6.3 Hz, 2 H), 3.11 (dd, J=12.3, 6.3 Hz, 2H); $C_{12}H_{11}BrFN_7O_5S$ (MW 464.23), LCMS (EI) m/e 485.8/487.8 (M$^+$-$C_5H_8O_2$+Na).

Step I: 4-({2-[(Aminosulfonyl)amino]ethyl}amino)-N-(3-bromo-4-fluorophenyl)-N'-hydroxy-1,2,5-oxadiazole-3-carboximidamide (11)

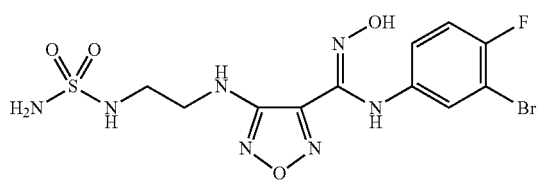 [SMILES: NS(=O)(=O)NCCNc1nonc1/C(=N/O)Nc1ccc(F)c(Br)c1]

To a 20-L glass reactor was added N-[2-({4-[4-(3-bromo-4-fluorophenyl)-5-oxo-4,5-dihydro-1,2,4-oxadiazol-3-yl]-1,2,5-oxadiazol-3-yl}amino)ethyl]sulfamide (799.4 g, 1.72 mol) and THF (3.2 L). The resulting solution was stirred at 20° C. for 7 min. and then charged with water (1.6 L). The batch was cooled to 2° C. and was charged with 30 wt % sodium hydroxide solution (475 mL, 666.4 g, 4.99 mol, 2.9 equiv.) over 8 minutes. The batch was warmed to 20° C. and the temperature was maintained for 16 h. The batch was then charged with methyl tert-butyl ether (8.0 L) over 23 minutes. Water (2.7 L) was added and the batch was cooled to about 0° C. The batch was then charged with 85 wt % phosphoric acid (370.7 g, 3.22 mol, 1.9 equiv.) over 9 minutes. The batch was warmed to 20° C. and stirred for 1 h. The batch was allowed to settle and phases were separated. The organic layer was retained in the reactor and charged with water (2.9 L) and 85 wt % phosphoric acid (370.7 g, 3.22 mol) and stirred at 20° C. for 1 h. The batch was allowed to settle and phases were separated. The organic layer was retained in the reactor and charged with water (3.2 L) and stirred at 20° C. for 1 h. The batch was allowed to settle and phases were separated. The organic solution was retained in the reactor and distilled under reduced pressure at 20° C. to remove 3.4 Kg of distillate. Ethanol (4.8 L) was charged to the batch and the batch was distilled to a volume of 3.2 L. This distillation process was repeated one more time. Ethanol (0.6 L) was added to the batch to adjust the batch volume to 4 L. The batch was stirred at 20° C. for 16 h and then charged with water (6.39 L). The resultant slurry was stirred at 20° C. for 5 h. The product was collected by filtration and was washed twice with a mixture of ethanol (529 mL) and water (1059 mL). The product was dried under reduced pressure at 45° C. for 65 h to afford the desired product (719.6 g, 95.4%) as a white solid. $^1$H NMR (400 MHz, DMSO-$d_6$): δ 11.51 (s, 1 H), 8.90 (s, 1 H), 7.17 (t, J=8.8 Hz, 1 H), 7.11 (dd, J=6.1, 2.7 Hz, 1 H), 6.76 (m, 1 H), 6.71 (t, J=6.0 Hz, 1 H), 6.59 (s, 2 H), 6.23 (t, J=6.1 Hz, 1 H), 3.35 (dd, J=10.9, 7.0 Hz, 2 H), 3.10 (dd, J=12.1, 6.2 Hz, 2 H); $C_{11}H_{13}BrFN_7O_4S$ (MW 438.23), LCMS (EI) m/e 437.9/439.9 (M$^+$+H).

Example 2

Alternate preparation of N-[2-({4-[4-(3-Bromo-4-fluorophenyl)-5-oxo-4,5-dihydro-1,2,4-oxadiazol-3-yl]-1,2,5-oxadiazol-3-yl}amino)ethyl]sulfamide

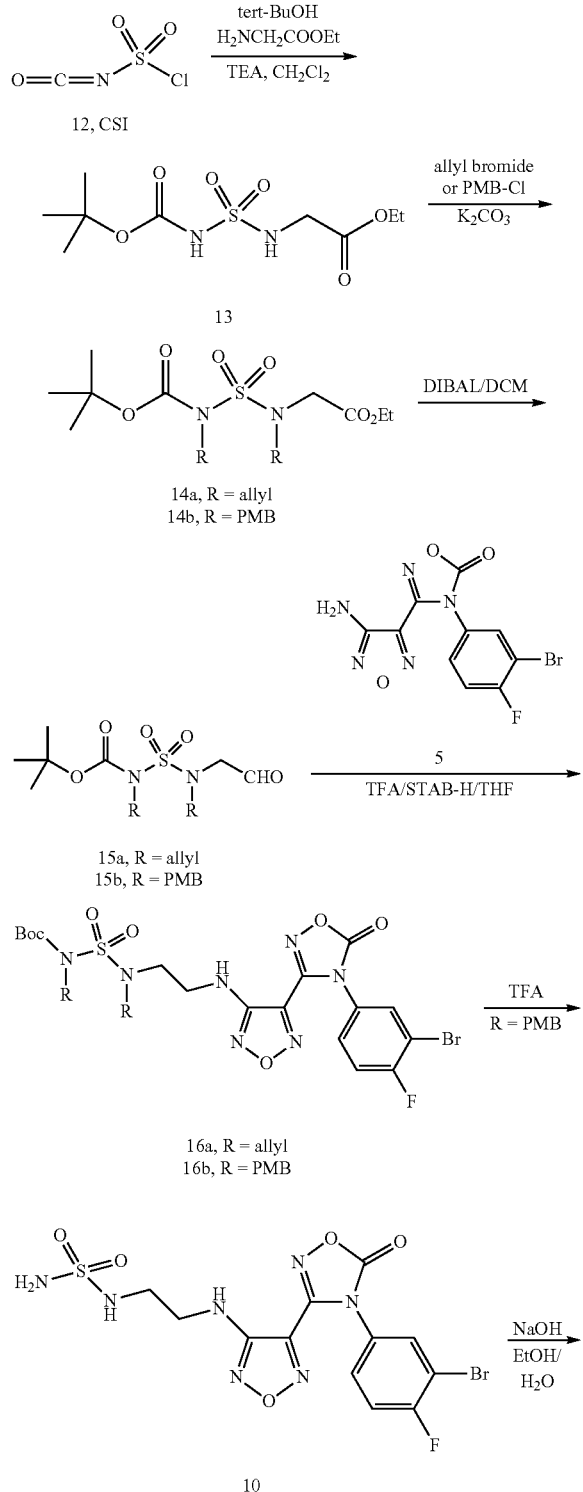

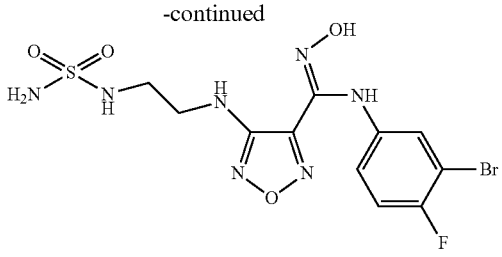

Step 1: Ethyl {[(tert-butoxycarbonyl)-amino]sulfonyl}aminoacetate (13)

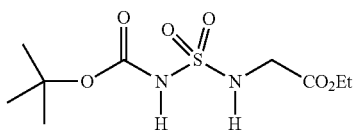 [SMILES: CCOC(=O)CNS(=O)(=O)NC(=O)OC(C)(C)C]

A solution of chlorosulfonylisocyanate (Sigma-Aldrich) (5.0 mL, 57.4 mmol) in dichloromethane (100 mL) was cooled to 0° C. Tert-butyl alcohol (4.26 g, 57.4 mmol, 1.0 equiv.) was added dichloromethane (100 mL) via an addition funnel. This solution was stirred at 0° C. for 30 min. Glycine ethyl ester hydrochloride (8.82 g, 63.2 mmol, 1.1 equiv.) was added followed by drop-wise addition of triethylamine (20.0 mL, 144 mmol, 2.5 equiv.) at 0° C. This reaction mixture was stirred at room temperature for 4 h. The reaction was diluted with dichloromethane (100 mL) and washed with 0.1 N hydrochloric acid and brine. The organic layer was dried over sodium sulfate and concentrated to give the desired product (13.2 g, 81.4%) as a crude off-white solid, which was used in the subsequent reaction without further purification. $^1$H NMR (300 MHz, DMSO-$d_6$) δ 10.88 (s, 1H), 8.07 (t, 1H, J=6.1 Hz), 4.08 (q, 2H, J=7.1 Hz), 3.78 (d, 2H, J=6.1 Hz), 1.40 (s, 9H), 1.18 (t, 3H, J=7.1 Hz).

Step 2a. Ethyl (allyl{[allyl(tert-butoxycarbonyl)amino]sulfonyl}amino)acetate (14a)

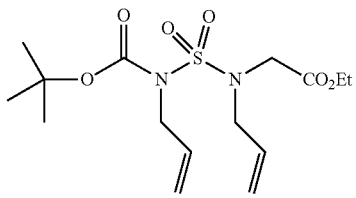 [SMILES: C=CCN(CC(=O)OCC)S(=O)(=O)N(CC=C)C(=O)OC(C)(C)C]

Ethyl ({[(tert-butoxycarbonyl)amino]sulfonyl}aminoacetate (1.0 g, 3.54 mmol) was mixed with potassium carbonate (2.45 g, 17.7 mmol, 5.0 equiv.) and acetonitrile (23.0 mL) under $N_2$ at room temperature. Allyl bromide (1.84 mL, 21.2 mmol, 6.0 equiv.) was added dropwise. This reaction mixture was heated to 70° C. and stirred at that temperature for 14 h. HPLC and LCMS indicated reaction completion. The reaction was filtered and the filtrate was concentrated. The residue was dissolved in dichloromethane and washed with sodium bicarbonate and brine. The organic layer was dried over sodium sulfate and concentrated to give the desired product (1.11 g, 87%) as crude off-white solid, which was used in the subsequent reaction without further purification. $^1$H NMR (300 MHz, DMSO-d$_6$) δ 5.75 (m, 2H), 5.20 (m, 4H), 4.12 (m, 6H), 3.89 (m, 2H), 1.43 (s, 9H), 1.18 (t, 3H, J=8.7 Hz).

Step 2b. Ethyl [{[(tert-butoxycarbonyl)(4-methoxybenzyl)amino]sulfonyl}(4-methoxybenzyl)amino] acetate (14b)

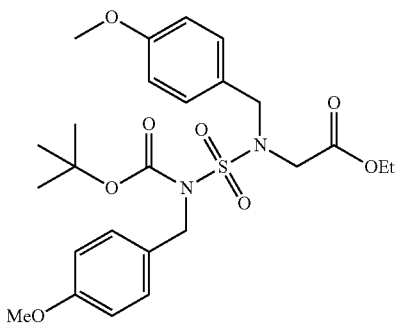 [SMILES: CCOC(=O)CN(Cc1ccc(OC)cc1)S(=O)(=O)N(Cc1ccc(OC)cc1)C(=O)OC(C)(C)C]

Ethyl ({[(tert-butoxycarbonyl)amino]sulfonyl}amino)acetate (1.00 g, 4.0 mmol) was mixed with N,N-dimethylformamide (DMF, 6.0 mL) and stirred at room temperature. Sodium iodide (0.01 g, 0.1 mmol, 0.025 equiv.), potassium carbonate (2.40 g, 20 mmol, 5.0 equiv.) and para-methoxybenzyl chloride (2.64 mL, 19.5 mmol, 4.875 equiv.) were added to the mixture. This reaction was warmed to 80° C. and stirred at 80° C. for 2 h. LCMS indicated reaction completion. The reaction was cooled to room temperature and filtered through Celite. The Celite bed was washed with dichloromethane and the combined organic filtrates were concentrated. The concentrated residue was dissolved in dichloromethane (20 mL) and washed with sodium bicarbonate (5×12 mL) and brine. The organic layer was dried over sodium sulfate and concentrated. The residue was purified on silica gel (0-40% ethyl acetate/hexane gradient elution) to give the desired product (1.39 g, 80%) as an off-white solid. $^1$H NMR (300 MHz, DMSO-d$_6$) δ 7.22 (m, 2H), 7.14 (m, 2H), 6.88 (m, 4H), 4.64 (s, 2H), 4.33 (s, 2H), 4.03 (q, 2H, J=7.1 Hz), 3.92 (s, 2H), 3.72 (s, 3H), 3.71 (s, 3H), 1.39 (s, 9H), 1.14 (t, 3H, J=7.1 Hz).

Step 3a. tert-Butyl allyl{[allyl(2-oxoethyl)amino]sulfonyl}carbamate (15a)

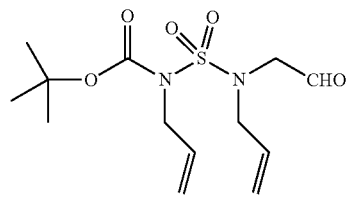 [SMILES: C=CCN(CC=O)S(=O)(=O)N(CC=C)C(=O)OC(C)(C)C]

A solution of ethyl (allyl{[allyl(tert-butoxycarbonyl)amino]sulfonyl}amino)acetate (1.11 g, 3.05 mmol) in dichloromethane (15 mL) at −78° C. under N$_2$ was treated with 1.0 M diisobutylaluminun hydride in dichloromethane (3.66 mL, 3.66 mmol, 1.2 equiv.). The reaction mixture was stirred at −78° C. for 1 h and then quenched with methanol (1.5 mL) and treated with a saturated solution of sodium potassium tartrate (65 mL). This solution was stirred at room temperature overnight. The aqueous layer was then extracted with dichloromethane (3×20 mL). The combined dichloromethane solution was washed with brine, dried over sodium sulfate, filtered, and concentrated to give the desired product (0.62 g, 64%) as a crude thick colorless oil, which was used in subsequent reaction without further purification. $^1$H NMR (300 MHz, DMSO-d$_6$) δ 9.45 (s, 1H), 5.76 (m, 2H), 5.18 (m, 4H), 4.15 (m, 4H), 3.72 (m, 2H), 1.43 (s, 9H).

Step 3b. tert-Butyl (4-methoxybenzyl){[(4-methoxybenzyl)(2-oxoethyl)amino]sulfonyl}carbamate (15b)

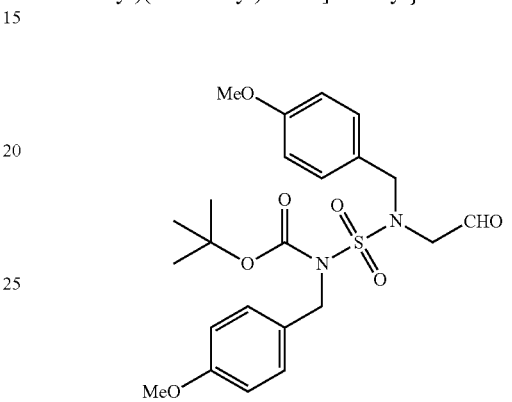

A solution of ethyl [{[(tert-butoxycarbonyl)(4-methoxybenzyl)amino]sulfonyl}(4-methoxybenzyl)amino]acetate (5.30 g, 10 mmol) in dichloromethane (20.0 mL) at −78° C. under N$_2$ was treated with 1.0 M diisobutylaluminum hydride in dichloromethane (12.2 mL, 12.2 mmol, 1.22 equiv.). The reaction mixture was stirred at −78° C. for 3 h. The reaction was then quenched with methanol (3 mL) and treated with dichloromethane (100 mL) and a saturated solution of sodium potassium tartrate (150 mL). This solution was stirred at room temperature overnight. The aqueous layer was then extracted with dichloromethane (3×20 mL). The combined dichloromethane solution was washed with brine, dried over sodium sulfate and concentrated. The residue was then purified on silica gel (0-30% ethyl acetate/hexane gradient elution) to give the desired product (3.45 g, 71%) as an off-white solid. $^1$H NMR (300 MHz, DMSO-d$_6$) δ 9.24 (s, 1H), 7.23 (m, 4H), 6.88 (m, 4H), 4.68 (s, 2H), 4.31 (s, 2H), 4.07 (s, 2H), 3.72 (s, 3H), 3.71 (s, 3H), 1.40 (s, 9H).

Step 4a. tert-Butyl allyl(N-allyl-N-(2-(4-(4-(3-bromo-4-fluorophenyl)-5-oxo-4,5-dihydro-1,2,4-oxadiazol-3-yl)-1,2,5-oxadiazol-3-ylamino)ethyl)sulfamoyl)carbamate (16a)

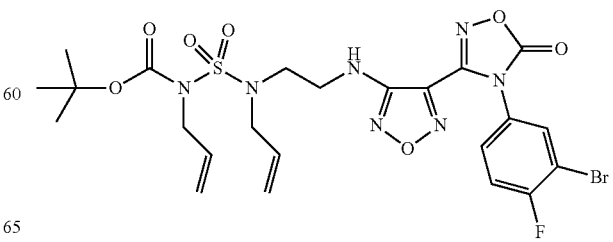

To a 50-mL flask was added sodium triacetoxyborohydride (1.06 g, 5.0 mmol, 1.0 equiv.), trifluoroacetic acid (TFA, 2.0 mL, 26 mmol) and tetrahydrofuran (THF, 1.0 mL) at ambient temperature. This mixture was cooled to −5° C. under $N_2$ and stirred at 0-5° C. for 10 min. To this solution was added 3-(4-amino-1,2,5-oxadiazol-3-yl)-4-(3-bromo-4-fluorophenyl)-1,2,4-oxadiazol-5(4H)-one (0.171 g, 5.0 mmol; Step D) and tert-butyl allyl{[allyl(2-oxoethy)amino]sulfonyl}carbamate (0.398 g, 2.5 mmol, 0.5 equiv.) in THF (1.5 mL) drop-wise at 0-5° C. over 5 min. The resulting reaction mixture was stirred under $N_2$ at 0-5° C. At 20 min, 40 min, and 2.5 h time points, a solution of tert-butyl allyl{[allyl (2-oxoethy)amino]sulfonyl}carbamate (0.040 g, 0.125 mmol, 0.25 equiv.) in THF (0.20 mL) was added drop-wise at 0-5° C. At 2.5 h, a solution of sodium triacetoxyborohydride (0.211 g, 1.0 mmol, 0.2 equiv.) in trifluoroacetic acid (TFA, 1.5 mL, 9.5 mmol) was added at 0-5° C. The reaction was warmed to room temperature and stirred overnight. The reaction mixture was then poured into an ice-cold saturated solution of sodium carbonate (50 mL) and extracted with dichloromethane (3×20 mL). The combined dichloromethane extracts were washed with brine, dried over sodium sulfate, and concentrated. The residue was then purified on silica gel (0-75% ethyl acetate/hexane gradient elution) to give the desired product (0.239 g, 74.2%) as an off-white solid. $^1$H NMR (300 MHz, DMSO-$d_6$) δ 8.07 (m, 1H), 7.71 (m, 1H), 7.58 (t, 1H, J=8.7 Hz), 6.62 (m, 1H), 5.77 (m, 2H), 5.19 (m, 4H), 4.17 (m, 2H), 3.89 (m, 2H), 3.44 (m, 2H), 3.38 (m, 2H), 1.42 (s, 9H); $C_{23}H_{27}BrFN_7O_7S$ (MW 644.47), LCMS (EI) m/e 544/546 (M$^+$-Boc+H).

Step 4b. tert-Butyl N-(2-(4-(4-(3-bromo-4-fluorophenyl)-5-oxo-4,5-dihydro-1,2,4-oxadiazol-3-yl)-1,2,5-oxadiazol-3-ylamino)ethyl)-N-(4-methoxybenzyl)sulfamoyl(4-methoxybenzyl)carbamate (16b)

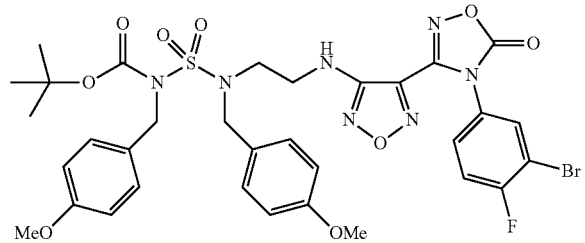 [SMILES: COc1ccc(CN(CCNc2nonc2-c2noc(=O)n2-c2ccc(F)c(Br)c2)S(=O)(=O)N(Cc2ccc(OC)cc2)C(=O)OC(C)(C)C)cc1]

To a 50-mL flask was added sodium triacetoxyborohydride (0.50 g, 2.37 mmol, 4.74 equiv.), trifluoroacetic acid (TFA, 1.0 mL, 13 mmol) and tetrahydrofuran at ambient temperature. This mixture was cooled to 0-5° C. under $N_2$ and stirred at 0-5° C. for 10 min To this solution was added tert-butyl(4-methoxybenzyl){[(4-methoxybenzyl)(2-oxoethyl)amino]sulfonyl}carbamate (0.40 g, 0.84 mmol, 1.68 equiv) and 3-(4-amino-1,2,5-oxadiazol-3-yl)-4-(3-bromo-4-fluorophenyl)-1,2,4-oxadiazol-5(4H)-one (0.17 g, 0.50 mmol; Step D) in tetrahydrofuran (THF, 1.50 mL) at 0-5° C. The reaction was stirred at 0-5° C. for 45 min and a solution of tert-butyl(4-methoxybenzyl){[(4-methoxybenzyl)(2-oxoethyl)amino]sulfonyl}carbamate (0.12 g, 0.20 mmol, 0.4 equiv.) in THF (0.50 mL) was then added at 0-5° C. After stirring at 0-5° C. for 1 h, the reaction was gradually warmed to room temperature with stirring. At 2.5 h and 4.5 h time points, trifluoroacetic acid (0.25 mL) was added. At 5 h, a solution of tert-butyl (4-methoxybenzyl) {[(4-methoxybenzyl)(2-oxoethyl)amino]sulfonyl}carbamate (0.060 g, 0.1 mmol, 0.2 equiv.) in THF (0.20 mL) was added. At 6.5 h, a solution of sodium triacetoxyborohydride (0.060 g, 0.24 mmol, 0.48 equiv.) in trifluoroacetic acid (0.25 mL) was added. HPLC indicated approximately 4% of the 3-(4-amino-1,2,5-oxadiazol-3-yl)-4-(3-bromo-4-fluorophenyl)-1,2,4-oxadiazol-5(4H)-one starting material (from Step D) still remaining. The reaction mixture was stirred at room temperature overnight. HPLC indicated reaction completion. The reaction mixture was poured into an ice-cold saturated solution of sodium carbonate (50 mL) and the mixture was extracted with dichloromethane (3×20 mL). The combined dichloromethane extracts were washed with brine, dried over sodium sulfate, and concentrated. The residue was then purified on silica gel (0-30% ethyl acetate/hexane gradient elution) to give the desired product (0.33 g, 82.5%) as an off-white solid. $^1$H NMR (300 MHz, DMSO-$d_6$) δ 8.06 (m, 1H), 7.69 (m, 1H), 7.57 (t, 1H, J=8.7 Hz), 7.22 (m, 4H), 6.87 (m, 4H), 6.48 (m, 1H), 4.72 (s, 2H), 4.36 (s, 2H), 3.70 (S, 6H), 3.39 (m, 2H), 3.31 (m, 2H), 1.37 (s, 9H); $C_{33}H_{35}BrFN_7O_9S$ (MW 804.64), LCMS (EI) m/e 826/828 (M$^+$-Boc+Na).

Step 5: N-[2-({4-[4-(3-Bromo-4-fluorophenyl)-5-oxo-4,5-dihydro-1,2,4-oxadiazol-3-yl]-1,2,5-oxadiazol-3-yl}amino)ethyl]sulfamide (10)

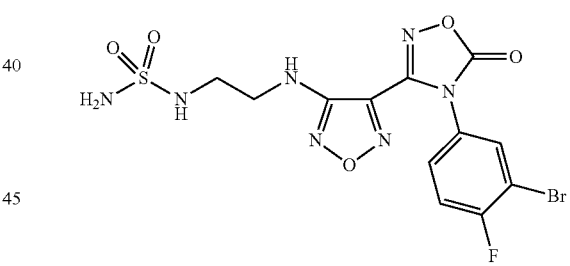

To a 25-mL flask was added tert-butyl {[[2-({4-[4-(3-bromo-4-fluorophenyl)-5-oxo-4,5-dihydro-1,2,4-oxadiazol-3-yl]-1,2,5-oxadiazol-3-yl}amino)ethyl](4-methoxybenzyl)amino]sulfonyl}(4-methoxybenzyl)carbamate (40.2 mg, 0.050 mmol) in trifluoroacetic acid (TFA, 0.50 mL, 6.5 mmol) at ambient temperature. This reaction mixture was heated to 70° C. under $N_2$ and stirred for 1 h. HPLC indicated reaction completed. The reaction mixture was cooled to room temperature and the TFA was evaporated. The residual TFA was removed by treatment with dichloromethane (3×10 mL) followed by evaporation in vacuum. The residue was then triturated with dichloromethane and methanol to give the desired product (20 mg, 87%) as a crude off-white solid. $^1$H NMR (400 MHz, DMSO-$d_6$) δ 8.08 (dd, J=6.2, 2.5 Hz, 1 H), 7.72 (m, 1 H), 7.59 (t, J=8.7 Hz, 1 H), 6.67 (t, J=5.9 Hz, 1H), 6.55 (s, 2H) 6.52 (t, J=6.0 Hz, 1 H), 3.38 (dd, J=12.7, 6.3 Hz, 2 H), 3.11 (dd, J=12.3, 6.3 Hz, 2H); $C_{12}H_{11}BrFN_7O_5S$ (MW 464.23), LCMS (EI) m/e 487.8/489.8 (M$^+$+Na).

Example 3

Alternate preparation of N-[2-({4-[4-(3-Bromo-4-fluorophenyl)-5-oxo-4,5-dihydro-1,2,4-oxadiazol-3-yl]-1,2,5-oxadiazol-3-yl}amino)ethyl]sulfamide

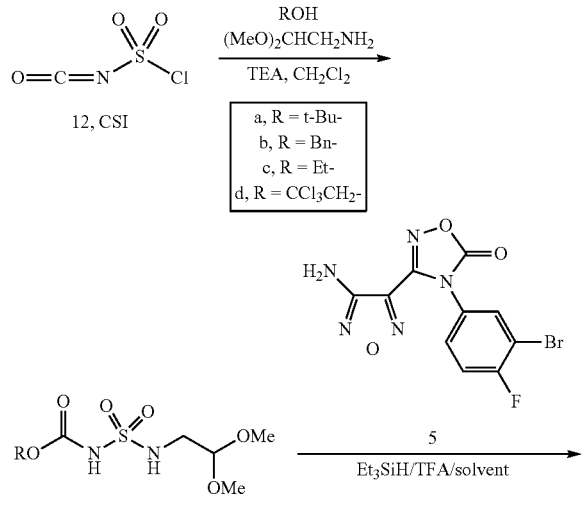

Step 1a. tert-Butyl N-(2,2-dimethoxyethyl)sulfamoylcarbamate (17a)

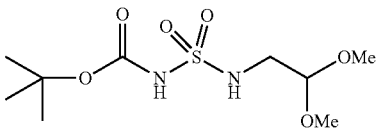 [SMILES: COC(CNS(=O)(=O)NC(=O)OC(C)(C)C)OC]

A solution of chlorosulfonylisocyanate (11.32 g, 80 mmol) in dichloromethane (120 mL) was cooled to 0° C. Tert-butyl alcohol (7.65 mL, 80.0 mmol, 1.0 equiv.) was added via addition funnel. The mixture was stirred at 0° C. for 1.5 h. To this mixture, a solution of aminoacetaldehyde dimethyl acetal (8.76 mL, 80.0 mmol, 1.0 equiv.) and triethylamine (TEA, 33.4 mL, 240 mmol, 3.0 equiv.) in methylene chloride (DCM 120.0 mL) was added drop-wise via addition funnel. The reaction was warmed to room temperature and stirred overnight. The reaction was treated with 0.1 N hydrochloric acid and the organic layer was washed with brine, dried over sodium sulfate and concentrated to give the desired product (15.6 g, 68.5%) as a crude off-white solid, which was used for the subsequent reaction without further purification: $^1$H NMR (300 MHz, DMSO-d$_6$) δ 10.84 (s, 1H), 7.62 (t, 1H, J=6.0 Hz), 4.38 (t, 1H, J=5.5 Hz), 3.24 (s, 6H), 2.96 (dd, 2H, J=5.8 Hz), 1.41 (s, 9H).

Step 1b. Benzyl N-(2,2-dimethaxyethyl)sulfamoylcarbamate (17b)

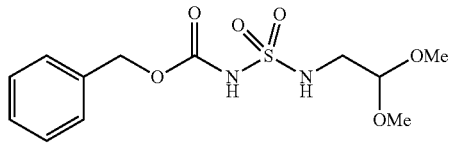 [SMILES: COC(CNS(=O)(=O)NC(=O)OCc1ccccc1)OC]

A solution of chlorosulfonylisocyanate (16.26 g, 114.9 mmol) in dichloromethane (100 mL) was cooled to 0° C. Benzyl alcohol (12.44 g, 115.0 mmol, 1.0 equiv.) was added via an addition funnel. The mixture was stirred at 0° C. for 0.5 h. To this mixture was added a mixture of aminoacetaldehyde dimethyl acetal (13.25 g, 126.0 mmol, 1.1 equiv.) and triethylamine (TEA, 17.4 g, 172 mmol, 1.5 equiv.) dropwise via an addition funnel at below 15° C. The reaction was warmed to room temperature and stirred overnight. The reaction mixture was treated with 0.5 N hydrochloric acid (100 mL) and the collected organic phase was washed with brine, dried over sodium sulfate and concentrated in vacuum to give the desired product (23.5 g, 64.3%) as a crude off-white solid. $^1$H NMR (300 MHz, DMSO-d$_6$) δ 11.29 (s, 1H), 7.90 (t, 1H, J=6.0 Hz), 7.37 (m, 5H), 5.12 (s, 2H), 4.35 (t, 1H, J=5.5 Hz), 3.21 (s, 6H), 2.97 (dd, 2H, J=5.8 Hz).

Step 1c. Ethyl N-(2,2-dimethoxyethyl)sulfamoylcarbamate (17c)

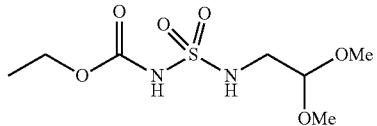 [SMILES: CCOC(=O)NS(=O)(=O)NCC(OC)OC]

A solution of chlorosulfonylisocyanate (11.32 g, 80 mmol) in dichloromethane (120 mL) was cooled to 0° C. Ethanol (4.67 mL, 80.0 mmol, 1.0 equiv.) was added via addition funnel. The mixture was stirred at 0° C. for 1.5 h. To this mixture was added a solution of aminoacetaldehyde dimethyl acetal (8.76 mL, 80.0 mmol, 1.0 equiv.), triethylamine (TEA, 33.4 mL, 240 mmol, 3.0 equiv.) in dichloromethane (DCM, 120.0 mL) drop-wise via addition funnel 0° C. The reaction was warmed to room temperature and stirred overnight. The reaction was treated with 0.1 N hydrochloric acid and the collected organic phase was washed with brine, dried over sodium sulfate and concentrated in vacuum to give the desired product (11.2 g, 55%) as a crude off-white solid. $^1$H NMR (300 MHz, DMSO-$d_6$) δ 11.13 (s, 1H), 7.81 (t, 1H, J=6.0 Hz), 4.37 (t, 1H, J=5.5 Hz), 4.09 (q, 2H, J=7.1 Hz), 3.23 (s, 6H), 2.97 (dd, 2H, J=5.8 Hz), 1.19 (t, 3H, J=7.1 Hz).

Step 1d. 2,2,2-Trichloroethyl N-(2,2-dimethoxyethyl)sulfamoylcarbamate (17d)

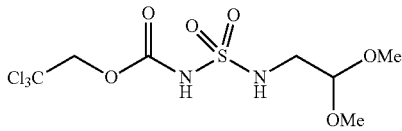

A solution of chlorosulfonylisocyanate (6.96 mL, 80 mmol) in dichloromethane (120 mL) was cooled to 0° C. 2,2,2-trichloroethanol (7.67 mL, 80.0 mmol, 1.0 equiv.) was added via addition funnel at 0° C. This mixture was stirred at 0° C. for 1.5 h. To this mixture was then added a solution of aminoacetaldehyde dimethyl acetal (8.76 mL, 80.0 mmol, 1.0 equiv.) and triethylamine (TEA, 33.4 mL, 240 mmol, 3.0 equiv.) in dichloromethane (DCM, 120.0 mL) added drop-wise via addition funnel at 0° C. The reaction was warmed to room temperature and stirred at room temperature overnight. The reaction was treated with 0.1 N hydrochloric acid and the collected organic phase was washed with brine, dried over $Na_2SO_4$, and concentrated to give the desired product (28.01 g, 97%) as a crude off-white solid, which was used in the subsequent reaction without further purification. $^1$H NMR (300 MHz, DMSO-$d_6$) δ 11.79 (s, 1H), 8.08 (t, 1H, J=5.9 Hz), 4.90 (s, 2H), 4.37 (t, 1H, J=5.5 Hz), 3.23 (s, 6H), 3.00 (dd, 2H, J=5.7 Hz).

Step 2a. Tert-butyl ({[2-({[4-(3-bromo-4-fluorophenyl)-5-oxo-4,5-dihydro-1,2,4-oxadiazol-3-yl]-1,2,5-oxadiazol-3-yl}amino)ethyl]amino}sulfonyl)carbamate (18a)

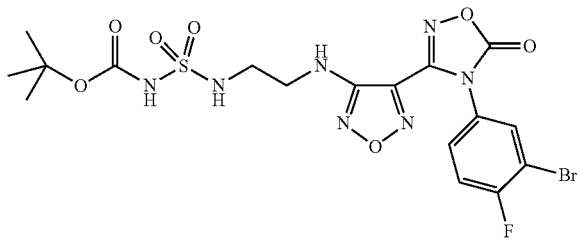 [SMILES: CC(C)(C)OC(=O)NS(=O)(=O)NCCNc1nonc1-c1noc(=O)n1-c1ccc(F)c(Br)c1]

A mixture of 3-(4-amino-1,2,5-oxadiazol-3-yl)-4-(3-bromo-4-fluorophenyl)-1,2,4-oxadiazol-5(4H)-one (103 mg, 0.302 mmol, 1.5 equiv.; Step D) and tert-butyl N-(2,2-dimethoxyethyl)sulfamoylcarbamate (57.2 mg, 0.201 mmol) in dichloromethane (1.0 mL) was stirred under $N_2$ at room temperature. To this mixture was added trifluoroacetic acid (0.50 mL, 6.5 mmol) and triethylsilane (80.2 μL, 0.502 mmol, 2.5 equiv.) drop-wise. This reaction mixture was stirred at room temperature for 2 h. HPLC indicated approximately 30% conversion. The reaction mixture was cooled to 0° C. and quenched with saturated sodium bicarbonate to pH ~8. The mixture was extracted in ethyl acetate (3×10 mL). The combined organic extracts were washed with brine, dried over sodium sulfate and concentrated. The residue was purified by preparative TLC (50% ethyl acetate/hexane) to give the desired product (27.5 mg, 29.5%) as an off-white solid. $^1$H NMR (DMSO-$d_6$, 400 MHz): δ 10.90 (s, 1H), 8.08 (dd, J=6.2, 2.5 Hz, 1H), 7.72 (m, 1H), 7.59 (t, J=8.6 Hz, 1H), 6.58 (t, J=5.7 Hz, 1H), 3.38 (dd, J=12.7, 6.2 Hz, 2H), 3.10 (dd, J=12.1, 5.9 Hz, 2H), 1.41 (s, 9H). $C_{17}H_{19}BrFN_7O_7S$ (MW 564.34), LCMS (EI) m/e 485.8/487.8 ($M^+$-$C_5H_8O_2$+Na).

Step 2b. Benzyl ({[2-({[4-(3-bromo-4-fluorophenyl)-5-oxo-4,5-dihydro-1,2,4-oxadiazol-3-yl]-1,2,5-oxadiazol-3-yl}amino)ethyl]amino}sulfonyl)carbamate (18b)

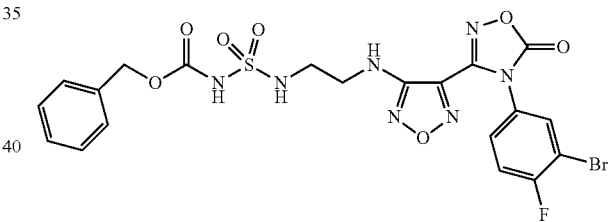

A mixture of 3-(4-amino-1,2,5-oxadiazol-3-yl)-4-(3-bromo-4-fluorophenyl)-1,2,4-oxadiazol-5(4H)-one (68 mg, 0.20 mmol; from Step D) and benzyl {[(2,2-dimethoxyethyl)amino]sulfonyl}carbamate (191 mg, 0.60 mmol, 3.0 equiv.) in 1,2-dichloroethane (3.0 mL) was cooled to 0° C. To this mixture was added trifluoroacetic acid (1.0 mL, 13.0 mmol) and triethylsilane (105 μL, 0.66 mmol, 3.3 equiv.) drop-wise. This reaction mixture was stirred at 0° C. for 2 h. HPLC indicated reaction completion. The reaction mixture was cooled to 0° C. and quenched with saturated sodium bicarbonate to pH ~8. and the quenched reaction mixture was extracted with EtOAc (3×10 mL). The combined organic extracts were washed with brine, dried over sodium sulfate and concentrated. The residue was then stirred in a mixture of heptane and diethyl ether overnight. The solids were collected by filtration, washed with heptane and dried in vacuum to give the desired product (125 mg, 99%) as a crude off-white solid. $^1$H NMR (300 MHz, DMSO-$d_6$) δ 11.31 (s, 1H), 8.05 (m, 1H), 7.87 (m, 1H), 7.68 (m, 1H), 7.56 (m, 1H), 7.32 (m, 5H), 6.54 (m, 1H), 5.07 (s, 2H), 3.29 (m, 2H), 3.09 (m, 2H); $C_{20}H_{17}BrFN_7O_7S$ (MW 598.36), LCMS m/e 598/600 (M$^+$+H).

Step 2c. Ethyl ({[2-({4-[4-(3-bromo-4-fluorophenyl)-5-oxo-4,5-dihydro-1,2,4-oxadiazol-3-yl]-1,2,5-oxadiazol-3-yl}amino)ethylamino}sulfonyl)carbamate (18c)

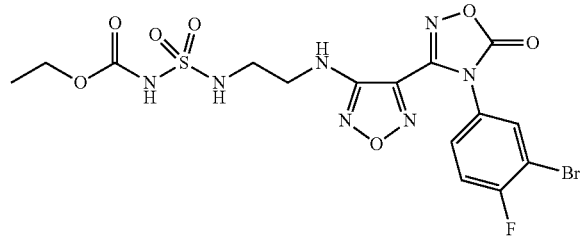 [SMILES: CCOC(=O)NS(=O)(=O)NCCNc1nonc1-c1noc(=O)n1-c1ccc(F)c(Br)c1]

A mixture of 3-(4-amino-1,2,5-oxadiazol-3-yl)-4-(3-bromo-4-fluorophenyl)-1,2,4-oxadiazol-5(4H)-one (68 mg, 0.20 mmol; from Step D) and ethyl {[(2,2-dimethoxyethyl)amino]sulfonyl}carbamate (154 mg, 0.600 mmol, 3.0 equiv.) in 1,2-dichloroethane (2.50 mL, 31.7 mmol) was stirred at 0° C. To this mixture was added trifluoroacetic acid (1.00 mL, 13.0 mmol) and triethylsilane (105 µL, 0.66 mmol, 3.3 equiv.)=drop-wise. The reaction mixture was stirred at 0° C. for 3 h. HPLC indicated 97.5% conversion to the desired product. The reaction mixture was cooled to 0° C. and quenched with saturated sodium bicarbonate to pH ~8. The mixture was extracted in ethyl acetate (3×10 mL). The combined organic extracts were washed with brine, dried over sodium sulfate and concentrated. The residue was stirred in a mixture of heptane and diethyl ether overnight. The solids were collected by filtration, washed with heptane to give the desired product (95 mg, 88%) as a crude off-white solid. $^1$H NMR (300 MHz, DMSO-d$_6$) δ 11.18 (s, 1H), 8.08 (m, 1H), 7.70 (m, 2H), 7.59 (t, 1H, J=8.7 Hz), 6.56 (s, 1H), 4.04 (d, 2H, J=7.2 Hz), 3.35 (m, 2H), 3.11 (m, 2H), 1.15 (t, 3H, J=7.2 Hz); $C_{15}H_{15}BrFN_7O_7S$ (MW 536.29), LCMS (EI) m/e 536/538 (M$^+$+H).

Step 2d. 2,2,2-Trichloroethyl ({[2-({4-[4-(3-bromo-4-fluorophenyl)-5-oxo-4,5-dihydro-1,2,4-oxadiazol-3-yl]-1,2,5-oxadiazol-3-yl}amino)ethyl]amino}sulfonyl)carbamate (18d)

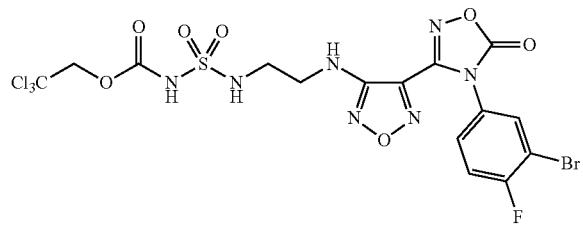

A suspension of 3-(4-amino-1,2,5-oxadiazol-3-yl)-4-(3-bromo-4-fluorophenyl)-1,2,4-oxadiazol-5(4H)-one (5, 0.680 g, 1.99 mmol) and 2,2,2-trichloroethyl {[(2,2-dimethoxyethyl)amino]sulfonyl}carbamate (17d, 2.22 g, 6.17 mmol, 3.1 equiv.) in dichloromethane (DCM, 6.0 mL) was stirred at room temperature. To this mixture was added triethylsilane (1.27 mL, 7.95 mmol, 4.0 equiv.) and a solution of trifluoroacetic acid (TFA, 3.0 mL, 39.0 mmol) in dichloromethane (DCM, 2.0 mL) while maintaining the reaction temperature below 30° C. The reaction mixture became homogenous after 5 min with agitation at room temperature and was stirred at room temperature for 1 h. HPLC indicated reaction completion. The reaction was filtered and the precipitate was suspended in a mixture of dichloromethane and heptane (ratio of dichloromethane to heptane was 1 to 9 by volume). The suspension was stirred at room temperature overnight. The precipitate was collected by filtration and washed with 10% dichloromethane in heptane and dried in vacuum to give the desired product (1.15 g, 90.4%) as an off-white solid, which was used in the subsequent reaction without further purification. $^1$H NMR (300 MHz, DMSO-d$_6$) δ 11.85 (s, 1H), 8.07 (m, 2H), 7.70 (m, 1H), 7.57 (t, 1H, J=8.7 Hz), 6.56 (m, 1H), 4.88 (m, 2H), 3.37 (m, 2H), 3.16 (m, 2H); $C_{15}H_{12}BrCl_3FN_7O_7S$ (MW 639.62), LCMS (EI) m/e 638/640/642 (M$^+$+H).

Step 3. N-[2-({4-[4-(3-Bromo-4-fluorophenyl)-5-oxo-4,5-dihydro-1,2,4-oxadiazol-3-yl]-1,2,5-oxadiazol-3-yl}amino)ethyl]sulfamide (10)

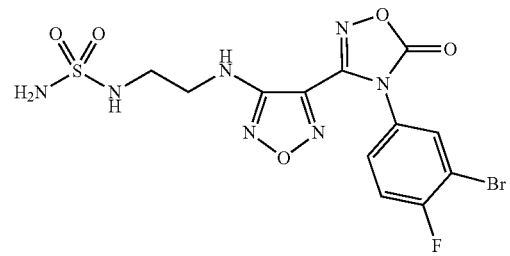 [SMILES: NS(=O)(=O)NCCNc1nonc1-c1noc(=O)n1-c1ccc(F)c(Br)c1]

A solution of 2,2,2-trichloroethyl ({[2-({4-[4-(3-bromo-4-fluorophenyl)-5-oxo-4,5-dihydro-1,2,4-oxadiazol-3-yl]-1,2,5-oxadiazol-3-yl}amino)ethyl]amino}sulfonyl)carbamate (320 mg, 0.50 mmol; from Step Q, Method D) in tetrahydrofuran (THF, 4.0 mL) was stirred at room temperature. Acetic acid (0.30 mL, 5.3 mmol) and zinc flakes (160 mg, 2.5 mmol, 5.0 equiv.) were sequentially added. This reaction mixture was stirred at room temperature for 3 h. HPLC indicated reaction completion. The reaction mixture was filtered through Celite and the Celite was washed with THF. The combined filtrate was concentrated in vacuum and the resulting residue was dissolved in ethyl acetate (20 mL). The ethyl acetate solution was washed with saturated sodium carbonate and brine, dried over sodium sulfate and concentrated. The crude material was crystallized from ethyl acetate and diethyl ether to give the desired product (147 mg, 63%) as an off-white solid.

Example 4
Alternate Preparation of 4-({2-[(Aminosulfonyl)amino]ethyl}amino)-N-(3-bromo-4-fluorophenyl)-N'-hydroxy-1,2,5-oxadiazole-3-carboximidamide
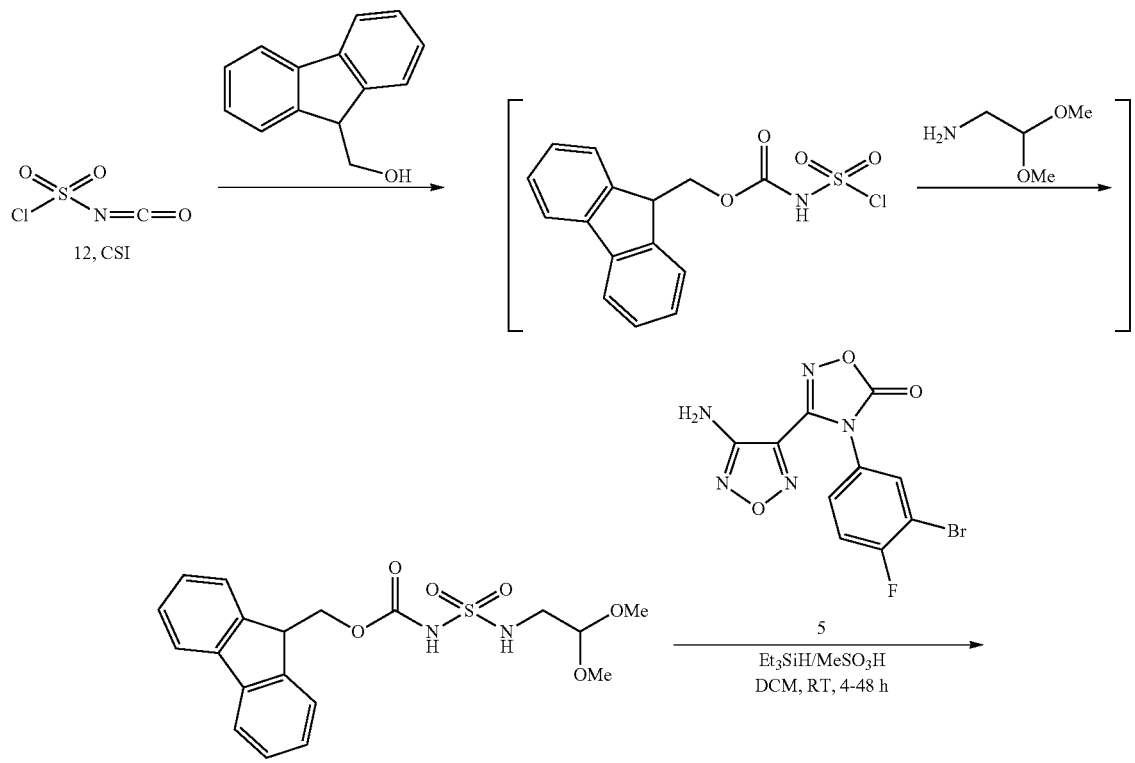
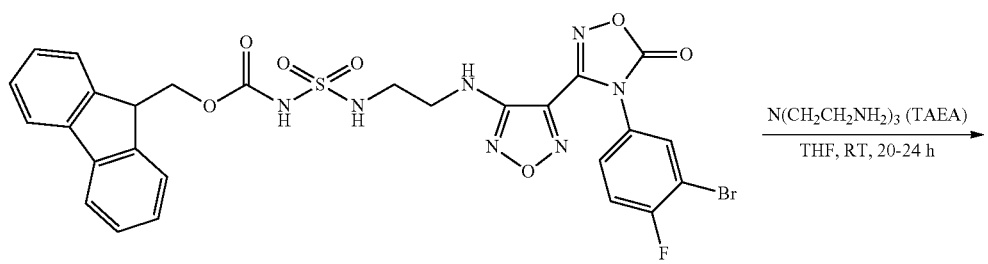
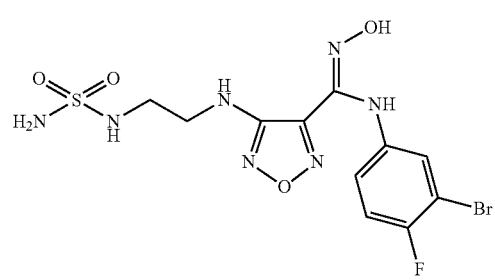

Step 1. (9H-fluoren-9-yl)methyl N-(2,2-dimethoxyethyl)sulfamoylcarbamate

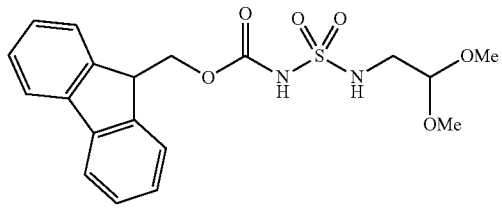 [SMILES: COC(CNS(=O)(=O)NC(=O)OCC1c2ccccc2-c2ccccc21)OC]

Into an oven dried 2 L 4-neck round bottom flask was charged 9-fluorenylmethanol (50.0 g, 255 mmol) and anhydrous DCM (382 mL) at room temperature. The resulting slurry was cooled in an ice-bath to about 0-5° C. A solution of chlorosulfonyl isocyanate (CSI, 23.0 mL, 264 mmol) in anhydrous DCM (127 mL) was added dropwise to the slurry through an addition funnel over 22 minutes, maintaining the reaction mixture temperature at <5° C. The resulting mixture was stirred at 0-5° C. for 1.75 h, producing a thick white slurry. A solution of aminoacetaldehyde dimethyl acetal (27.9 mL, 255 mmol) in anhydrous DCM (382 mL) and 4-methylmorpholine (84.0 mL, 764 mmol) were added to the mixture at about 0-5° C. over 71 minutes. The resulting reaction mixture was then stirred in the ice bath for 1.5 hours. When HPLC showed the reaction was complete, the reaction mixture was acidified by the dropwise addition of a 1.0 M phosphoric acid ($H_3PO_4$, aq., 640 mL) over 22 minutes to pH 1-2. Water (300 mL), EtOAc (2150 mL) and heptane (250 mL) were then added and the resulting mixture was stirred for 10 minutes. The two phases were separated and the organic phase was washed sequentially with water (500 mL), heptane (300 mL) and water (2×500 mL) and dried over $MgSO_4$. The filtrate was concentrated under vacuum to dryness. The resulting solids were redissolved in EtOAc (600 mL) at 65° C. and the warm solution was filtered into a clean 3 L round bottom flask. The filtrate was cooled to room temperature and stirred for 2.5 h before heptane (1200 mL) was then added via an addition funnel over 80 min. After stirring overnight at room temperature, the mixture was then cooled in an ice bath for 1 h. The resulting solids were collected by filtration, washed with 25% EtOAc/heptane (250 mL), and dried overnight at about 40-45° C. under vacuum to afford 9H-fluoren-9-ylmethyl {[(2,2-dimethoxyethyl)amino]sulfonyl}carbamate (91.3 g, 88% yield) as a white powder. $^1$H NMR (300 MHz, DMSO-$d_6$) δ 11.43 (s, 1H), 7.98-7.85 (m, 3H), 7.76 (d, J=7.5 Hz, 2H), 7.43 (t, J=7.2 Hz, 2H), 7.33 (td, J=7.4, 1.1 Hz, 2H), 4.44-4.33 (m, 3H), 4.33-4.22 (m, 1H), 3.23 (s, 6H), 2.99 (t, J=5.8 Hz, 2H) ppm.

Step 2. 9H-Fluoren-9-ylmethyl ({[2-({4-[4-(3-bromo-4-fluorophenyl)-5-oxo-4,5-dihydro-1,2,4-oxadiazol-3-yl]-1,2,5-oxadiazol-3-yl}amino)ethyl]amino}sulfonyl)carbamate

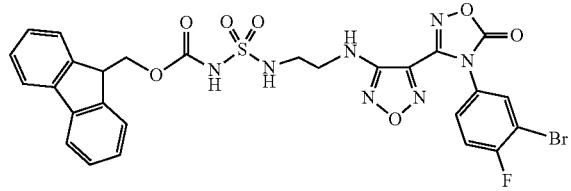

To a stirred suspension of 3-(4-amino-1,2,5-oxadiazol-3-yl)-4-(3-bromo-4-fluorophenyl)-1,2,4-oxadiazol-5(4H)-one (10.00 g, 29.23 mmol) in DCM (160 mL) was added methanesulfonic acid (MeSO$_3$H, 8.46 g, 88.04 mmol) and triethylsilane (Et$_3$SiH, 8.37 g, 71.96 mmol) at ambient temperature over 10 minutes to give a slurry. Solid 9H-fluoren-9-ylmethyl{[(2,2-dimethoxyethyl)amino]sulfonyl}carbamate (12.25 g, 30.14 mmol) was added portionwise (1 g/3-4 min; over 1 h) while maintaining the internal temperature at less than about 20° C. using a water bath. After the addition, the resulting mixture was stirred at about 13 to 22° C. for 3 days. Additional triethylsilane (Et$_3$SiH, 0.1755 g, 1.51 mmol) and 9H-fluoren-9-ylmethyl{[(2,2-dimethoxyethy)amino]sulfonyl}carbamate (0.3082 g, 0.76 mmol) were added and the resulting mixture was stirred at ambient temperature for an additional 23 h. Isopropyl alcohol (IPA, 15 mL) was added and the resulting mixture was stirred at ambient temperature for 1 h. Heptane (100 mL) was added and the mixture was stirred at ambient temperature for an additional 2 h. The solids were collected by filtration, washed with IPA/heptane (1/5; 2×30 mL) and heptane (2×30 mL), and dried under vacuum to afford 9H-fluoren-9-ylmethyl ({[2-({4-[4-(3-bromo-4-fluorophenyl)-5-oxo-4,5-dihydro-1,2,4-oxadiazol-3-yl]-1,2,5-oxadiazol-3-yl}amino)ethyl]amino}sulfonyl)carbamate as a white solid (18.30 g, 91.1% yield). $^1$H NMR (500 MHz, DMSO-$d_6$) δ 11.44 (s, 1H), 8.07 (dd, J=6.2, 2.5 Hz, 1H), 7.90 (t, J=5.6 Hz, 1H), 7.88 (d, J=7.6 Hz, 2H), 7.72 (d, J=7.0 Hz, 2H), 7.71 (ddd, J=8.9, 4.3, 2.6 Hz, 1H), 7.57 (dd, J=8.7, 8.7 Hz, 1H), 7.40 (t, J=7.4 Hz, 2H), 7.31 (td, J=7.4, 1.0 Hz, 2H), 6.55 (t, J=6.0 Hz, 1H), 4.35 (d, J=7.3 Hz, 2H), 4.25 (t, J=7.2 Hz, 1H), 3.39 (q, J=6.4 Hz, 2H), 3.15 (q, J=6.3 Hz, 2H); $^{13}$C NMR (126 MHz, DMSO-$d_6$) δ 159.03 (d, J=248.7 Hz), 156.61 (s), 155.22 (s), 151.55 (s), 148.67 (s), 143.29 (s), 140.68 (s), 133.82 (s), 133.39 (s), 130.05 (d, J=8.5 Hz), 128.54 (d, J=3.2 Hz), 127.73 (s), 127.07 (s), 125.24 (s), 120.11 (s), 117.42 (d, J=24.0 Hz), 108.19 (d, J=22.5 Hz), 66.70 (s), 46.17 (s), 43.34 (s), 40.79 (s) ppm; $^{19}$F NMR (376 MHz, DMSO-$d_6$) δ -103.99--107.39 (m) ppm.

Step 3. 4-({2-[(Aminosulfonyl)amino]ethyl}amino)-N-(3-bromo-4-fluorophenyl)-N'-hydroxy-1,2,5-oxadiazole-3-carboximidamide

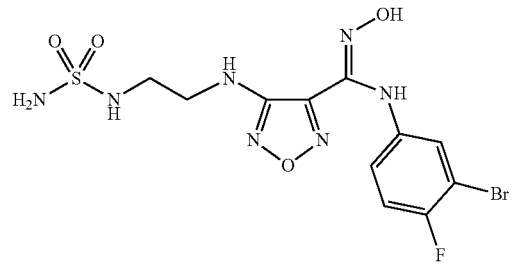 [SMILES: NS(=O)(=O)NCCNc1nonc1/C(=N/O)Nc1ccc(F)c(Br)c1]

Into a 1 L 4-neck round bottom flask was charged 9H-fluoren-9-ylmethyl({[2-({4-[4-(3-bromo-4-fluorophenyl)-5-oxo-4,5-dihydro-1,2,4-oxadiazol-3-yl]-1,2,5-oxadiazol-3-yl}amino)ethyl]amino}sulfonyl)carbamate (25.0 g, 36.4 mmol) and anhydrous THF (250 mL) at ambient temperature to produce a homogeneous solution. The solution was then cooled to 0-5° C. in an ice bath before N,N-bis(2-aminoethyl)ethane-1,2-diamine (114 mL, 728 mmol) was added dropwise over 35 minutes via an addition funnel. The addition funnel was rinsed with anhydrous THF (50 mL) and the rinse was added to the reaction mixture. The cold bath was removed and the reaction was gradually warmed to ambient temperature and stirred at ambient temperature for 2.5 h. EtOAc (400 mL) was added and the resulting mixture was transferred to a 2 L 4-neck round bottom flask and cooled to about 0-5° C. in an ice bath. A solution of 2.0 M aqueous HCl (400 mL, 800.0 mmol) was added dropwise via an addition funnel, while maintaining the internal temperature at below 10° C. The two phases were separated and the aqueous phase was extracted with EtOAc (200 mL). The organic fractions were combined and cooled to about 6-7° C. A solution of 2.0 M aqueous HCl (200.0 mL, 400.0 mmol) was added dropwise to the cold organic fraction, maintaining the internal temperature at below 10° C. The two phases were separated and the organic phase was washed with water (2×400 mL), dried over MgSO$_4$, and concentrated under reduced pressure to a light yellow syrup. The syrup was dissolved in EtOAc (60.0 mL) to yield a homogeneous solution. To the solution was added a solution of DCM (250.0 mL) and tert-butyl methyl ether (TBME, 100.0 mL) dropwise. The resulting slurry was stirred overnight at room temperature, then cooled in an ice bath for 1 h. The solids were collected by filtration, washed with an ice cold 250 mL solution of DCM (150 mL) and TBME (100 mL), and dried under vacuum to give 14.4 g of the crude desired product as white solids.

The crude product was dissolved in EtOAc (140.0 mL) at 60° C. and the warm solution was filtered. The filtrate was cooled to room temperature before heptane (100.0 mL) was added dropwise over 55 min. The resulting mixture was then stirred overnight at room temperature. The solids were collected by filtration, washed with a 2:1 mixture of heptane and EtOAc (75 mL), and dried under vacuum at 40-50° C. to constant weight to afford 4-({2-[(aminosulfonyl)amino] ethyl}amino)-N-(3-bromo-4-fluorophenyl)-N'-hydroxy-1,2, 5-oxadiazole-3-carboximidamide (12.9 g, 81% yield) as a white solid.

Example A

Human Indoleamine 2,3-dioxygenasae (IDO) Enzyme Assay

Human indoleamine 2,3-dioxygenasae (IDO) with an N-terminal His tag was expressed in *E. coli* and purified to homogeneity. IDO catalyzes the oxidative cleavage of the pyrrole ring of the indole nucleus of tryptophan to yield N'-formylkynurenine. The assays were performed at room temperature as described in the literature using 95 nM IDO and 2 mM D-Trp in the presence of 20 mM ascorbate, 5 µM methylene blue and 0.2 mg/mL catalase in 50 mM potassium phosphate buffer (pH 6.5). The initial reaction rates were recorded by continuously following the absorbance increase at 321 nm due to the formation of N'-formylkynurenine (See: Sono, M., et al., 1980, *J. Biol. Chem.* 255, 1339-1345). The compound of Formula I was tested in the assay of Example A and found to have an IC$_{50}$ of <200 nM.

Example B

Determination of Inhibitor Activity in HeLa Cell-Based Indoleamine 2,3-dioxygenase (IDO)/Kynurenine Assay HeLa cells (#CCL-2) were obtained from the American Type Tissue Culture Collection (ATCC, Manassas, Va.) and routinely maintained in minimum essential medium (eagle) with 2 mM L-glutamine and Earle's BSS adjusted to contain 1.5 g/L sodium bicarbonate, 0.1 mM non-essential amino acids, 1 mM sodium pyruvate and 10% fetal bovine serum (all from Invitrogen). Cells were kept at 37° C. in a humidified incubator supplied with 5% CO$_2$. The assay was performed as follows: HeLa cells were seeded in a 96 well culture plate at a density of 5×10$^3$ per well and grown overnight. On the next day, IFN-γ (50 ng/mL final concentration) and serial dilutions of compounds (in total volume of 200 µL culture medium) were added into cells. After 48 hours of incubation, 140 µL of the supernatant per well was transferred to a new 96 well plate. 10 µL of 6.1 N trichloroacetic acid (#T0699, Sigma) was mixed into each well and incubated at 50° C. for 30 min to hydrolyze N-formylkynurenine produced by indoleamine 2,3-dioxygenase to kynurenine. The reaction mixture was then centrifuged for 10 min at 2500 rpm to remove sediments. 100 µL of the supernatant per well was transferred to another 96 well plate and mixed with 100 µL of 2% (w/v) p-dimethylaminobenzaldehyde (#15647-7, Sigma-Aldrich) in acetic acid. The yellow color derived from Kynurenine was measured at 480 nm using a SPECTRAmax 250 microplate reader (Molecular Devices). L-kynurenine (#K8625, Sigma) was used as standard. The standards (240, 120, 60, 30, 15, 7.5, 3.75, 1.87 µM) were prepared in 100 µL culture media and mixed with equal volume of 2% (w/v) p-dimethylaminobenzaldehyde. The percent inhibition at individual concentrations was determined and the average values of duplicates were obtained. The data was analyzed by using nonlinear regression to generate IC$_{50}$ values (Prism Graphpad). See: Takikawa 0, et al., 1988, *J. Biol. Chem.*, 263(4): 2041-8.

Example C

Determination of Effect of IDO Inhibitors on T Cell Proliferation that is Suppressed by IDO-Expressing Dendritic Cells Monocytes were collected from human peripheral mononuclear cells by leukophoresis. Monocytes were then seeded at a density of 1×10$^6$ cells/well in a 96 well plate, using RPMI 1640 medium supplemented with 10% fetal bovine serum and 2 mM L-glutamine (all from Invitrogen). Adherent cells were retained on the plate after overnight culture at 37° C. Adherent monocytes were then stimulated for 5-7 days with 100 ng/ml GM-CSF (#300-03, PeproTech) and 250 ng/ml IL-4 (#200-04, PeproTech), followed by activation with 5 µg/mL LPS from *Salmonella typhimurium* (#437650, Sigma) and 50 ng/mL IFN-γ (#285-IF, R&D Systems) for additional 2 days to induce dendritic cell maturation.

After dendritic cell activation, the medium was replaced with completed RPMI 1640 supplemented with 100-200 U/mL IL-2 (#CYT-209, ProSpec-Tany TechnoGene) and 100 ng/mL anti-CD3 antibody (#555336, PharMingen), T cells (2-3×10$^5$ cells/well), and serial dilutions of IDO compounds. After incubation for 2 more days, T cell proliferation was measured by BrdU incorporation assay, using a colorimetric Cell Proliferation ELISA kit per manufacturer's instruction (#1647229, Roche Molecular Biochemicals). Cells were continuously cultured for 16-18 hrs in presence of 10 µM BrdU labeling solution. Then, the labeling medium was removed, and 200 µL FixDenat per well was added to the cells and incubated for 30 minutes at room temperature. The FixDenat solution was removed and 100 µL/well anti-BrdU-POD antibody conjugate working solution was added. The reaction was carried out for 90 minutes at room temperature. The antibody conjugate was then removed, and cells were rinsed three times with 200 µL/well washing solution. Finally, 100 µL/well of substrate solution was added and the results were obtained using a microplate reader (Spectra Max PLUS, Molecular Devices) during color development. Multiple readings at various time points were obtained to ensure the data was within the linear range. The data was routinely obtained from replicated experiments, and appropriate controls were included. See: Terness P, et al. 2002, *J. Exp. Med.*, 196(4): 447-57; and Hwu, P, et al. 2000, *J. Immunol.*, 164(7): 3596-9.

Example D

In Vivo Testing of IDO Inhibitors for Antitumor Activity

In vivo anti-tumor efficacy can be tested using modified tumor allograft/xenograft protocols. For instance, it has been described in the literature that IDO inhibition can syngerize with cytotoxic chemotherapy in immune-competent mice (Muller, A. J., et al. 2005, *Nat. Med.* 11:312-319). This synergy was shown to be dependent on T-cells by comparison of the synergistic effects of an investigational IDO inhibitor in murine tumor xenograft models (e.g. B16 and related variants, CT-26, LLC) grown in immune competent syngenic mice to that observed in syngenic mice treated with neutralizing anti-CD4 antibodies, or the same tumors grown in immune-compromised mice (e.g. nu/nu).

The concept of differential anti-tumor effects in immune-competent versus immune-compromised mice may also permit testing of investigational IDO inhibitors as single agents. For instance, LLC tumors grow well in their syngenic host strain, C57B1/6. However, if these mice are treated with the IDO inhibitor 1-MT (versus placebo) the formation of tumors is markedly delayed, implying that IDO inhibition was growth inhibitory (Friberg, M., et al. 2002, *Int. J. Cancer* 101:151-155). Following this logic, one can examine the efficacy of IDO inhibition in the LLC xenograft tumor model grown in C57B1/6 immune competent mice and compare that to the effects of IDO inhibitors on LLC tumor growth in nude or SCID mice (or C57B1/6 mice treated with antibodies that neutralize T-cell activity). As the effects of relieving the tumor-mediated immune suppressive activity of IDO will likely differ depending on the immunogenic potential of different tumor models, genetic modifications can be made to the tumor cells to increase their immunogenic potential. For instance, expression of GM-CSF in B16.F10 cells increases their immunogenic potential (Dranoff, G., et al. 1993, *Proc. Natl. Acad. Sci.*, USA, 90:3539-3543). As such, in some tumor models (e.g. B16.F10) one can generate [poly]clones that express immune stimulatory proteins such as GM-CSF and test the growth inhibitory effects of IDO inhibitors against tumors established from these tumor cells in both immune-competent and -compromised mice.

A third avenue for assessing the efficacy of IDO inhibitors in vivo employs 'pre-immunization' murine tumor allograft/xenograft models. In these models, immune-competent mice are sensitized to a specific tumor antigen or antigens to mimic a therapeutic anti-tumor vaccination. This primes the mice for an anti-tumor response mediated by the immune system when mice are subsequently challenged with murine tumor cell lines (possessing similar tumor antigens to those used for immunization) in xenograft experiments. Expression of IDO has been shown to blunt the anti-tumor response and allow xenografts to grow more rapidly. Importantly, the growth of tumors in this model is inhibited by the IDO inhibitor 1-MT (Uyttenhove, C., et al. 2003, *Nat. Med.* 9:1269-1274). This model is particularly attractive as IDO activity is permissive for P815 tumor growth and specific inhibition of IDO should therefore growth inhibitory.

Lastly, therapeutic immunization may be used to evaluate the impact of IDO inhibitors in vivo. For example, it has been demonstrated using B16-BL6 cells that one can challenge Blk/6 mice with an intravenous injection of tumor cells followed by treatment with a well characterized immunogenic peptide (e.g. TRP-2) expressed by the tumor cells (Ji, et al., 2005, *J. Immunol,* 175: 1456-63). Importantly, immune system modifiers, such as anti-CTL-4 antibody, can improve responses to such therapeutic immunizations. The impact of IDO inhibitors may be evaluated in a similar manner-tumor peptide immunization with or without IDO inhibitor. Efficacy is assess by animal survival (time to morbidity) or by the measurement of tumor metastases to the lungs and/or other organs at defined timepoints.

In any/all of the above mentioned models, it may also be possible to directly and/or indirectly measure the number and/or activity of tumor reactive immune cells. Methods for measuring the number and/or activity of tumor reactive immune cells are well established and can be performed using techniques familiar to those schooled in the art (Current Protocols in Immunology, Vol. 4, Coligan, J. E., et al.; *Immunotherapy of Cancer*, Human Press, 2006, Disis, M. L. and references therein). Conceptually, a reduction in the immune suppressive effects of IDO may result in increased numbers or reactivity of tumor specific immune cells. Further, IDO inhibition may further increase the number or reactivity of tumor reactive immune cells when combined with other therapeutics, for example chemotherapeutics and/or immune modulators (e.g. anti-CTLA4 antibody).

All allograft/xenograft experiments can be performed using standard tumor techniques (reviewed by Corbett, et al., In *Cancer Drug Discovery and Development: Anticancer Drug Development Guide: Preclinical Screening*, Clinical Trials, and Approval, $2^{nd}$ Ed. Teicher, B. A. and Andrews, P. A., Gumana Press Inc.: Totowa, N.J., 2004). The cloning and introduction of genes (e.g. IDO, GM-CSF) into tumor cell lines, can be performed using techniques familiar to those schooled in the art (reviewed in Sambrook, J. and Russel, D., Molecular Cloning: A laboratory Manual ($3^{rd}$ edition), Cold Spring Harbor Laboratory Press: Cold Spring Harbor, N.Y., 2001).

Example E

In Vivo Testing of IDO Inhibitors in Human Immunodeficiency Virus-1 (HW-1) Encephalitis Model 1. Cell Isolation and Viral Infection Monocytes and PBL can be obtained by countercurrent centrifugal elutriation of leukopheresis packs from HIV-1, 2 and hepatitis B seronegative donors. Monocytes are cultivated in suspension culture using Teflon flasks in Dulbecco's Modified Eagle's Medium (DMEM, Sigma-Aldrich) supplemented with 10% heat-inactivated pooled human serum, 1% glutamine, 50 µg/mL gentamicin, 10 µg/mL ciprofloxacin (Sigma), and 1000 U/mL highly purified recombinant human macrophage colony stimulating factor. After seven days in culture, MDM are infected with HIV-1ADA at multiplicity of infection of 0.01.

2. Hu-PBL-NOD/SCID HIVE Mice

Four-wk old male NOD/C.B-17 SCID mice can be purchased (Jackson Laboratory). Animals are maintained in sterile microisolator cages under pathogen-free conditions. All animals are injected intraperitoneally with rat anti-CD122 (0.25 mg/mouse) three days before PBL transplantation and twice with rabbit asialo-GM1 antibodies (0.2 mg/mouse)

(Wako) one day before and three days after PBL injection (20×10⁶ cells/mouse). HIV-1$_{ADA}$-infected MDM (3×10⁵ cells in 10 µl) are injected intracranially (i.c.) eight days following PBL reconstitution generating hu-PBL-NOD/SCID HIVE mice. Immediately following i.c. injection of HIV-1 infected MDM the hu-PBL-NOD/SCID HIVE mice are subcutaneously (s.c) implanted with control (vehicle) or compound pellets (14 or 28 day slow release, Innovative Research). Initial experiments are designed to confirm the induction of virus-specific CTL in the hu PBL-NOD/SCID HIVE animals treated with IDO compounds. This is confirmed by tetramer staining and neuropathologic analyses of MDM elimination from the brain tissue. Then, the experiment is designed to analyze human lymphocyte reconstitution, humoral immune responses, and neuropathological alterations. In these experiments, animals are bled on day 7 and sacrificed at 14 and 21 days after i.c. injection of human MDM. Blood collected in EDTA-containing tubes is used for flow cytometry and plasma is used for detection of HIV-1 p24 using ELISA (Beckman Coulter™). HIV-1-specific antibodies are detected by Western blot tests according to the manufacturer instructions (Cambridge Biotech HIV-1 Western blot kit, Calypte Biomedical). Similar amount of virus-specific antibodies are detected in control and compound-treated animals. A total of three independent experiments can be performed using three different human leukocyte donors.

3. FACScan of Peripheral Blood and Spleen in Hu PBL-NOD/SCID HIVE Mice

Two-color FACS analysis can be performed on peripheral blood at wk 1-3 and splenocytes at wk 2 and 3 after i.c. injection of human MDM. Cells are incubated with fluorochrome-conjugated monoclonal Abs (mAbs) to human CD4, CD8, CD56, CD3, IFN-γ (eBioscience) for 30 min at 4° C. To evaluate the cellular immune response, IFN-γ intracellular staining is performed in combination with anti-human CD8 and FITC-conjugated anti-mouse CD45 to exclude murine cells. To determine the Ag-specific CTL, allophycocyanin-conjugated tetramer staining for HIV-1$^{gag}$ (p17 (aa77-85) SLYNTVATL, SL-9) and HIV-1$^{pol}$ [(aa476-485) ILKEPVHGV, IL-9] is performed on phytohemaglutinin/interleukin-2 (PHA/IL-2)-stimulated splenocytes. Cells are stained following the recommendation of the NIH/National Institute of Allergy and Infections Disease, National Tetramer Core Facilities. Data were analyzed with a FACS Calibur™ using CellQuest software (Becton Dickinson Immunocytometry System).

4. Histopathology and Image Analyses

Brain tissue is collected at days 14 and 21 after i.c. injection of MDM, fixed in 4% phosphate-buffered paraformaldehyde and embedded in paraffin or frozen at −80° C. for later use. Coronal sections from the embedded blocks are cut in order to identify the injection site. For each mouse, 30-100 (5-µm-thick) serial sections are cut from the human MDM injection site and 3-7 slides (10 sections apart) are analyzed. Brain sections are deparaffinized with xylene and hydrated in gradient alcohols Immunohistochemical staining follows a basic indirect protocol, using antigen retrieval by heating to 95° C. in 0.01 mol/L citrate buffer for 30 min for antigen retrieval. To identify human cells in mouse brains, mAb to vimentin (1:50, clone 3B4, Dako Corporation), which identifies all human leukocytes is used. Human MDM and CD8⁺ lymphocytes are detected with CD68 (1:50 dilution, clone KP 1) and CD8 (1:50 dilution, clone 144B) antibodies, respectively. Virus-infected cells are labeled with mAb to HIV-1 p24 (1:10, clone Kal-1, all from Dako). Reactive murine microglial cells are detected with Iba-1 antibody (1:500, Wako). Expression of human IDO (huIDO) is visualized with Abs obtained from the Department of Cell Pharmacology, Central Research Institute, Graduate School of Medicine, Hokkaido University, Sapporo, Japan. Primary antibodies are detected with the appropriate biotinylated secondary antibodies and visualized with avidin-biotin complexes (Vectastain Elite ABC kit, Vector Laboratories) and horseradish peroxidase (HRP) coupled dextran polymer (EnVision, Dako Corporation) Immunostained sections are counterstained with Mayer's hematoxylin. Sections from which primary antibody is deleted or irrelevant IgG isotype is incorporated served as controls. Two independent observers in a blinded fashion count the numbers of CD8⁺ lymphocytes, CD68⁺ MDM and HIV-1 p24⁺ cells in each section from each mouse. Light microscopic examination is performed with a Nikon Eclipse 800 microscope (Nikon Instruments Inc). Semi-quantitative analysis for Ibal (percentage of area occupied by immunostaining) is carried out by computer-assisted image analysis (Image-Pro®Plus, Media Cybernetics) as previously described.

5. Statistical Analysis

Data can be analyzed using Prism (Graph Pad) with Student t-test for comparisons and ANOVA. P-values <0.05 were considered significant.

6. Reference

Poluektova L Y, Munn D H, Persidsky Y, and Gendelman H E (2002). Generation of cytotoxic T cells against virus-infected human brain macrophages in a murine model of HIV-1 encephalitis. *J. Immunol.* 168(8):3941-9.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in their entirety.

What it claimed is:

1. A process comprising reacting a compound of Formula F5:

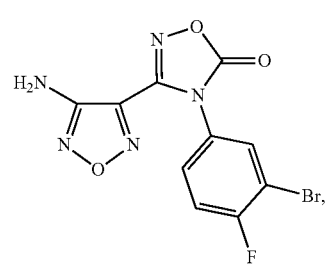

with an aldehyde of Formula F6:

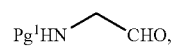

wherein Pg¹ is an amino protecting group, to afford a compound of Formula F7:

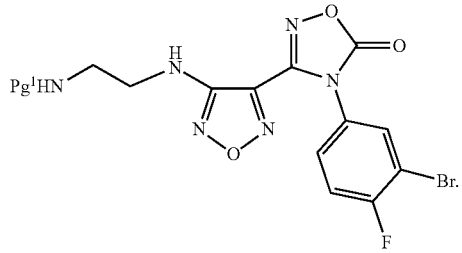

F7

2. The process of claim 1, wherein Pg¹ is ethoxycarbonyl, tert-butoxycarbonyl, benzyloxycarbonyl, or 9-fluorenylmethyloxycarbonyl.

3. The process of claim 1, wherein Pg¹ is tert-butoxycarbonyl.

4. The process of claim 1, wherein said reacting is performed in the presence of a reducing agent.

5. The process of claim 4, wherein said reducing agent is a borohydride reducing agent.

6. The process of claim 5, wherein said borohydride reducing agent is sodium triacetoxyborohydride.

7. The process of claim 1, further comprising deprotecting said compound of Formula F7 to afford a compound of Formula F8:

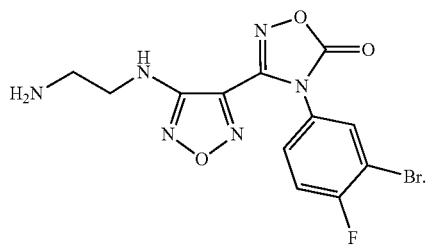

F8

8. The process of claim 7, wherein said deprotecting comprises reacting the compound of Formula F7 with hydrochloric acid.

9. The process of claim 7, further comprising reacting said compound of Formula F8, with Pg²-NH—SO₂—X, in the presence of an organic base to afford a compound of Formula F9:

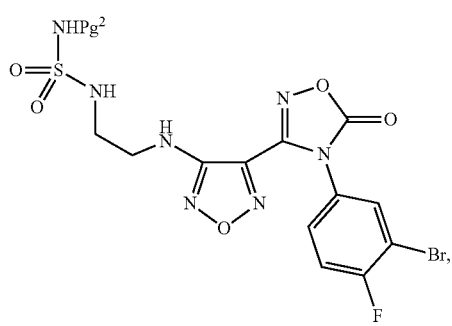

F9 wherein:

Pg² is an amino protecting group; and

X is halo.

10. The process of claim 9, wherein Pg² is ethoxycarbonyl, tert-butoxycarbonyl, benzyloxycarbonyl, or 9-fluorenylmethyloxycarbonyl.

11. The process of claim 9, wherein Pg² is tert-butoxycarbonyl.

12. The process of claim 9, wherein X is chloro.

13. The process of claim 9, further comprising deprotecting said compound of Formula F9 to afford a compound of Formula F10:

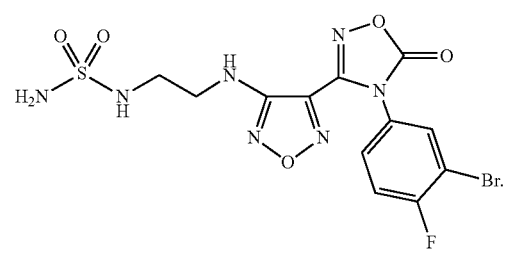

F10

14. The process of claim 13, wherein said deprotecting comprises reacting a compound of Formula F9 with hydrochloric acid.

15. The process of claim 13, wherein said deprotecting comprises reacting a compound of Formula F9 with hydrochloric acid in a solvent component comprising ethyl acetate.

16. The process of claim 13, further comprising reacting said compound of Formula F10 with a base to afford a compound of Formula I:

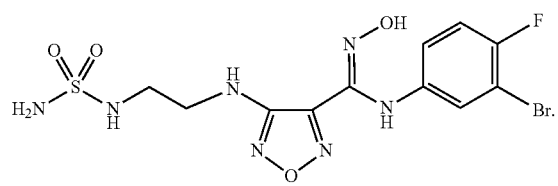

I

17. The process of claim 16, wherein said base is sodium hydroxide.

18. A process, comprising reacting a compound of Formula F15:

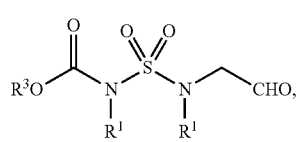

F15 with a compound of Formula F5:

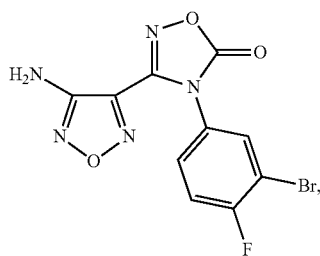

to afford a compound of Formula F16:

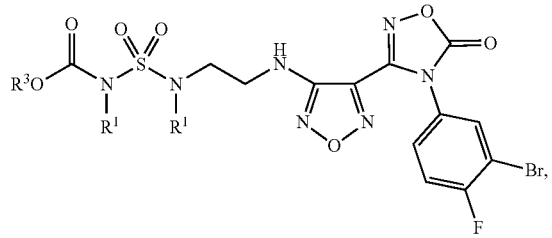

wherein:
each $R^1$ is independently an amino protecting group; and $R^3$ is $C_{1-6}$ alkyl or benzyl.

19. The process of claim 18, wherein each $R^1$ is $C_{2-4}$ alkenyl-$C_{1-3}$ alkyl or phenyl-$C_{1-3}$ alkyl, wherein said phenyl-$C_{1-3}$ alkyl is optionally substituted by 1, 2, or 3 independently selected $C_{1-4}$ alkoxy groups.

20. The process of claim 18, wherein each $R^1$ is allyl.

21. The process of claim 18, wherein each $R^1$ is 4-methoxybenzyl.

22. The process of claim 18, wherein $R^3$ is $C_{1-6}$ alkyl.

23. The process of claim 18, wherein $R^3$ is tert-butyl.

24. The process of claim 18, wherein said reacting is performed in the presence of a reducing agent.

25. The process of claim 24, wherein said reducing agent is a borohydride reducing agent.

26. The process of claim 25, wherein said borohydride reducing agent is sodium triacetoxyborohydride.

27. The process of claim 24, wherein said reacting is performed in the presence of trifluoroacetic acid.

28. The process of claim 18, further comprising deprotecting said compound of Formula F16 to afford a compound of Formula F10:

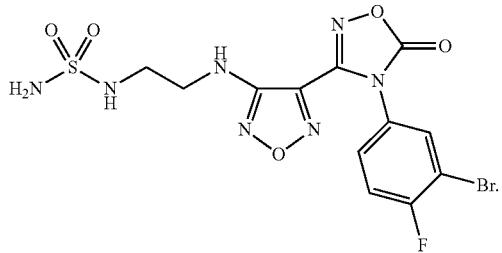

29. The process of claim 28, wherein said deprotecting comprises reacting a compound of Formula F16 with trifluoroacetic acid.

30. The process of claim 28, wherein said deprotecting comprises reacting a compound of Formula F16 with is hydrochloric acid.

31. The process of claim 18, wherein said compound of Formula F15 is obtained by a process comprising treating a compound of Formula F14:

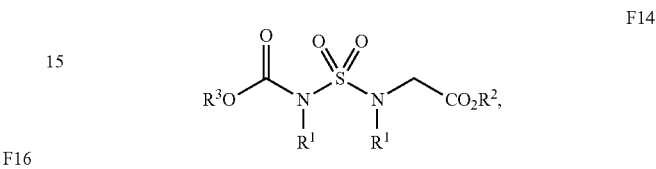

with a reducing agent to afford said compound of Formula F15; wherein $R^2$ is $C_{1-4}$ alkyl.

32. The process of claim 31, wherein said reducing agent is diisobutylaluminum hydride.

33. The process of claim 31, wherein said compound of Formula F14 is obtained by a process comprising protecting a compound of Formula F13:

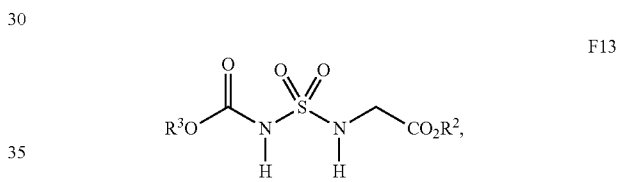

with one or more independently selected amino protecting agents to afford a compound of Formula F14.

34. The process of claim 33, wherein said one or more amino protecting agents is selected from allyl bromide and 4-methoxybenzyl chloride.

35. The process of claim 33, wherein said protecting is performed in the presence of a base.

36. A compound of Formula F15:

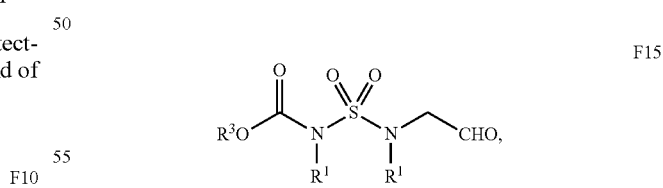

wherein:
$R^3$ is $C_{1-6}$ alkyl or benzyl; and
each $R^1$ is independently an amino protecting group.

37. The compound of claim 36, which is tert-butyl allyl{[allyl(2-oxoethyl)amino]sulfonyl}carbamate.

38. The compound of claim 36, which is tert-butyl(4-methoxybenzyl){[(4-methoxybenzyl)(2-oxoethyl)amino]sulfonyl}carbamate.

39. A process, comprising reacting a compound of Formula F17:

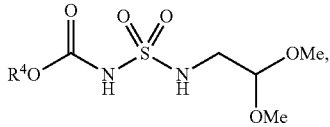

wherein R⁴ is $C_{1-6}$ alkyl, $C_{1-6}$ haloalkyl, benzyl, or 9H-fluoren-9-ylmethyl with a compound of Formula F5:

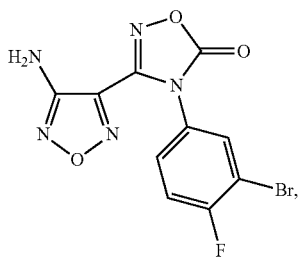

to afford a compound of Formula F18:

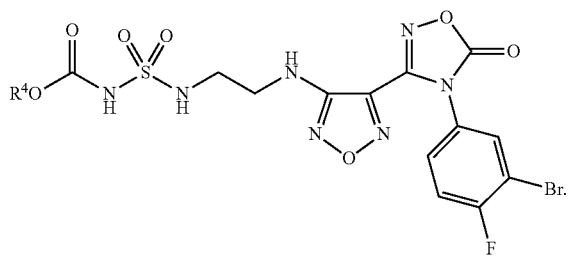

40. The process of claim 39, wherein R⁴ is tent-butyl.

41. The process of claim 39, wherein R⁴ is benzyl.

42. The process of claim 39, wherein R⁴ is ethyl.

43. The process of claim 39, wherein R⁴ is 2,2,2-trichloroethyl.

44. The process of claim 40, wherein said reacting is carried out in the presence of a reducing agent.

45. The process of claim 44, wherein said reducing agent is triethylsilane.

46. The process of claim 45, wherein said reacting is carried out in the presence of an organic acid.

47. The process of claim 46, wherein said organic acid is trifluoroacetic acid.

48. The process of claim 40, further comprising deprotecting said compound of Formula F18 to afford a compound of Formula F10:

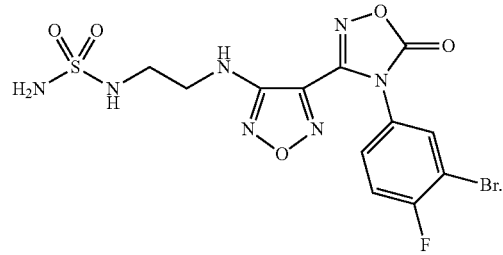

49. The process of claim 48, wherein said deprotecting comprises reacting the compound of Formula F18 with zinc in the presence of acetic acid.

50. The process of claim 48, further comprising reacting said compound of Formula F10 with a base to afford a compound of Formula I:

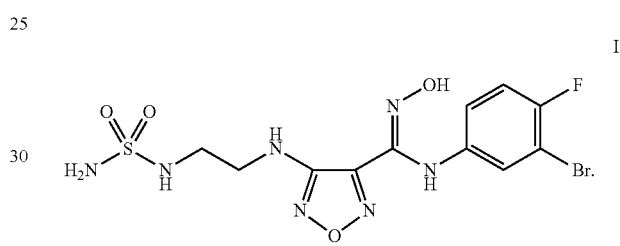

51. The process of claim 50, wherein said base is sodium hydroxide.

52. The process of claim 39, wherein R⁴ is 9H-fluoren-9-ylmethyl.

53. The process of claim 52, wherein said reacting is carried out in the presence of a reducing agent.

54. The process of claim 53, wherein said reducing agent is triethylsilane.

55. The process of claim 54, wherein said reacting is carried out in the presence of an organic acid.

56. The process of claim 55, wherein said organic acid is methanesulfonic acid.

57. The process of claim 52, further comprising converting said compound of Formula F18 to a compound of Formula I:

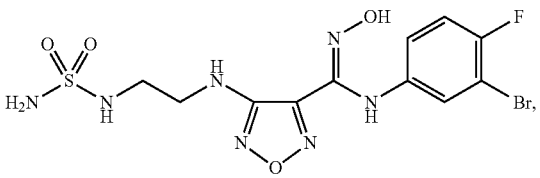

wherein said converting comprises combining the compound of Formula F18 with a base to form a first mixture.

58. The process of claim 57, wherein said base is N,N-bis(2-aminoethyl)ethane-1,2-diamine.

59. The process of claim 57, wherein said converting further comprises adding aqueous hydrochloric acid to said first mixture.

60. A compound of Formula F17:

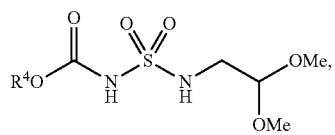

wherein $R^4$ is $C_{1-6}$ haloalkyl, benzyl, or 9H-fluoren-9-yl-methyl.

61. A compound which is tert-butyl N-(2,2-dimethoxyethyl)sulfamoylcarbamate.

62. The compound of claim 60, which is benzyl N-(2,2-dimethoxyethyl)sulfamoylcarbamate.

63. A compound which is ethyl N-(2,2-dimethoxyethyl)sulfamoylcarbamate.

64. The compound of claim 60, which is 2,2,2-trichloroethyl N-(2,2-dimethoxyethyl)sulfamoylcarbamate.

65. The compound of claim 60, which is (9H-fluoren-9-yl)methyl N-(2,2-dimethoxyethy)sulfamoylcarbamate.

66. A process, comprising:

i) reacting a compound of Formula F19:

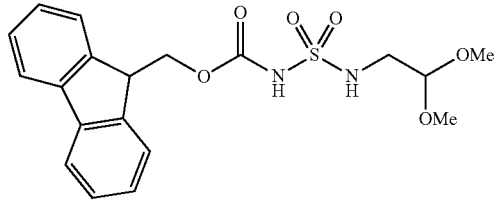

with a compound of Formula F5:

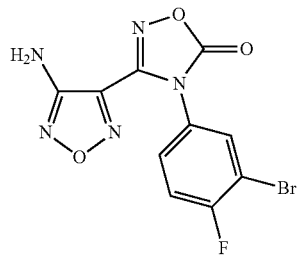

in the presence of triethylsilane and methanesulfonic acid to afford a compound of Formula F20:

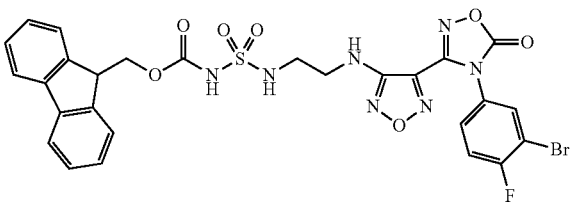

and ii) converting said compound of Formula F20 to a compound of Formula I:

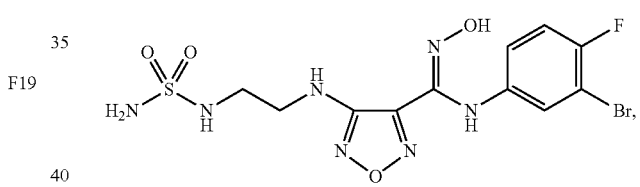

wherein said converting comprises combining said compound of Formula F20 with N,N-bis(2-aminoethyl)ethane-1,2-diamine.

* * * * *

UNITED STATES PATENT AND TRADEMARK OFFICE
CERTIFICATE OF CORRECTION

PATENT NO. : 9,321,755 B2  
APPLICATION NO. : 14/535781  
DATED : April 26, 2016  
INVENTOR(S) : Ming Tao et al.

Page 1 of 1

It is certified that error appears in the above-identified patent and that said Letters Patent is hereby corrected as shown below:

In the Claims

Col. 71, Line 49, Claim 40, delete "tent-butyl." and insert -- tert-butyl. --.

Col. 73, Line 31, Claim 65, delete "(2,2-dimethoxyethy)" and insert -- (2,2-dimethoxyethyl) --.

Signed and Sealed this  
Second Day of August, 2016

Michelle K. Lee  
*Director of the United States Patent and Trademark Office*